(12) United States Patent
Lu et al.

(10) Patent No.: US 8,415,461 B2
(45) Date of Patent: Apr. 9, 2013

(54) AMPHIPHILIC SUBSTANCES AND FUNCTIONALIZED LIPID VESICLES INCLUDING THE SAME

(75) Inventors: Yi Lu, Champaign, IL (US); Gerard Wong, Urbana, IL (US); Mehmet Veysel Yigit, Malden, MA (US); Abhijit Mishra, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 12/523,443

(22) PCT Filed: Jan. 16, 2008

(86) PCT No.: PCT/US2008/051185
§ 371 (c)(1),
(2), (4) Date: Mar. 15, 2010

(87) PCT Pub. No.: WO2008/089248
PCT Pub. Date: Jul. 24, 2008

(65) Prior Publication Data
US 2010/0166842 A1  Jul. 1, 2010

Related U.S. Application Data

(60) Provisional application No. 60/885,744, filed on Jan. 19, 2007.

(51) Int. Cl.
*C07H 21/04* (2006.01)
*A61K 48/00* (2006.01)
*C12Q 1/68* (2006.01)

(52) U.S. Cl.
USPC ......... 536/23.1; 536/24.1; 514/44 A; 435/6.1; 435/325; 435/375

(58) Field of Classification Search .................. None
See application file for complete search history.

(56) References Cited

U.S. PATENT DOCUMENTS

| | | | |
|---|---|---|---|
| 4,362,603 A | 12/1982 | Presson et al. |
| 4,703,017 A | 10/1987 | Campbell et al. |
| 4,746,631 A | 5/1988 | Clagett |
| 4,855,240 A | 8/1989 | Rosenstein et al. |
| 4,857,319 A | 8/1989 | Crowe et al. |
| 5,008,109 A | 4/1991 | Tin |
| 5,459,040 A | 10/1995 | Hammock et al. |
| 5,472,881 A | 12/1995 | Beebe et al. |
| 5,580,967 A | 12/1996 | Joyce |
| 5,593,835 A | 1/1997 | Rando et al. |
| 5,631,148 A | 5/1997 | Urdea |
| 5,663,064 A | 9/1997 | Burke et al. |
| 5,807,718 A | 9/1998 | Joyce et al. |
| 5,807,967 A | 9/1998 | Snow et al. |
| 5,910,408 A | 6/1999 | Szostak et al. |
| 5,989,813 A | 11/1999 | Gerdes |
| 6,040,138 A | 3/2000 | Lockhart et al. |
| 6,110,462 A | 8/2000 | Barbas et al. |
| 6,159,347 A | 12/2000 | Sumner, Jr. et al. |
| 6,287,765 B1 | 9/2001 | Cubicciotti |
| 6,316,194 B1 | 11/2001 | Karn et al. |
| 6,326,508 B1 | 12/2001 | Godbole et al. |
| 6,361,944 B1 | 3/2002 | Mirkin et al. |
| 6,387,617 B1 | 5/2002 | Asher et al. |
| 6,426,335 B1 | 7/2002 | Janjic et al. |
| 6,451,535 B1 | 9/2002 | Jenne et al. |
| 6,485,982 B1 | 11/2002 | Charlton |
| 6,541,617 B1 | 4/2003 | Bamdad et al. |
| 6,630,306 B1 | 10/2003 | Breaker |
| 6,706,474 B1 | 3/2004 | Lu et al. |
| 6,818,455 B2 | 11/2004 | May et al. |
| 6,843,890 B1 | 1/2005 | Godbole |
| 6,849,414 B2 | 2/2005 | Guan et al. |
| 6,890,719 B2 | 5/2005 | Lu et al. |
| 7,109,165 B2 | 9/2006 | Matulic-Adamic et al. |
| 7,192,708 B2 | 3/2007 | Lu et al. |
| 7,332,283 B2 | 2/2008 | Lu et al. |
| 7,459,145 B2 | 12/2008 | Bao et al. |
| 7,485,419 B2 | 2/2009 | Lu et al. |

(Continued)

FOREIGN PATENT DOCUMENTS

| | | |
|---|---|---|
| EP | 121970 | 10/1984 |
| EP | 1219708 | 7/2002 |

(Continued)

OTHER PUBLICATIONS

Abstract of Joyce, G., "Design and catalytic activity of enzyumic DNA molecules", (1998).
Aggarwal, S.K., et al., "Determination of lead in urine and whole blood by stable isotope dilution gas chromatography-mass spectrometry", Clinical Chemistry, vol. 40, No. 8, pp. 1494-1502, (1994).
Alivisatos, A.P., et al., "Organization of "nanocrystal molecules" using DNA", Nature, vol. 382, pp. 609-611, (1996).
Allara, D. et al., "Spontaneously organized molecular assemblies. 1.Formation, dynamics and physical properties of n-alkanoic acids adsorbed from solution on an oxidized aluminum surface", Langmuir, vol. 1, No. 1, pp. 45-52, (1985).
Andreola, M-L., et al., "DNA aptamers selected against the HIV-1 RNase H display in vitro antiviral activity", Biochemistry, vol. 40, No. 34, pp. 10087-10094, (2001).
Bain, C. D., et al., "Modeling organic surfaces with self-assembled monolayers", Angew. Chem. Int. Ed. Engl., vol. 28, No. 4, pp. 506-512, (1989).

(Continued)

*Primary Examiner* — Doug Schultz
(74) *Attorney, Agent, or Firm* — Klarquist Sparkman, LLP

(57) ABSTRACT

An amphiphilic substance includes a hydrophobic group, and a polynucleotide group attached to the hydrophobic group. The polynucleotide group includes a first polynucleotide segment and a second polynucleotide segment. The first and second polynucleotide segments are at least partially complementary and are bound together by interactions including base pairing. At least one of the first and second segments includes at least one of an aptamer and a nucleic acid-based enzyme. A lipid vesicle may include the amphiphilic substance, a first polar lipid that is an unstable vesicle former, and a polar liquid. Upon exposure to a rupture agent, the vesicle may rupture, releasing the contents of the vesicle. Substances that may be released from the vesicle include bioactive agents, such as drug agents.

13 Claims, 7 Drawing Sheets

U.S. PATENT DOCUMENTS

| | | | |
|---|---|---|---|
| 7,534,560 B2 | 5/2009 | Lu et al. | |
| 7,612,185 B2 | 11/2009 | Lu et al. | |
| 7,799,554 B2 | 9/2010 | Mazumdar et al. | |
| 7,829,350 B2 | 11/2010 | Josephson et al. | |
| 7,892,734 B2 | 2/2011 | Lu et al. | |
| 7,902,353 B2 | 3/2011 | Lu et al. | |
| 7,906,320 B2 | 3/2011 | Lu et al. | |
| 2003/0149257 A1 | 8/2003 | Sorge et al. | |
| 2003/0215810 A1 | 11/2003 | Lu et al. | |
| 2003/0235611 A1 | 12/2003 | Ehringer et al. | |
| 2004/0018515 A1 | 1/2004 | Diener et al. | |
| 2004/0110167 A1 | 6/2004 | Gerdes et al. | |
| 2004/0126882 A1 | 7/2004 | Ellington et al. | |
| 2004/0158051 A1 | 8/2004 | Ozkan et al. | |
| 2004/0175693 A1 | 9/2004 | Lu et al. | |
| 2005/0037075 A1 | 2/2005 | Farokhzad et al. | |
| 2005/0089890 A1* | 4/2005 | Cubicciotti | 435/6 |
| 2005/0136500 A1 | 6/2005 | Yang et al. | |
| 2005/0282186 A1 | 12/2005 | Lu et al. | |
| 2006/0019406 A1 | 1/2006 | Wei et al. | |
| 2006/0040408 A1 | 2/2006 | Jones et al. | |
| 2006/0045910 A1 | 3/2006 | Ehringer | |
| 2006/0094026 A1 | 5/2006 | Lu et al. | |
| 2006/0166222 A1 | 7/2006 | Lu et al. | |
| 2007/0037171 A1 | 2/2007 | Lu et al. | |
| 2007/0269821 A1 | 11/2007 | Mazumdar et al. | |
| 2008/0176228 A1 | 7/2008 | Lu et al. | |
| 2009/0011402 A1 | 1/2009 | Lu et al. | |
| 2009/0029874 A1 | 1/2009 | Lu et al. | |
| 2009/0197261 A1 | 8/2009 | Lu et al. | |
| 2010/0105039 A1 | 4/2010 | Lu et al. | |
| 2010/0151579 A1 | 6/2010 | Wang et al. | |
| 2010/0166842 A1 | 7/2010 | Lu et al. | |
| 2011/0123982 A1 | 5/2011 | Lu et al. | |
| 2011/0171635 A1 | 7/2011 | Lu et al. | |

FOREIGN PATENT DOCUMENTS

| | | |
|---|---|---|
| EP | 1 312 674 | 5/2003 |
| GB | 2339280 | 1/2000 |
| WO | WO 91/14696 | 10/1991 |
| WO | WO 96/17086 | 6/1996 |
| WO | WO 97/09342 | 3/1997 |
| WO | WO 98/04740 | 2/1998 |
| WO | WO 98/27104 | 6/1998 |
| WO | WO 98/39484 | 9/1998 |
| WO | WO 98/49346 | 11/1998 |
| WO | WO 99/13338 | 3/1999 |
| WO | WO 99/27351 | 6/1999 |
| WO | WO 99/47704 | 9/1999 |
| WO | WO 00/26226 | 5/2000 |
| WO | WO 00/58505 | 10/2000 |
| WO | WO 01/00876 | 1/2001 |
| WO | WO 01/23548 | 4/2001 |
| WO | WO 01/24696 | 4/2001 |
| WO | WO 01/27612 A2 | 4/2001 |
| WO | WO 01/27612 A3 | 4/2001 |
| WO | WO 01/51665 | 7/2001 |
| WO | WO 01/73123 | 10/2001 |
| WO | WO 02/00006 | 1/2002 |
| WO | WO 02/22882 | 3/2002 |
| WO | WO 02/098364 | 12/2002 |
| WO | WO 03/062422 | 7/2003 |
| WO | WO 03/068963 | 8/2003 |
| WO | WO 03/094838 | 11/2003 |
| WO | WO 03/095648 | 11/2003 |
| WO | WO 2004/046687 | 6/2004 |
| WO | WO 2004/081235 | 9/2004 |
| WO | WO 2005/082922 | 9/2005 |
| WO | WO 2005/095967 | 10/2005 |
| WO | WO 2005/100602 | 10/2005 |
| WO | WO 2006/020768 | 2/2006 |
| WO | WO 2006/020786 | 2/2006 |
| WO | WO 2006/048164 | 5/2006 |
| WO | WO 2006/052419 | 5/2006 |
| WO | WO 2006/078660 | 7/2006 |
| WO | WO 2007/106118 | 9/2007 |
| WO | WO 2007/109500 | 9/2007 |
| WO | WO 2008/089248 | 7/2008 |
| WO | WO 2009/012309 | 1/2009 |
| WO | WO 2009/045632 | 4/2009 |

OTHER PUBLICATIONS

Bannon, D.I., et al., "Graphite furnace atomic absorption spectroscopic measurement of blood lead in matrix-matched standards", Clinical Chemistry, vol. 40, No. 9, pp. 1730-1734, (1994).

Been, M.D., et al., "Self-cleaving ribozymes of hepatitis delta virus RNA", Eur. J. Biochem., vol. 247, pp. 741-753, (1997).

Berens, C., et al., "A tetracycline-binding RNA aptamer", Bioorganic & Medicinal Chemistry, vol. 9, pp. 2549-2556, (2001).

Biroccio, A., et al., "Selection of RNA aptamers that are specific and high-affinity ligands of the hepatitis C virus RNA-dependent RNA polymerase", Journal of Virology, vol. 76, No. 8, pp. 3688-3696, (2002).

Blake, D.A., et al., "Antibody-based sensors for heavy metal ions", Biosensors & Bioelectronics, vol. 16, pp. 799-809, (2001).

Blank, M., et al., "Systematic evolution of a DNA aptamer binding to rat brain tumor microvessels. Selective targeting of endothelial regulatory protein pigpen", Journal of Biological Chemistry, vol. 276, No. 19, pp. 16464-16468, (2001).

Bock, L.C., et al., "Selection of single-stranded DNA molecules that bind and inhibit human thrombin", Nature, vol. 355, pp. 564-566, (1992).

Bogden, J.D., et al., "Soil contamination from lead in paint chips", Bulletin of Environmental Contamination & Toxicology, vol. 14, No. 3, pp. 289-294, (1975).

Boiziau, C., et al., "DNA aptamers selected against the HIV-1 trans-activation-responsive RNA element form RNA-DNA kissing complexes", Journal of Biological Chemistry, vol. 274, No. 18, pp. 12730-12737, (1999).

Bowins, R.J., et al., "Electrothermal isotope dilution inductively coupled plasma mass spectrometry method for the determination of sub-ng $ml^{-1}$ levels of lead in human plasma", Journal of Analytical Atomic Spectrometry, vol. 9, pp. 1233-1236, (1994).

Breaker, R.R., "Catalytic DNA: in training and seeking employment", Nature Biotechnology, vol. 17, pp. 422-423, (1999).

Breaker, R.R., "DNA aptamers and DNA enzymes" Current Opinion in Chemical Biology, vol. 1, pp. 26-31, (1997).

Breaker, R.R., "DNA enzymes", Nature Biotechnology, vol. 15, pp. 427-431, (1997).

Breaker, R.R., "Molecular Biology: Making Catalytic DNAs", Science, vol. 290, issue 5499, pp. 2095-2096, (2000).

Breaker, R.R., et al., "A DNA enzyme that cleaves RNA", Chemistry & Biology, vol. 1, No. 4, pp. 223-229, (1994).

Breaker, R.R., et al., "A DNA enzyme with $Mg^{2+}$-dependent RNA phosphoesterase activity", Chemistry & Biology, vol. 2, No. 10, pp. 655-660, (1995).

Breaker, R.R., et al., "Engineered allosteric ribozymes as biosensor components", Current Opinion in Biotechnology, vol. 13, pp. 31-39, (2002).

Brody, E.N., et al., "Aptamers as therapeutic and diagnostic agents", Reviews in Molecular Biotechnology, vol. 74, pp. 5-13, (2000).

Broude, N.E., "Stem-loop oligonucleotides: a robust tool for molecular biology and biotechnology", Trends in Biotechnology, vol. 20, No. 6, pp. 249-256, (2002).

Brown, A.K., et al., "A lead-dependent DNAzyme with a two-step mechanism", Biochemistry, vol. 42, No. 23, pp. 7152-7161, (2003).

Bruesehoff, P.J., et al., "Improving metal ion specificity during In Vitro selection of catalytic DNA", Combinatorial Chemistry & High Throughput Screening, vol. 5, pp. 327-335, (2002).

Bruno, J.G., et al., "In vitro selection of DNA aptamers to anthrax spores with electrochemiluminescence detection", Biosensors & Bioelectronics, vol. 14, pp. 457-464, (1999).

Bruno, J.G., et al., "Use of magnetic beads in selection and detection of biotoxin aptamers by electrochemiluminescence and enzymatic methods", BioTechniques, vol. 32, No. 1, pp. 178-180, pp. 182-183, (2002).

Brust, M., et al., "Novel gold-dithiol nano-networks with non-metallic electronic properties", Advanced Materials, vol. 7, No. 9, pp. 795-797, (1995).

Burdette, S.C., et al., "Fluorescent Sensor for $Zn^{2+}$ Based on a Fluorescein Platform: Synthesis, Properties and Intracellular Distribution", J. Am. Chem. Soc., vol. 123, No. 32, pp. 7831-7841, (2001).
Burgstaller, P., et al., "Isolation of RNA aptamers for biological cofactors by in vitro selection", Angew. Chem. Int. Ed. Engl, vol. 33, No. 10, pp. 1084-1087, (1994).
Burgstaller, P., et al., "Structural probing and damage selection of citrulline- and arginine-specific RNA aptamers identify base positions required for binding", Nucleic Acids Research, vol. 23, No. 23, pp. 4769-4776, (1995).
Burke, D.H., et al., "A Novel Acidophilic RNA Motif That Recognizes Coenzyme A", Biochemistry, vol. 37, No. 13, pp. 4653-4663, (1998).
Burke, D.H., et al., "RNA aptamers to the adenosine moiety of S-adenosyl methionine: structural inferences from variations on a theme and the reproducibility of SELEX", Nucleic Acids Research, vol. 25, No. 10, pp. 2020-2024, (1997).
Burke, D.H., et al., "RNA aptamers to the peptidyl transferase inhibitor chloramphenicol", Chemistry & Biology, vol. 4, No. 11, pp. 833-843, (1997).
Burmeister, J., et al., "Cofactor-assisted self-cleavage in DNA libraries with a 3'-5'-phosphoramidate bond", Angew. Chem. Int. Ed. Engl., vol. 36, No. 12, pp. 1321-1324, (1997).
Burwell Jr., R.L., "Modified silica gels as adsorbents and catalysts", Chemical Technology, 4, pp. 370-377, (1974).
Cadwell, R.C., et al., "Mutagenic PCR", PCR Methods and Applications, vol. 3, pp. S136-S140, (1994).
Cadwell, R.C., et al., "Randomization of genes by PCR mutagenesis", PCR Methods and Applications, vol. 2, pp. 28-33, (1992).
Cake, K.M., et al., "In vivo x-ray fluorescence of bone lead in the study of human lead metabolism: serum lead, whole blood lead, bone lead, and cumulative exposure", Advances in X-Ray Analysis, vol. 38, pp. 601-606, (1995).
Camara Rica, C., et al., "Determination of trace concentrations of lead and nickel in human milk by electrothermal atomisation atomic absorption spectrophotometry and inductively coupled plasma emission spectroscopy", The Science of the Total Environment, vol. 22, pp. 193-201, (1982).
Cao, Y.W., et al., "DNA-modified core-shell Ag/Au nanoparticles", J. Am. Chem. Soc., vol. 123, No. 32, pp. 7961-7962, (2001).
Carmi, N., et al., "Cleaving DNA with DNA", Proc. Natl. Acad. Sci. USA, vol. 95, pp. 2233-2237, (1998).
Carmi, N., et al., "In vitro selection of self-cleaving DNAs", Chemistry & Biology, vol. 3, No. 12, pp. 1039-1046, (1996).
Cech, T.R., "Structure and mechanism of the large catalytic RNAs: group I and group II introns and ribonuclease P", The RNA World, pp. 239-269, Cold Spring Harbor Laboratory Press, Cold Spring Harbor, New York, (1993).
Cech, T.R., et al., "Group I ribozymes: substrate recognition, catalytic strategies, and comparative mechanistic analysis", Nucleic Acids and Molecular Biology, vol. 10, pp. 1-17, (1996).
Chaloin, L., et al., "Endogenous expression of a high-affinity pseudoknot RNA aptamer suppresses replication of HIV-1", Nucleic Acids Research, vol. 30, No. 18, pp. 4001-4008, (2002).
Chapman, K.B., et al., "In vitro selection of catalytic RNAs", Current Opinion in Structural Biology, vol. 4, pp. 618-622, (1994).
Chartrand, P., et al., "Effect of structural modifications on the activity of the leadzyme", Biochemistry, vol. 36, No. 11, pp. 3145-3150, (1997).
Chen, J., et al., "Synthesis from DNA of a molecule with the connectivity of a cube", Nature, vol. 350, pp. 631-633, (1991).
Chen, C-T., et al., "A highly selective fluorescent chemosensor for lead ions", J. Am. Chem. Soc., vol. 124, pp. 6246-6247, (2002).
Chen, J-H., et al., "A specific quadrilateral synthesized from DNA branched junctions", J. Am. Chem. Soc., vol. 111, No. 16, pp. 6402-6407, (1989).
Chen, L., et al., "Crystal structure of a four-stranded intercalated DNA: $d(C_4)$", Biochemistry, vol. 33, No. 46, pp. 13540-13546, (1994).
Chinnapen, D.J.F., et al., "Hemin-stimulated docking of cytochrome c to a hemin-DNA aptamer complex", Biochemistry, vol. 41, No. 16, pp. 5202-5212, (2002).
Ciesiolka, J., et al., "Selection of an RNA domain that binds $Zn^{2+}$", RNA, vol. 1, pp. 538-550, (1995).
Ciesiolka, J., et al., "Small RNA-divalent domains", RNA, vol. 2, pp. 785-793, (1996).
Conaty, J., et al., "Selected classes of minimised hammerhead ribozyme have very high cleavage rates at low $Mg^{2+}$ concentration", Nucleic Acids Research, vol. 27, No. 11, pp. 2400-2407, (1999).
Conn, M.M., et al., "Porphyrin Metalation Catalyzed by a Small RNA Molecule", J. Am. Chem. Soc, vol. 118, No. 29, pp. 7012-7013, (1996).
Connell, G.J., et al., "RNAs with dual specificity and dual RNAs with similar specificity", Science, New Series, vol. 264, issue 5162, pp. 1137-1141, (1994).
Connell, G.J., et al., "Three small ribooligonucleotides with specific arginine sites", Biochemistry, vol. 32, No. 21, pp. 5497-5502, (1993).
Cuenoud, B., et al., "A DNA metalloenzyme with DNA ligase activity", Nature, vol. 375, pp. 611-614, (1995).
Czarnik, A.W., "Desperately seeking sensors", Chemistry & Biology, vol. 2, No. 7, pp. 423-428, (1995).
Dai, X., et al., "Cleavage of an amide bond by a ribozyme", Science, New Series, vol. 267, issue 5195, pp. 237-240, (1995).
Davis, J.H., et al., "Isolation of high-affinity GTP aptamers from partially structured RNA libraries", Proc. Natl. Acad. Sci. USA, vol. 99, No. 18, pp. 11616-11621, (2002).
Davis, K.A., et al., "Staining of cell surface human CD4 with 2'-F-pyrimidine-containing RNA aptamers for flow cytometry", Nucleic Acids Research, vol. 26, No. 17, pp. 3915-3924, (1998).
Definition of the word "ion" printed from Merriam-Webster online dictionary (www.m-w.com) on Jun. 30, 2004.
Definition of the word "particle" printed from Merriam-Webster online dictionary (www.m-w.com) on Jun. 29, 2004.
Deo, S., et al., "A Selective, Ratiometric Fluorescent Sensor for $Pb^{2+}$", J. Am. Chem. Soc., vol. 122, No. 1, pp. 174-175, (2000).
Derose, V.J., "Two Decades of RNA Catalysis", Chemistry & Biology, vol. 9, pp. 961-969, (2002).
Didenko, V.V., "DNA probes using fluorescence resonance energy transfer (FRET): Designs and applications", BioTechniques, vol. 31, pp. 1106-1121, (2001).
Doudna, J.A., et al., "The Chemical Repertoire of Natural Ribozymes", Nature, vol. 418, pp. 222-228, (2002).
Dubois, L.H., et al., "Synthesis, structure, and properties of model organic surfaces", Annu. Rev. Phys. Chem., vol. 43, pp. 437-463, (1992).
Earnshaw, D.J., et al., "Modified oligoribonucleotides as site-specific probes of RNA structure and function", Biopolymers (Nucleic Acid Sciences), vol. 48, pp. 39-55, (1998).
Ekland, E.H., et al., "RNA-catalysed RNA polymerization using nucleoside triphosphates", Nature, vol. 382, pp. 373-376, (1996).
Ekland, E.H., et al., "Structurally complex and highly active RNA ligases derived from random RNA sequences", Science, vol. 269, issue 5222, pp. 364-370, (1995).
Elghanian, R., et al., "Selective colorimetric detection of polynucleotides based on the distance-dependent optical properties of gold nanoparticles", Science, vol. 277, pp. 1078-1081, (1997).
Ellington, A.D., et al., "Aptamers as potential nucleic acid pharmaceuticals", Biotechnology Annual Review, vol. 1, pp. 185-214, (1995).
Ellington, A.D., et al., "In vitro selection of RNA molecules that bind specific ligands", Nature, vol. 346, pp. 818-822, (1990).
Ellington, A.D., et al., "Selection in vitro of single-stranded DNA molecules that fold into specific ligand-binding structures", Nature, vol. 355, pp. 850-852, (1992).
Famulok, M., "Molecular Recognition of Amino Acids by RNA-Aptamers: An L-Citrulline Binding RNA Motif and Its Evolution into an L-Arginine Binder", J. Am. Chem. Soc., vol. 116, No. 5, pp. 1698-1706, (1994).
Famulok, M., "Oligonucleotide aptamers that recognize small molecules", Current Opinion in Structural Biology, vol. 9, pp. 324-329, (1999).
Famulok, M., et al., "In Vitro Selection Analysis of Neomycin Binding RNAs with a Mutagenized Pool of Variants of the 16S rRNA Decoding Region", Biochemistry, vol. 35, No. 14, pp. 4265-4270, (1996).

Famulok, M., et al., "Stereospecific recognition of tryptophan agarose by in vitro selected RNA", J. Am. Chem. Soc., vol. 114, No. 10, pp. 3990-3991, (1992).

Faulhammer, D., et al., "Characterization and Divalent Metal-ion Dependence of in Vitro Selected Deoxyribozymes which Cleave DNA/RNA Chimeric Oligonucleotides", J. Mol. Biol., vol. 269, pp. 188-202, (1997).

Faulhammer, D., et al., "The $Ca^{2+}$ cofactor for a novel RNA-cleaving deoxyribozyme", Angew. Chem., Int. Ed. Engl., vol. 35, No. 23/24, pp. 2837-2841, (1996).

Feldman, B.J., et al., "Determination of lead in blood by square wave anodic stripping voltammetry at a carbon disk ultramicroelectrode", Analytical Chemistry, vol. 66, No. 13, pp. 1983-1987, (1994).

Ferguson, A., et al., "A novel strategy for selection of allosteric ribozymes yields riboreporter™ sensors for caffeine and aspartame", Nucleic Acids Research, vol. 32, No. 5, pp. 1756-1766, (2004).

Fodor, S.P.A., et al., "Light-directed, spatially addressable parallel chemical synthesis", Science, New Series, vol. 251, issue 4995, pp. 767-773, (1991).

Frank, D.N., et al., "In vitro selection for altered divalent metal specificity in the RNase P RNA", Proc. Natl. Acad. Sci. USA, vol. 94, pp. 14355-14360, (1997).

Frens, G., et al., "Controlled Nucleation for the regulation of the particle size in monodisperse gold suspensions", Nature Physical Science, vol. 241, pp. 20-22, (1973).

Fukusaki, E-I., et al., "DNA aptamers that bind to chitin", Bioorganic & Medicinal Chemistry letters, vol. 10, pp. 423-425, (2000).

Geiger, A., et al., "RNA aptamers that bind L-arginine with sub-micromolar dissociation constants and high enantioselectivity", Nucleic Acids Research, vol. 24, No. 6, pp. 1029-1036, (1996).

Geyer, C.R., et al., "Evidence for the metal-cofactor independence of an RNA phosphodiester-cleaving DNA enzyme", Chemistry & Biology, vol. 4, No. 8, pp. 579-593, (1997).

Geyer, C.R., et al., "Lanthanide Probes for a Phosphodiester-cleaving, Lead-dependent, DNAzyme", J. Mol. Biol., vol. 275, pp. 483-489, (1998).

Giver, L., et al., "Selection and design of high-affinity RNA ligands for HIV-1 Rev", Gene, vol. 137, pp. 19-24, (1993).

Giver, L., et al., "Selective optimization of the Rev-binding element of HIV-1",Nucleic Acids Research, vol. 21, No. 23, pp. 5509-5516, (1993).

Godwin, H.A., et al., "A Flourescent Zinc Probe Based on Metal-Induced Peptide Folding", J. Am. Chem. Soc., vol. 118, pp. 6514-6515, (1996).

Grabar, K., et al., "Preparation and characterization of Au colloid Monolayers", Analytical chemistry, vol. 67, No. 4, pp. 735-743, (1995).

Granadillo, V.A., et al., "The influence of the blood levels of lead, aluminum and vanadium upon the arterial hypertension", Clinica Chimica Acta, vol. 233, pp. 47-59, (1995).

Grate, D., et al., "Laser-mediated, site-specific inactivation of RNA transcripts", Proc. Natl. Acad. Sci. USA, vol. 96, pp. 6131-6136, (1999).

Guschin, D., et al., "Manual manufacturing of oligonucleotide, DNA, and protein microchips", Analytical Biochemistry, vol. 250, pp. 203-211, (1997).

Haller, A.A., et al., "In vitro selection of a 7-methyl-guanosine binding RNA that inhibits translation of capped mRNA molecules", Proc. Natl. Acad. Sci. USA, vol. 94, pp. 8521-8526, (1997).

Harada, K., et al., "Identification of two novel arginine binding DNAs", The EMBO Journal, vol. 14, No. 23, pp. 5798-5811, (1995).

Hartig, J.S., et al., "Reporter ribozymes for real-time analysis of domain-specific interactions in biomolecules: HIV-1 reverse transcriptase and the primer-template complex", Angew. Chem. Int. Ed., vol. 41, No. 22, pp. 4263-4266, (2002).

He, X-x., et al., "Bioconjugated nanoparticles for DNA protection from cleavage", J. Am. Chem. Soc., vol. 125, No. 24, pp. 7168-7169, (2003).

Hennrich, G., et al., "Redox switchable fluorescent probe selective for either Hg(II) or Cd(II) and Zn(II)" J. Am. Chem. Soc., vol. 121, No. 21, pp. 5073-5074, (1999).

Hesselberth, J., et al., "In vitro selection of nucleic acids for diagnostic applications", Reviews in Molecular Biotechnology, vol. 74, pp. 15-25, (2000).

Hesselberth, J.R., et al., "Simultaneous detection of diverse analytes with an aptazyme ligase array", Analytical Biochemistry vol. 312, pp. 106-112, (2003).

Ho, H-A., et al., "Optical sensors based on hybrid aptamer/conjugated polymer complexes", J. Am. Chem. Soc., vol. 126, No. 5, pp. 1384-1387, (2004).

Hock, B., "Antibodies for immunosensors, A review", Analytica Chimica Acta, vol. 347, pp. 177-186, (1997).

Hofmann, H.P., et al., "$Ni^{2+}$-binding RNA motifs with an asymmetric purine-rich internal loop and a G-A base pair", RNA, vol. 3, pp. 1289-1300, (1997).

Holeman, L.A., et al., "Isolation and characterization of fluorophore-binding RNA aptamers", Folding & Design, vol. 3, pp. 423-431, (1998).

Hoogstraten, C.G., et al., "NMR solution structure of the lead-dependent ribozyme: Evidence for dynamics in RNA catalysis", J. Mol. Biol., vol. 284, pp. 337-350, (1998).

Hoogstraten, C.G., et al., "Structural analysis of metal ion ligation to nucleotides and nucleic acids using pulsed EPR spectroscopy", J. Am. Chem. Soc., vol. 124, No. 5, pp. 834-842, (2002).

Huizenga, D.E., et al., "A DNA aptamer that binds adenosine and ATP", Biochemistry, vol. 34, No. 2, pp. 656-665, (1995).

Iler, R.K., "The Chemistry of Silica: Solubility, Polymerization, Colloid and Surface Properties, and Biochemistry, Chapter 6, The surface chemistry of silica", pp. 622-729, A Wiley-Interscience Publication, New York, (1979).

Illangasekare, M., et al., "Small-molecule-substrate interactions with a self-aminoacylating ribozyme", J. Mol. Biol., vol. 268, pp. 631-639, (1997).

Imperiali, B., et al., "Peptide platforms for metal ion sensing", Proc. SPIE—The international society for optical engineering, vol. 3858, pp. 135-143, (1999).

International Search Report dated Jan. 15, 2003 for PCT application No. PCT/US01/20557.

International Search Report dated Aug. 1, 2003 for PCT application No. PCT/US03/08483.

Iqbal, S.S., et al., "A review of molecular recognition technologies for detection of biological threat agents", Biosensors & Bioelectronics, vol. 15, pp. 549-578, (2000).

Abstract of: Iwasaki, K., Mizota, T., Kenkyu Hokoku—Kanagawa-ken Kogyo Shikensho 1991, 62, 57.

Jagner, D., et al., "Determination of lead in microliter amounts of whole blood by stripping potentiometry", Electroanalysis, vol. 6, pp. 285-291, (1994).

Jayasena, S.D., "Aptamers: an emerging class of molecules that rival antibodies in diagnostics", Clinical Chemistry, vol. 45, No. 9, pp. 1628-1650, (1999).

Jenison, R., et al., "Interference-based detection of nucleic acid targets on optically coated silicon", Nature Biotechnology, vol. 19, pp. 62-65, (2001).

Jenison, R.D., et al., "High-resolution molecular discrimination by RNA", Science, vol. 263, pp. 1425-1429, (1994).

Jenne, A., et al., "Rapid Identification and Characterization of Hammerhead-Ribozyme Inhibitors Using Fluorescence-Based Technology", Nature Biotechnology, vol. 19, pp. 56-61, (2001).

Jenne, A., et al., "Real-time Characterization of Ribozymes by Fluorescence Resonance Energy Transfer (FRET)", Angewandte Chemie. International Edition, vol. 38, No. 9, pp. 1300-1303, (1999).

Jhaveri, S., et al., "In vitro selection of signaling aptamers", Nature Biotechnology, vol. 18, pp. 1293-1297, (2000).

Jhaveri, S.D., et al., "Designed signaling aptamers that transduce molecular recognition to changes in fluorescence intensity", J. Am. Chem. Soc., vol. 122, No. 11, pp. 2469-2473, (2000).

Jin, R., et al., "What controls the melting properties of DNA-linked gold nanoparticle assemblies?", J. Am. Chem. Soc., vol. 125, No. 6, pp. 1643-1654, (2003).

Joos, B., et al., "Covalent attachment of hybridizable oligonucleotides to glass supports", Analytical Biochemistry, vol. 247, pp. 96-101, (1997).

Josephson, L., et al., "Magnetic nanosensors for the detection of oligonucleotide sequences", Angewandte Chemie. International Edition, vol. 40, No. 17, pp. 3204-3206, (2001).

Joyce, G.F., "Appendix 3: Reactions Catalyzed by RNA and DNA Enzymes". The RNA World, vol. 37, pp. 687-690, Cold Spring Harbor Laboratory Press, Cold Spring Harbor, New York, (1999).

Joyce, G.F., "In vitro evolution of nucleic acids", Current Opinion in Structural Biology, vol. 4, pp. 331-336, (1994).

Katahira, M., et al., "Two metal-binding sites in a lead ribozyme bound to competitively by $Pb^{2+}$ and $Mg^{2+}$: Induced structural changes as revealed by NMR", European Journal of Biochemistry, vol. 255, pp. 727-733, (1998).

Kato, T., et al., "In vitro selection of DNA aptamers which bind to cholic acid", Biochimica et Biophysica Acta, vol. 1493, pp. 12-18, (2000).

Kawakami, J., et al., "In vitro selection of aptamers that act with $Zn^{2+}$", Journal of Inorganic Biochemistry, vol. 82, pp. 197-206, (2000).

Khan, R., et al., "Interaction of retroviral nucleocapsid proteins with transfer $RNA^{Phe}$: a lead ribozyme and $^1H$ NMR study", Nucleic Acids Research, vol. 24, No. 18, pp. 3568-3575, (1996).

Khosraviani, M., et al., "Detection of heavy metals by immunoassay: Optimization and validation of a rapid, portable assay for ionic cadmium", Environ. Sci. Technol., vol. 32, No. 1, pp. 137-142, (1998).

Kiga, D., et al., "An RNA aptamer to the xanthine/guanine base with a distinctive mode of purine recognition", Nucleic Acids Research, vol. 26, No. 7, pp. 1755-1760, (1998).

Kim, M.H., et al., "Activation and repression of the activity of a lead ribozyme by the combination of $Pb^{2+}$ and $Mg^{2+1}$", J. Biochem., vol. 122, No. 5, pp. 1062-1067, (1997).

Klußmann, S., et al., "Mirror-image RNA that binds D-adenosine", Nature Biotechnology, vol. 14, pp. 1112-1115, (1996).

Kohama, T., et al., "Molecular Cloning and Functional Characterization of Murine Sphingosine Kinase", The Journal of Biological Chemistry, vol. 273, No. 37, pp. 23722-23728, (1998).

Koizumi, M., et al., "Allosteric selection of ribozymes that respond to the second messengers cGMP and cAMP", Nature Structural Biology, vol. 6, No. 11, pp. 1062-1071, (1999).

Koizumi, M., et al., "Molecular Recognition of cAMP by an RNA Aptamer", Biochemistry, vol. 39, No. 30, pp. 8983-8992, (2000).

Koizumi, M., et al., "Allosteric ribozymes sensitive to the second messengers cAMP and cGMP", Nucleic Acids Symposium Series, No. 42, pp. 275-276, (1999).

Kruger, K., et al., "Self-splicing RNA: autoexcision and autocyclization of the ribosomal RNA intervening sequence of the Tetrahymena", Cell, vol. 31, pp. 147-157, (1982).

Lato, S.M., et al., "In vitro selection of RNA lectins: Using combinatorial chemistry to interpret ribozyme evolution", Chemistry & Biology, vol. 2, No. 5, pp. 291-303, (1995).

Lauhon, C.T., et al., "RNA aptamers that bind flavin and nicotinamide redox cofactors", J. Am. Chem. Soc., vol. 117, No. 4, pp. 1246-1257, (1995).

Lebruska, L.L., "Selection and Characterization of an RNA Decoy for Transcription Factor NF-κB", Biochemistry, vol. 38, No. 10, pp. 3168-3174, (1999).

Lee, M., et al., "A fiber-optic microarray biosensor using aptamers as receptors", Analytical Biochemistry, vol. 282, pp. 142-146, (2000).

Lee, S-W., et al., "Ordering of quantum dots using genetically engineered viruses", Science, vol. 296, pp. 892-895, (2002).

Legault, P., et al., "Order, dynamics and metal-binding in the lead-dependent ribozyme", J. Mol. Biol., vol. 284, pp. 325-335, (1998).

Lehman, N., et al., "Evolution in vitro of an RNA enzyme with altered metal dependence", Nature, vol. 361, pp. 182-185, (1993).

Lemieux, S., et al., "Modeling active RNA structures using the intersection of conformational space: application to the lead-activated ribozyme", RNA, vol. 4, pp. 739-749, (1998).

Levy, M., et al., "ATP-Dependent Allosteric DNA Enzymes", Chemistry & Biology, vol. 9, pp. 417-426, (2002).

Li, J., et al., "A highly sensitive and selective catalytic DNA biosensor for lead ions", J. Am. Chem. Soc., vol. 122, No. 42, pp. 10466-10467, (2000).

Li, J., et al., "In vitro selection and characterization of a highly efficient Zn(II)-dependent RNA-cleaving deoxyribozyme", Nucleic Acids Research, vol. 28, No. 2, pp. 481-488, (2000).

Li, J.J., et al., "Using molecular beacons as a sensitive fluorescence assay for enzymatic cleavage of single-stranded DNA", Nucleic Acids Research, vol. 28, No. 11, e52, pp. i-vi, (2000).

Li, Y., et al., "A catalytic DNA for porphyrin metallation", Nature Structural Biology, vol. 3, No. 9, pp. 743-747, (1996).

Li, Y., et al., "Capping DNA with DNA", Biochemistry, vol. 19, No. 11, pp. 3106-3114, (2000).

Li, Y., et al., "Deoxyribozymes: new players in the ancient game of biocatalysis", Current Opinion in Structural Biology, vol. 9, pp. 315-323, (1999).

Li, Y., et al., "Phosphorylating DNA with DNA", Proc. Natl. Acad. Sci. USA, vol. 96, pp. 2746-2751, (1999).

Link, S., et al., "Alloy formation of gold-silver nanoparticles and the dependence of the plasmon absorption on their composition", J. Phys. Chem. B, vol. 103, No. 18, pp. 3529-3533, (1999).

Liu, H-W., et al., "Determination of cadmium, mercury and lead in seawater by electrothermal vaporization isotope dilution inductively coupled plasma mass spectrometry", Spectrochimica Acta Part B Atomic Spectroscopy 54, pp. 1367-1375, (1999).

Liu, J., et al., "A colorimetric lead biosensor using DNAzyme-directed assembly of gold nanoparticles", J. Am. Chem. Soc., vol. 125, No. 22, pp. 6642-6643, (2003).

Liu, J., et al., "Accelerated color change of gold nanoparticles assembled by DNAzymes for simple and fast colorimetric $Pb^{2+}$ detection", J. Am. Chem. Soc., vol. 126, No. 39, pp. 12298-12305, (2004).

Liu, J., et al., "Adenosine-dependent assembly of aptazyme-functionalized gold nanoparticles and its application as a colorimetric biosensor", Analytical Chemistry, vol. 76, No. 6, pp. 1627-1632, (2004).

Liu, J., et al., "Colorimetric biosensors based on DNAzyme-assembled gold nanoparticles", Journal of Fluorescence, vol. 14, No. 4, pp. 343-354, (2004).

Liu, J., et al., "Highly dispersible molecular sieve carbon nanoparticles", Chem. Mater., vol. 16, No. 22, pp. 4205-4207, (2004).

Liu, X., et al., "A fiber-optic evanescent wave DNA biosensor based on novel molecular beacons", Analytical Chemistry, vol. 71, No. 22, pp. 5054-5059, (1999).

Liu, Z., et al., "Assemblage of signaling DNA enzymes with intriguing metal-ion specificities and pH dependences", J. Am. Chem. Soc., vol. 125, No. 25, pp. 7539-7545, (2003).

Lohse, P.A., et al., "Ribozyme-catalysed amino-acid transfer reactions", Nature, vol. 381, pp. 442-444, (1996).

Lorsch, J.R., et al., "In vitro evolution of new ribozymes with polynucleotide kinase activity", Nature, vol. 371, pp. 31-36, (1994).

Lorsch, J.R., et at "In vitro selection of RNA aptamers specific for cyanocobalamin", Biochemistry, vol. 33, No. 4, pp. 973-982, (1994).

Lott, W.B., et al., "A two-metal ion mechanism operates in the hammerhead ribozyme-mediated cleavage of an RNA substrate", Proc. Natl. Acad. Sci. USA, vol. 95, pp. 542-547, (1998).

Lu, Y., "New transition-metal-dependent DNAzymes as efficient endonucleases and as selective metal biosensors", Chem. Eur. J., vol. 8, No. 20, pp. 4588-4596, (2002).

Lu, Y., et al., "New fluorescent and colorimetric DNAzyme biosensors for metal ions", Journal of Inorganic Biochemistry, vol. 96, issue 1, pp. 30, Abstract of the 11th International Conference on Biological Inorganic Chemistry; (Jul. 15, 2003).

Majerfeld, I., et al., "An RNA pocket for an aliphatic hydrophobe", Structural Biology, vol. 1, No. 5, pp. 287-292, (1994).

Majerfeld, I., et al., "Isoleucine:RNA sites with associated coding sequences", RNA, vol. 4, pp. 471-478, (1998).

Mannironi, C., et al., "In vitro selection of dopamine RNA ligands", Biochemistry, vol. 36, No. 32, pp. 9726-9734, (1997).

Maoz, R., et al., "Penetration-controlled reactions in organized monolayer assemblies. 1. Aqueous permanganate interaction with monolayer and multilayer films of long-chain surfactants", Langmuir, vol. 3, No. 6, pp. 1034-1044, (1987).

Marcus, A.H., et al., "Estimating the contribution of lead based paint to soil lead, dust lead, and childhood blood lead", American Society for Testing and Materials Spec. STP 1226, pp. 12-23, (1995).

Marsh, T.C., et al., "A new DNA nanostructure, the G-wire, imaged by scanning probe microscopy", Nucleic Acids Research, vol. 23, No. 4, pp. 696-700, (1995).

Matteucci, M.D., et al., "Synthesis of Deoxyoligonucleotides on a polymer support", J. Am. Chem. Soc., vol. 103, No. 11, pp. 3185-3191, (1981).

Mecklenburg, M., et al., "A strategy for the broad range detection of compounds with affinity for nucleic acids", Analytica Chimica Acta, vol. 347, pp. 79-86, (1997).

Mei, S.H.J., et al., "An efficient RNA-cleaving DNA enzyme that synchronizes catalysis with fluorescence signaling", J. Am. Chem. Soc., vol. 125, No. 2, pp. 412-420, (2003).

Meli, M., et al., "Adenine-aptamer complexes: A bipartite RNA site that binds the adenine nucleic base", The Journal of Biological Chemistry, vol. 277, No. 3, pp. 2104-2111, (2002).

Mirkin, C.A., et al., "A DNA-based method for rationally assembling nanoparticles into macroscopic materials", Nature, vol. 382, pp. 607-609, (1996).

Mirkin, S.M., et al., "H-DNA and related structures", Annu. Rev. Biophys. Biomol. Struct., vol. 23, pp. 541-576, (1994).

Miyawaki, A., et al. "Fluorescent indicators for $Ca^{2+}$ based on green fluorescent proteins and calmodulin", Nature, vol. 388, pp. 882-887, (1997).

Mucic, R.C., et al., "Synthesis and characterization of DNA with ferrocenyl groups attached to their 5'-termini: electrochemical characterization of a redox-active nucleotide monolayer", Chem. Commun., pp. 555-557, (1996).

Mullah, B., et al., "Automated synthesis of double dye-labeled oligonucleotides using tetramethylrhodamine (TAMRA) solid supports", Tetrahedron Letters, vol. 38, No. 33, pp. 5751-5754, (1997).

Nazarenko, I.A., et al., "A closed tube format for amplification and detection of DNA based on energy transfer", Nucleic Acids Research, vol. 26, No. 12, pp. 2516-2521, (1997).

Nazarenko, I.A., et al., "Defining a Smaller RNA Substrate for Elongation Factor Tu", Biochemistry, vol. 34, No. 8, pp. 2545-2552, (1995).

Niemeyer, C.M., "Nanoparticles, proteins, and nucleic acids: Biotechnology meets materials science", Angew. Chem. Int. Edition, vol. 40, pp. 4128-4158, (2001).

Nieuwlandt, D., et al., "In Vitro Selection of RNA Ligands to Substance P", Biochemistry, vol. 34, No. 16, pp. 5651-5659, (1995).

Nissen, P., et al., "The structural basis of ribosome activity in peptide bond synthesis", Science, vol. 289, pp. 920-930, (2000).

Nolte, A., et al., "Mirror-design of L-oligonucleotide ligands binding to L-arginine", Nature Biotechnology, vol. 14, pp. 1116-1119, (1996).

Nutiu, R., et al., "Structure-switching signaling aptamers", J. Am. Chem. Soc., vol. 125, No. 16, pp. 4771-4778, (2003).

Nuzzo, R.G., et al., "Spontaneously organized molecular assemblies. 3. Preparation and properties of solution adsorbed monolayers of organic disulfides on gold surfaces", J. Am. Chem. Soc., vol. 109, No. 8, pp. 2358-2368, (1987).

O'Donnell, M.J., et al., "High-Density, Covalent Attachment of DNA to Silicon Wafers for Analysis by MALDI-TOF Mass Spectrometry", Analytical Chemistry, vol. 69, No. 13, pp. 2438-2443, (1997).

Oehme, I., et al., "Optical sensors for determination of heavy metal ions", Mikrochim. Acta, vol. 126, pp. 177-192, (1997).

Ohmichi, T., et al., "Role of $Nd^{3+}$ and $Pb^{2+}$ on the RNA cleavage reaction by a small ribozyme", Biochemistry, vol. 36, No. 12, pp. 3514-3521, (1997).

Ohmichi, T., et al., "Effect of substrate RNA sequence on the cleavage reaction by a short ribozyme", Nucleic Acids Research, vol. 26, No. 24, pp. 5655-5661, (1998).

Okazawa, A., et al., "In vitro selection of hematoporphyrin binding DNA aptamers", Bioorganic & Medicinal Chemistry, Letters 10, pp. 2653-2656, (2000).

Ota, N., et al., "Effects of helical structures formed by the binding arms of DNAzymes and their substrates on catalytic activity", Nucleic Acids Research, vol. 26, No. 14, pp. 3385-3391, (1998).

Pan, T., et al., "A small metalloribozyme with a two-step mechanism", Nature, vol. 358, pp. 560-563, (1992).

Pan, T., et al., "In vitro selection of RNAs that undergo autolytic cleavage with $Pb^{2+}$", Biochemistry, vol. 31, No. 16, pp. 3887-3895, (1992).

Pan, T., et al., "Properties of an in vitro selected $Pb^{2+}$ cleavage motif", Biochemistry, vol. 33, No. 32, pp. 9561-9565, (1994).

Pan, W., et al., "Isolation of virus-neutralizing RNAs from a large pool of random sequences", Proc. Natl. Acad. Sci. USA, vol. 92, pp. 11509-11513, (1995).

Park, S-J., et al., "Array-based electrical detection of DNA with nanoparticle probes", Science, vol. 295, pp. 1503-1506, (2002).

Parsons, P.J., et al., "A rapid Zeeman graphite furnace atomic absorption spectrometric method for the determination of lead in blood", Spectrochimica Acta, vol. 48B, No. 6/7, pp. 925-939, (1993).

Pavlov, A.R., et al., "Determination of lead in environmental water samples by a rapid and portable immunoassay", ANYL, Book of Abstracts, 219th ACS National Meeting, San Francisco, CA, Mar. 26-30, 2000.

Pavlov, V., et al., "Aptamer-functionalized Au nanoparticles for the amplified optical detection of thrombin", J. Am. Chem. Soc., vol. 126, No. 38, pp. 11768-11769, (2004).

Pearce, D.A., et al., "Peptidyl chemosensors incorporating a FRET mechanism for detection of Ni(II)", Bioorganic & Medicinal Chemistry, Letters 8, pp. 1963-1968, (1998).

Pease, A.C., et al., "Light-generated oligonucleotide arrays for rapid DNA sequence analysis", Proc. Natl. Acad. Sci. USA, vol. 91, pp. 5022-5026, (1994).

Piccirilli, J.A., et al., "Aminoacyl esterase activity of the tetrahymena ribozyme", Science, New Series, vol. 256, issue 5062, pp. 1420-1424, (1992).

Pley, H.W., et al., "Three-dimensional structure of a hammerhead ribozyme", Nature, vol. 372, pp. 68-74, (1994).

Potyrailo, R.A., et al., "Adapting selected nucleic acid ligands (aptamers) to biosensors", Analytical Chemistry, vol. 70, No. 16, pp. 3419-3425, (1998).

Prudent, J.R., et al., "Expanding the scope of RNA catalysis", Science, New Series, vol. 264, issue 5167, pp. 1924-1927, (1994).

Qiao, H., et al., "Transferability of blood lead determinations by furnace atomic absorption spectrophotometry and continuum background correction", Clinical Chemistry, vol. 41, No. 10, pp. 1451-1454, (1995).

Rabinowitz, M., et al., "Home refinishing, lead paint, and infant blood lead levels", American Journal of Public Health, vol. 75, No. 4, pp. 403-404, (1985).

Rajendran, M., et al., "Selecting nucleic acids for biosensor applications", Combinatorial Chemistry and High Throughput Screening, vol. 5, No. 4, pp. 263-270, (2002).

Rakow, N.A., et al., "A colorimetric sensor array for odour visualization", Nature, vol. 406, pp. 710-713, (2000).

Rink, S.M., et al., "Creation of RNA molecules that recognize the oxidative lesion 7,8-dihydro-8-hydroxy-2'-deoxyguanosine (8-oxodG) in DNA", Proc. Natl. Acad. Sci. USA, vol. 95, pp. 11619-11624, (1998).

Robertson, M.P., et al., "Design and optimization of effector-activated ribozyme ligases", Nucleic Acids Research, vol. 28, No. 8, pp. 1751-1759, (2000).

Robertson, M.P., et al., "In vitro selection of an allosteric ribozyme that transduces analytes to amplicons", Nature Biotechnology, vol. 17, pp. 62-66, (1999).

Roth, A., et al., "An amino acid as a cofactor for a catalytic polynucleotide", Proc. Natl. Acad. Sci. USA, vol. 95, pp. 6027-6031, (1998).

Roychowdhury-Saha, M., et al., "Flavin Recognition by an RNA Aptamer Targeted toward FAD", Biochemistry, vol. 41, No. 8, pp. 2492-2499, (2002).

Ruckman, J., et al., "2'-Fluoropyrimidine RNA-based aptamers to the 165-amino acid form of vascular endothelial growth factor ($VEGF_{165}$) Inhibition of receptor binding and VEGF-induced vascular permeability through interactions requiring the exon 7-encoded domain", The Journal of Biological Chemistry, vol. 273, No. 32, pp. 20556-50567, (1998).

Rurack, K., et al., "A selective and sensitive fluoroionophore for Hg$^{II}$, Ag$^{I}$, and Cu$^{II}$ with virtually decoupled fluorophore and receptor units", J. Am. Chem. Soc., vol. 122, No. 5, pp. 968-969, (2000).

Rusconi, C.P., et al., "RNA aptamers as reversible antagonists of coagulation factor Ixa", Nature, vol. 419, pp. 90-94, (2002).

Sabanayagam, C.R., et al., "Oligonucleotide immobilization on micropatterened streptavidin surfaces", Nucleic Acids Research, vol. 28, No. 8, e33, pp. i-iv, (2000).

Santoro, S.W. et al., "Mechanism and utility of an RNA-cleaving DNA enzyme", Biochemistry, vol. 37, No. 38, pp. 13330-13342, (1998).

Santoro, S.W., et al., "A general purpose RNA-cleaving DNA enzyme", Proc. Natl. Acad. Sci. USA, vol. 94, pp. 4262-4266, (1997).

Santoro, S.W., et al., "RNA Cleavage by a DNA Enzyme with Extended Chemical Functionality", J. Am. Chem. Soc., vol. 122, No. 11, pp. 2433-2439, (2000).

Sassanfar, M., et al., "An RNA motif that binds ATP", Nature, vol. 364, pp. 550-553, (1993).

Schwartz, J., et al., "The risk of lead toxicity in homes with lead paint hazard", Environmental Research, vol. 54, No. 1, pp. 1-7, (1991).

Scott, W.G., et al., "The crystal structure of an all-RNA hammerhead ribozyme: A proposed mechanism for RNA catalytic cleavage", Cell, vol. 81, pp. 991-1002, (1995).

Scott, W.G., "RNA catalysis", Current Opinion in Structural Biology, vol. 8, pp. 720-726, (1998).

Search results of key word search of medline, Mar. 26, 2000.

Search results of key word search on Chemical Abstracts, Mar. 24, 2000.

Search results of key word search from various databases, Mar. 24, 2000.

Seeman, N.C., et al., "Synthetic DNA knots and catenanes", New Journal of Chemistry, vol. 17, pp. 739-755, (1993).

Seeman, N.C., et al., "Emulating biology: Building nanostructures from the bottom up", Proc. Natl. Acad. Sci., vol. 99, suppl. 2, pp. 6451-6455, (2002).

Seeman, N.C., "DNA in a material world", Nature, vol. 421, pp. 427-431, (2003).

Seetharaman, S., et al., "Immobilized RNA switches for the analysis of complex chemical and biological mixtures", Nature Biotechnology, vol. 19, pp. 336-341, (2001).

Sen, D., et al., "DNA enzymes", Current Opinion in Chemical Biology, vol. 2, pp. 680-687, (1998).

Shaiu, W-L., et al., "Atomic force microscopy of oriented linear DNA molecules labeled with 5nm gold spheres", Nucleic Acids Research, vol. 21, No. 1, pp. 99-103, (1993).

Shaw, S.Y., et al., "Knotting of a DNA chain during ring closure", Science, New Series, vol. 260, issue 5107, pp. 533-536, (1993).

Shekhtman, E.M., et al., "Stereostructure of replicative DNA catenanes from eukaryotic cells", New Journal of Chemistry, vol. 17, pp. 757-763, (1993).

Sigurdsson, S.T., et al., "Small ribozymes", RNA Structure and Function, Cold Spring Harbor Laboratory Press (Monograph 35), pp. 339-375, (1998).

Singh, K.K., et al., "Fluorescence Polarization for Monitoring Ribozyme Reactions in Real-Time", Biotechniques, vol. 29, No. 2, pp. 344-351, (2000).

Smith, F.W., et al., "Quadruplex structure of oxytricha telomeric DNA oligonucleotides", Nature, vol. 356, pp. 164-168, (1992).

Smith, J.O., et al., "Molecular recognition of PNA-containing hybrids: Spontaneous assembly of helical cyanine dye aggregates on PNA templates", J. Am. Chem. Soc., vol. 121, No. 12, pp. 2686-2695, (1999).

Soriaga, M.P., et al., "Determination of the orientation of aromatic molecules adsorbed on platinum electrodes: The effect of solute concentration", J. Am. Chem. Soc., vol. 104, No. 14, pp. 3937-3945, (1982).

Soukup, G.A., et al., "Engineering precision RNA molecular switches", Proc. Natl. Acad. Sci. USA, vol. 96, pp. 3584-3589, (1999).

Soukup, G.A., et al., "Allosteric nucleic acid catalysts", Current Opinion in Structural Biology, vol. 10, pp. 318-325, (2000).

Srisawat, C., et al., "Sephadex-binding RNA ligands: rapid affinity purification of RNA from complex RNA mixtures", Nucleic Acids Research, vol. 29, No. 2 e4, pp. 1-5, (2001).

Stage-Zimmermann, T.K., et al., "Hammerhead ribozyme kinetics", RNA, vol. 4, pp. 875-889, (1998).

Stojanovic, M.N., et al., "Aptamer-based colorimetric probe for cocaine", J. Am. Chem. Soc., vol. 124, No. 33, pp. 9678-9679, (2002).

Stojanovic, M.N., et al., "Aptamer-based folding fluorescent sensor for cocaine", Journal of the American Chemical Society, vol. 123, No. 21, pp. 4928-4931, (2001).

Stojanovic, M.N., et al., "Fluorescent sensors based on aptamer self-assembly", Journal of the American Chemical Society, vol. 122, No. 46, pp. 11547-11548, (2000).

Storhoff, J.J., et al., "Programmed materials synthesis with DNA", Chem. Rev., vol. 99, No. 7, pp. 1849-1862, (1999).

Storhoff, J.J., et al., "Facile colorimetric detection of polynucleotides based on gold nanoparticle probes", Proceedings of the 1998 ERDEC Scientific Conference on Chemical and Biological Defense Research, Nov. 17-20, 1998, Aberdeen Proving Ground, pp. 221-226, (1999).

Storhoff, J.J., et al., "What Controls the Optical Properties of DNA-Linked Gold Nanoparticle Assemblies?", J. Am. Chem. Soc., vol. 122, No. 19, pp. 4640-4650, (2000).

Storhoff, J.J., et al., "One-pot colorimetric differentiation of polynucleotides with single base imperfections using gold nanoparticle probes", Journal of the American Chemical Society, vol. 120, No. 9, pp. 1959-1964, (1998).

Streicher, B., et al., "Lead cleavage site in the core structure of group I intron-RNA", Nucleic Acids Research, vol. 21, No. 2, pp. 311-317, (1993).

Sugimoto, N., et al., "Site-specific cleavage reaction catalyzed by leadzyme is enhanced by combined effect of lead and rare earth ions", FEBS Letters, vol. 393, pp. 97-100, (1996).

Sun, L.Q., et al., "Catalytic nucleic acids: From lab to applications", Pharmacological Reviews, vol. 52, pp. 325-347, (2000).

Tahan, J.E., et al., "Electrothermal atomic absorption spectrometric determination of Al, Cu, Ge, Pb, V and Zn in clinical samples and in certified environmental reference materials", Analytica Chimica Acta, vol. 295, pp. 187-197, (1994).

Takagi, Y., et al., "Survey and Summary: Recent advances in the elucidation of the mechanisms of action of ribozymes", Nucleic Acids Research, vol. 29, No. 9, pp. 1815-1834, (2001).

Tang, J., et al., "Rational design of allosteric ribozymes", Chemistry & Biology, vol. 4, No. 6, pp. 453-459, (1997).

Tang, J., et al., "Structural diversity of self-cleaving ribozymes", Proc. Natl. Acad. Sci. USA, vol. 97, No. 11, pp. 5784-5789, (2000).

Tanner, N.K., "Biochemistry of hepatitis delta virus catalytic RNAs", Ribozymes in the Gene Therapy of Cancer, Chapter 3, pp. 23-38, (1998).

Tao, J., et al., "Arginine-Binding RNAs Resembling TAR Identified by in Vitro Selection", Biochemistry, vol. 35, No. 7, pp. 2229-2238, (1996).

Tarasow, T.M., et al., "RNA-catalysed carbon-carbon bond formation", Nature, vol. 389, pp. 54-57, (1997).

Telting-Diaz, M., et al., "Mass-produced ionophore-based fluorescent microspheres for trace level determination of lead ions", Analytical Chemistry, vol. 74, No. 20, pp. 5251-5256, (2002).

Thompson, R.B., et al., "Determination of Picomolar Concentrations of Metal Ions Using Fluorescence Anisotropy: Biosensing with a "Reagentless" Enzyme Transducer", Analytical Chemistry, vol. 70, No. 22, pp. 4717-4723, (1998).

Timmons, C.O., et al., "Investigation of Fatty Acid Monolayers on Metals by Contact Potential Measurements", Journal of Physical Chemistry, vol. 69, No. 3, pp. 984-990, (1965).

Tompkins, H.G., et al., "The study of the gas-solid interaction of acetic acid with a cuprous oxide surface using reflection-absorption spectroscopy", Journal of Colloid and Interface Science, vol. 49, No. 3, pp. 410-421, (1974).

Travascio, P., et al., "A ribozyme and a catalytic DNA with peroxidase activity: active sites versus cofactor-binding sites", Chemistry & Biology, vol. 6, No. 11, pp. 779-787, (1999).

Tsang, J., et al., "In vitro evolution of randomized ribozymes", Methods in Enzymology, vol. 267, pp. 410-426, (1996).

Tsien, R.Y., "Fluorescent and photochemical probes of dynamic biochemical signals inside living cells", Fluorescent Chemosensors for Ion and Molecule Recognition, (ed. Czarnik, A.W.), chapter 9, pp. 130-146, American Chemical Society, (1993).

Tuerk, C., et al., "RNA pseudoknots that inhibit human immunodeficiency virus type 1 reverse transcriptase", Proc. Natl. Acad. Sci. USA, vol. 89, pp. 6988-6992, (1992).

Tuerk, C., et al., "Systematic evolution of ligands by exponential enrichment: RNA ligands to bacteriophage T4 DNA polymerase", Science, New Series, vol. 249, issue 4968, pp. 505-510, (1990).

Tyagi, S., et al., "Molecular Beacons: Probes that fluoresce upon hybridization", Nature Biotechnology, vol. 14, pp. 303-308, (1996).

Tyagi, S., et al., "Multicolor molecular beacons for allele discrimination", Nature Biotechnology, vol. 16, pp. 49-53, (1998).

Tyagi, S., et al., "Wavelength-shifting molecular beacons", Nature Biotechnology, vol. 18, pp. 1191-1196, (2000).

Ueyama, H., "A novel potassium sensing in aqueous media with a synthetic oligonucleotide derivative. Fluorescence resonance energy transfer associated with guanine quartet-potassium ion complex formation", J. Am. Chem. Soc., vol. 124, No. 48, pp. 14286-14287, (2002).

Uphoff, K.W., et al., "In vitro selection of aptamers: the dearth of pure reason", Current Opinion in Structural Biology, vol. 6, pp. 281-288, (1996).

Vaish, N.K., et al., "In vitro selection of a purine nucleotide-specific hammerhead-like ribozyme", Proc. Natl. Acad. Sci. USA, vol. 95, pp. 2158-2162, (1998).

Valadkhan, S., et al., "Splicing-related catalysis by protein-free snRNAs", Nature, vol. 413, pp. 701-707, (2001).

Vianini, E., et al., "In vitro selection of DNA aptamers that bind L-tyrosinamide", Bioorganic & Medicinal Chemistry, vol. 9, pp. 2543-2548, (2001).

Walkup, G.K., et al., "Design and Evaluation of a Peptidyl Fluorescent Chemosensor for Divalent Zinc", J. Am. Chem. Soc., vol. 118, No. 12, pp. 3053-3054, (1996).

Wallace, S.T., et al., In vitro selection and characterization of streptomycin-binding RNAs: recognition discrimination between antibiotics. RNA, vol. 4, pp. 112-123, (1998).

Wallis, M.G., et al., "A novel RNA motif for neomycin recognition", Chemistry & Biology, vol. 2, No. 8, pp. 543-552, (1995).

Wallis, M.G., et al., "In vitro selection of a viomycin-binding RNA pseudoknot", Chemistry & Biology, vol. 4, No. 5, pp. 357-366, (1997).

Walter, F., et al., "Folding of the four-way RNA junction of the hairpin ribozyme", Biochemistry, vol. 37, No. 50, pp. 17629-17636, (1998).

Walter, N.G., et al., "The hairpin ribozyme: structure, assembly and catalysis", Current Opinion in Chemical Biology, vol. 2, pp. 24-30, (1998).

Wang, D.Y., et al., "A general strategy for effector-mediated control of RNA-cleaving ribozymes and DNA enzymes", J. Mol. Biol., vol. 318, pp. 33-43, (2002).

Wang, F., et al., "Sphingosine-1-phosphate Inhibits Motility of Human Breast Cancer Cells Independently of Cell Surface Receptors", Cancer Research, vol. 59, pp. 6185-6191, (1999).

Wang, J., "Survey and Summary: From DNA biosensors to gene chips", Nucleic Acids Research, vol. 28, No. 16, pp. 3011-3016, (2000).

Wang, K.Y., et al., "A DNA aptamer which binds to and inhibits thrombin exhibits a new structural motif for DNA", Biochemistry, vol. 32, No. 8, pp. 1899-1904, (1993).

Wang, Y., et al., "Assembly and characterization of five-arm and six-arm DNA branched junctions", Biochemistry, vol. 30, pp. 5667-5674, (1991).

Wang, Y., et al., "RNA molecules that specifically and stoichiometrically bind aminoglycoside antibiotics with high affinities", Biochemistry, vol. 35, No. 38, pp. 12338-12346, (1996).

Wecker, M., et al., "In vitro selection of a novel catalytic RNA: characterization of a sulfur alkylation reaction and interaction with a small peptide", RNA, vol. 2, pp. 982-994, (1996).

Wedekind, J.E., et al., "Crystal structure of a lead-dependent ribozyme revealing metal binding sites relevant to catalysis", Nature Structural Biology, vol. 6, No. 3, pp. 261-268, (1999).

Wedekind, J.E., et al., "Crystal structure of the leadzyme at 1.8 Å Resolution: Metal ion binding and the implications for catalytic mechanism and allo site ion regulation", Biochemistry, vol. 42, No. 32, pp. 9554-9563, (2003).

Wells, R.D., "Unusual DNA structures", Journal of Biological Chemistry, vol. 263, No. 3, pp. 1095-1098, (1988).

Werstuck, G., et al., "Controlling gene expression in living cells through small molecule-RNA interactions", Science, vol. 282, pp. 296-298, (1998).

Whaley, S.R., et al., "Selection of peptides with semiconductor binding specificity for directed nanocrystal assembly", Nature, vol. 405, pp. 665-668, (2000).

Whitesides, G.M., et al., "Self-assembled monolayers and lithography", Proceedings of the Robert A. Welch Foundation 39th Conference on Chemical Research on Nanophase Chemistry, pp. 109-121, Houston, TX, Oct. 23-24, 1995.

Wiegand, T.W., et al., "High-affinity oligonucleotide ligands to human IgE inhibit binding to Fc epsilon receptor I", The Journal of Immunology, vol. 157, pp. 221-230, (1996).

Wiegand, T.W., et al., "Selection of RNA amide synthases", Chemistry & Biology, vol. 4, No. 9, pp. 675-683, (1997).

Williams, K.P., et al., "Bioactive and nuclease-resistant L-DNA ligand of vasopressin", Proc. Natl. Acad. Sci. USA, vol. 94, pp. 11285-11290, (1997).

Williams, K.P., et al., "Selection of novel $Mg^{2+}$-dependent self-cleaving ribozymes" The EMBO Journal, vol. 14, No. 18, pp. 4551-4557, (1995).

Wilson, C., et al., "Functional requirements for specific ligand recognition by a biotin-binding RNA Pseudoknot", Biochemistry, vol. 37, No. 41, pp. 14410-14419, (1998).

Wilson, C., et al., "In vitro evolution of a self-alkylating ribozyme", Nature, vol. 374, pp. 777-782, (1995).

Wilson, C., et al., "Isolation of a fluorophore-specific DNA aptamer with weak redox activity", Chemistry & Biology, vol. 5, No. 11, pp. 609-617, (1998).

Wilson, D.S., et al., "In vitro selection of functional nucleic acids", Annu. Rev. Biochem. vol. 68, pp. 611-647, (1999).

Winkler, J.D., et al., "Photodynamic Fluorescent Metal Ion Sensors with Parts per Billion Sensitivity", J. Am. Chem. Soc., vol. 120, No. 13, pp. 3237-3242, (1998).

Wittmann, C., et al.,"Microbial and Enzyme sensors for environmental monitoring", Handbook of Biosensors and Electronic Noses: Medicine, Food, and the Environment, pp. 299-332, (1997).

Xia, P., et al., "Activation of Sphingosine Kinase by Tumor Necrosis Factor-α Inhibits Apoptosis in Human Endothelial Cells", Journal of Biological Chemistry, vol. 274, No. 48, pp. 34499-34505, (1999).

Yan, H., et al., "DNA-Templated self-assembly of protein arrays and highly conductive nanowires", Science, vol. 301, pp. 1882-1884, (2003).

Yang, Q., et al., "DNA ligands that bind tightly and selectively to cellobiose", Proc. Natl. Acad. Sci. USA, vol. 95, pp. 5462-5467, (1998).

English Translation of Yang, Y., et al., "Measurement of lead and magnesium in distilled spirits using inductively coupled plasma optical emission spectrometry viewed from the end", Analytical Chemistry (Fenxi Huaxue), Chinese Journal of Analytical Chemistry, vol. 25, No. 9, pp. 1114-1117, (1997).

Yurke, B., et al., "A DNA-fuelled molecular machine made of DNA", Nature, vol. 406, pp. 605-608, (2000).

Zhang, B., et al., "Peptide bond formation by in vitro selected ribozymes", Nature, vol. 390, pp. 96-100, (1997).

Zhang, P., et al., "Design of a molecular beacon DNA probe with two fluorophores", Angewandte Chemie International Edition, vol. 40, No. 2, pp. 402-405, (2001).

Zillmann, M., et al., "In vitro optimization of truncated stem-loop II variants of the hammerhead ribozyme for cleavage in low concentrations of magnesium under non-turnover conditions", RNA, vol. 3, pp. 734-747, (1997).

Zimmerman, J.M., et al., "In vivo selection of spectinomycin-binding RNAs", Nucleic Acids Research, vol. 30, No. 24, pp. 5425-5435, (2002).

Zimmermann, G.R., et al., "Molecular interactions and metal binding in the theophylline-binding core of an RNA aptamer", RNA, vol. 6, pp. 659-667, (2000).

International Search Report dated Nov. 21, 2005 for PCT application No. PCT/US2005/001060.

Supplemental International Search Report dated Jan. 10, 2006 for PCT application No. PCT/US2005/001060.

Liu, J., et al., "Size control, metal substitution, and catalytic application of cryptomelane nanomaterials prepared using cross-linking reagents", Chem. Mater., vol. 16, No. 2, pp. 276-285, (2004).

Cake, K.M., et al., "Partition of circulating lead between serum and red cells is different for internal and external sources of lead", American Journal of Industrial Medicine, vol. 29, pp. 440-445, (1996).

International Search Report dated Aug. 31, 2004 for PCT application No. PCT/US2004/002946.

Hazarika, P., et al., "Reversible switching of DNA-Gold nanoparticle aggregation", Angewandte Chemie International Edition, vol. 43, No. 47, pp. 6469-6471, (2004).

International Search Report dated May 29, 2006 for PCT application No. PCT/US2005/037896.

Liu, J., et al., "Improving fluorescent DNAzyme biosensors by combining Inter- and Intramolecular quenchers", Analytical Chemistry, vol. 75, No. 23, pp. 6666-6672, (2003).

Liu, J., et al., "Stimuli-responsive disassembly of nanoparticle aggregates for light-up colorimetric sensing", Journal of the American Chemical Society, vol. 127, No. 36, pp. 12677-12683, (2005).

European Search Report dated Jul. 10, 2006 for PCT application No. PCT/US2003/12576.

Tanner, F.C., et al., "Transfection of human endothelial cells", Cardiovascular research, vol. 35, pp. 522-528, (1997).

International Search Report dated Nov. 17, 2006 for PCT application No. PCT/US2006/001627.

Liu, J., et al., "DNAzyme-directed assembly of gold nanoparticles as colorimetric sensor for a broad range of analytes", pp. 1-3, located at http://ieeenano2003.arc.nasa.gov/THM@.pdf, (2003).

Wang, D.Y., et al., "A general approach for the use of oligonucleotide effectors to regulate the catalysis of RNA-cleaving ribozymes and DNAzymes", Nucleic Acids Research, vol. 30, No. 8, pp. 1735-1742, (2002).

Levy, M., et al., "Exponential growth by cross-catalytic cleavage of deoxyribozymogens",PNAS, vol. 100, No. 11, pp. 6416-6421, (2003).

Beyer, S., et al., "A modular DNA signal translator for the controlled release of a protein by an aptamer", Nucleic Acids Research, vol. 34, No. 5, pp. 1581-1587, (2006).

Frauendorf, C., et al., "Detection of small organic analytes by fluorescing molecular switches", Bioorganic & Medicinal Chemistry, vol. 9, pp. 2521-2524, (2001).

Glynou, K., et al., "Oligonucleotide-functionalized gold nanoparticles as probes in a dry-reagent strip biosensor for DNA analysis by hybridization", Anal. Chem, vol. 75, No. 16, pp. 4155-4160, (2003).

Liu, J., et al., "Optimization of a $Pb^{2+}$-directed gold nanoparticle/DNAzyme assembly and its application as a colorimetric biosensor for $Pb^{2+}$", Chem. Mater., vol. 16, No. 17, pp. 3231-3238, (2004).

Jones, K.D., et al., "Anniversary Essays, 3. Assay development, Changes in the development of rapid assays since 1995", Medical Devicelink, found at: http://www.devicelink.com/ivdt/archive/05/04/005.html, 3 pages, (2005).

Product Description: Pall Corporation, "Immunochromatographic, lateral flow or strip tests development ideas", found at: http://www.pall.com/34445_4154.asp, 7 pages, (1998).

Liu, J., et al., "Fast colorimetric sensing of adenosine and cocaine based on a general sensor design involving aptamers and nanoparticles", Angew. Chem. Int. Ed., vol. 45, pp. 90-94, (2006).

Liu, J., et al., "A simple and sensitive "dipstick" test in serum based on lateral flow separation of aptamer-linked nanostructures", Angewandte Chemie International Edition, vol. 45, pp. 7955-7959, (2006).

Jiang, P. et al., "Fluorescent detection of zinc in biological systems: recent development on the design of chemosensors and biosensors", Coordination Chemistry Reviews, vol. 248, pp. 205-229, (2004).

Lim, M.H. et al., "Metal-based turn-on fluorescent probes for sensing nitric oxide", Accounts of Chemical Research, vol. 40, No. 1, pp. 41-51, (2007).

Yoon, S. et al., "Screening mercury levels in fish with a selective fluorescent chemosensor", Journal of the American Chemical Society, vol. 127, pp. 16030-16031, (2005).

Yang, L. et al., "Imaging of the intracellular topography of copper with a fluorescent sensor and by synchrotron x-ray fluorescence microscopy", Proceedings of the National Academy of Science, vol. 102, No. 32, pp. 11179-11184, (2005).

He, Q. et al., "A selective fluorescent sensor for detecting lead in living cells", Journal of the American Chemical Society, vol. 128, pp. 9316-9317, (2006).

Zeng, L. et al., "A selective turn-on fluorescent sensor for imaging copper in living cells", Journal of the American Chemical Society, vol. 128, pp. 10-11, (2006).

Wegner, S.V. et al., "Design of an emission ratiometric biosensor from MerR family proteins: A sensitive and selective sensor for $Hg^{2+}$", Journal of the American Chemical Society, vol. 129, pp. 3474-3475, (2007).

Nolan, E.M. et al., "Turn-on and ratiometric mercury sensing in water with a red-emitting probe", Journal of the American Chemical Society, vol. 129, pp. 5910-5918, (2007).

Sasaki, D.Y. et al., "Metal-induced dispersion of lipid aggregates: A simple, selective, and sensitive fluorescent metal ion sensor", Angew. Chem. Int. Ed. England, vol. 34, No. 8, pp. 905-907, (1995).

Torrado, A. et al., "Exploiting polypeptide motifs for the design of selective Cu(II) ion chemosensors" Journal of the American Chemical Society, vol. 120, pp. 609-610, (1998).

Grandini, P. et al., "Exploiting the self-assembly strategy for the design of selective $Cu^{II}$ ion chemosensors", Angew. Chem. Int. Ed, vol. 38, No. 20, pp. 3061-3064, (1999).

Klein, G. et al., "A fluorescent metal sensor based on macrocyclic chelation", Chem. Comm., pp. 561-562, (2001).

Zheng, Y. et al., "A new fluorescent chemosensor for copper ions based on tripeptide glycyl-histidyl-lysine (GHK)", Organic Letters, vol. 3, No. 21, pp. 3277-3280, (2001).

Boiocchi, M. et al., "A two-channel molecular dosimeter for the optical detection of copper(II)" Chem. Comm, pp. 1812-1813, (2003).

Zheng, Y. et al., "Peptidyl fluorescent chemosensors for the detection of divalent copper", Analytical Chemistry, vol. 75, No. 7, pp. 1706-1712, (2003).

Zheng, Y. et al., "Development of fluorescent film sensors for the detection of divalent copper", Journal of the American Chemical Society, vol. 125, pp. 2680-2686, (2003).

Roy, B.C. et al., "Synthesis of new, pyrene-containing metal-chelating lipids and sensing of cupric ions", Organic Letters, vol. 5, No. 1, pp. 11-14, (2003).

Kaur, S. et al., "Photoactive chemosensors 4: a $cu^{2+}$ protein cavity mimicking fluorescent chemosensor for selective $Cu^{2+}$ recognition", Tetrahedron Letters, vol. 45, pp. 5081-5085, (2004).

Mei, Y. et al., "A selective and sensitive chemosensor for $Cu^{2+}$ based on 8-hydroxyquinoline", Tetrahedron Letters, vol. 47, pp. 2447-2449, (2006).

Zhang, X-B. et al., "A highly selective fluorescent sensor for $Cu^{2+}$ based on 2-(2'-hydroxyphenyl) benzoxazole in a poly(vinyl chloride) matrix", Analytica Chimica Acta, vol. 567, pp. 189-195, (2006).

Comba, P. et al., "Synthesis of new phenanthroline-based heteroditopic ligands—highly efficient and selective fluorescence sensors for copper (II) ions", European Journal of Inorganic Chemistry, pp. 4442-4448, (2006).

Kim, S. H. et al., "$Hg^{2+}$-selective off-on and $Cu^{2+}$-selective on-off type fluoroionophore based upon cyclam", Organic Letters, vol. 8, No. 3, pp. 371-374, (2006).

White, B. R. et al., "Fluorescent peptide sensor for the selective detection of $Cu^{2+}$", Talanta, vol. 71, pp. 2015-2020, (2007).

Oter, O. et al., "Spectral characterization of a newly synthesized fluorescent semicarbazone derivative and its usage as a selective fiber optic sensor for copper(II)", Analytica Chimica Acta, vol. 584, pp. 308-314, (2007).

Dujols, V. et al., "A long-wavelength fluorescent chemodosimeter selective for Cu(II) ion in water", Journal of the American Chemical Society, vol. 119, pp. 7386-7387, (1997).

Yang, J-S. et al., "$Cu^{2+}$-induced blue shift of the pyrene excimer emission: a new signal transduction mode of pyrene probes", Organic Letters, vol. 3, No. 6, pp. 889-892, (2001).

Kaur, S. et al., "Photoactive chemosensors 3: a unique case of fluorescence enhancement with Cu(II)", Chem. Comm., pp. 2840-2841, (2002).

Wu, Q. et al., "Catalytic signal amplification using a heck reaction. An example in the fluorescence sensing of Cu(II)", Journal of the American Chemical Society, vol. 126, pp. 14682-14683, (2004).

Royzen, M. et al., "Ratiometric displacement approach to Cu(II) sensing by fluorescence", Journal of the American Chemical Society, vol. 127, pp. 1612-1613, (2005).

Xu, Z. et al., "Ratiometric and selective fluorescent sensor for $Cu^{II}$ based on internal charge transfer (ICT)", Organic Letters, vol. 7, No. 5, pp. 889-892, (2005).

Wen, Z-C. et al., "A highly selective charge transfer fluoroionophore for $Cu^{2+}$", Chem. Commun., pp. 106-108, (2006).

Yang, H. et al., "Highly selective ratiometric fluorescent sensor for Cu(II) with two urea groups", Tetrahedron Letters, vol. 47, pp. 2911-2914, (2006).

Martinez, R. et al., "2-aza-1,3-butadiene derivatives featuring an anthracene or pyrene unit: highly selective colorimetric and fluorescent signaling of $Cu^{2+}$ cation", Organic Letters, vol. 8, No. 15, pp. 3235-3238, (2006).

Navani, N.K. et al., "Nucleic acid aptamers and enzymes as sensors", Current Opinion in Chemical Biology, vol. 10, pp. 272-281, (2006).

Liu, J. et al., "A catalytic beacon sensor for uranium with parts-per-trillion sensitivity and millionfold selectivity", Proceedings of the National Academy of Science, vol. 104, No. 7, pp. 2056-2061, (2007).

Georgopoulos, P.G. et al., "Environmental copper: its dynamics and human exposure issues", Journal of Toxicology and Environmental Health, Part B, vol. 4, pp. 341-394, (2001).

Hertzberg, R.P. et al., "Cleavage of DNA with methidiumpropyl-EDTA-iron(II): reaction conditions and product analyses", Biochemistry, vol. 23, pp. 3934-3945, (1984).

Yazzie, M. et al., "Uranyl acetate causes DNA single strand breaks in vitro in the presence of ascorbate (Vitamin C)", Chem. Res. Toxicol., vol. 16, pp. 524-530, (2003).

Bolletta, F. et al., "A $[Ru^{II} (bipy)_3]$-[1,9-diamino-3,7-diazanonane-4,6-dione] two-component system as an efficient on-off luminescent chemosensor for $Ni^{2+}$ and $Cu^{2+}$ in water, based on an ET (energy transfer) mechanism", Journal of the Chemical Society, Dalton Transactions, pp. 1381-1385, (1999).

Carmi, N. et al., "Characterization of a DNA-cleaving deoxyribozyme", Bioorganic & Medicinal Chemistry, vol. 9, issue 10, pp. 2589-2600, (2001).

Liu, J. et al., "A DNAzyme catalytic beacon sensor for paramagnetic $Cu^{2+}$ ions in aqueous solution with high sensitivity and selectivity", Journal of the American Chemical Society, vol. 129, No. 32, pp. 9838-9839, (2007), ASAP Web Release Date: Jul. 24, 2007.

Tanaka, K. et al., "Programmable self-assembly of metal ions inside artificial DNA duplexes", Nature Nanotechnology, vol. 1, pp. 190-194, (2006).

Achenbach, J.C. et al., "DNAzymes: From creation in vitro to application in vivo", Current Pharmaceutical Biotechnology, vol. 5, pp. 321-336, (2004).

Balaji, T. et al., "Optical sensor for the visual detection of mercury using mesoporous silica anchoring porphyrin moiety", The Analyst, vol. 130, pp. 1162-1167, (2005).

Caballero, A. et al., "Highly selective chromogenic and redox or fluorescent sensors of $Hg^{2+}$ in aqueous environment based on 1,4-disubstituted azines", Journal of the American Chemical Society, vol. 127, pp. 15666-15667, (2005).

Chan, W.H. et al., "Development of a mercury ion-selective optical sensor based on fluorescence quenching of 5,10,15, 20-tetraphenylporphyrin", Analytica Chimica Acta, vol. 444, pp. 261-269, (2001).

Chen, P. et al., "A general strategy to convert the merR family proteins into highly sensitive and selective fluorescent biosensors for metal ions", Journal of the American Chemical Society, vol. 126, pp. 728-729, (2004).

Chiuman, W. et al., "Efficient signaling platforms built from a small catalytic DNA and doubly labeled fluorogenic substrates", Nucleic Acids Research, vol. 35, No. 2, pp. 401-405, (2007).

Cruz, R.P.G. et al., "Dinucleotide junction cleavage versatility of 8-17 deoxyribozyme", Chemistry & Biology, vol. 11, pp. 57-67, (2004).

Frasco, M.F. et al., "Mechanisms of cholinesterase inhibition by inorganic mercury", the FEBS Journal, vol. 274, pp. 1849-1861, (2007).

Guo, X. et al., "A highly selective and sensitive fluorescent chemosensor for $Hg^{2+}$ in neutral buffer aqueous solution", The Jouranl of the American Chemical Society, vol. 126, pp. 2272-2273, (2004).

Harris, H.H. et al., "The chemical form of mercury in fish", Science, vol. 301, pp. 1203, (2003).

Ha-Thi, M-H. et al., "Highly selective and sensitive phosphane sulfide derivative for the detection of $Hg^{2+}$ in an organoaqueous medium", Organic Letters, vol. 9, No. 6, pp. 1133-1136, (2007).

Joyce, G.F. et al., "Directed evolution of nucleic acid enzymes", Annual Review Biochem., vol. 73, pp. 791-836, (2004).

Ko, S-K. et al., "In vivo monitoring of mercury ions using a rhodamine-based molecular probe", Journal of the American Chemical Society, vol. 128, pp. 14150-14155, (2006).

Kuswandi, B. et al., "Capillary optode: determination of mercury(II) in aqueous solution", Analytical Letters, vol. 32, No. 9. 4, pp. 649-664, (1999).

Kuswandi, B. et al., "Selective pool optode for mercury ion sensing in aqueous solution", Sensors and Actuators B, vol. 74, pp. 131-137, (2001).

Lee, J-S. et al., "Colorimetric detection of mercuric ion ($Hg^{2+}$) in aqueous media using DNA-functionalized gold nanoparticles", Angewandte Chemie International Edition, vol. 46, pp. 4093-4096, (2007).

Liu, B. et al., "A selective fluorescent ratiometric chemodosimeter for mercury ion", Chem. Communications, pp. 3156-3158, (2005).

Liu, J. et al., "Fluorescent DNAzyme biosensors for metal ions based on catalytic molecular beacons", Methods in Molecular Biology, vol. 335, pp. 275-288, (2006).

Matsushita, M. et al., "A blue fluorescent antibody-cofactor sensor for mercury", Organic Letters, vol. 7, No. 22, pp. 4943-4946, (2005).

Miyake, Y. et al., "$Mercury^{II}$-mediated formation of thymine-$Hg^{II}$-thymine base pairs in DNA duplexes", Journal of the American Chemical Society, vol. 128, No. 7, pp. 2172-2173, (2006).

Nolan, E.M. et al., "A "turn-on" fluorescent sensor for the selective detection of mercuric ion in aqueous media", Journal of the American Chemical Society, vol. 125, pp. 14270-14271, (2003).

Ono, A. et al., "highly selective oligonucleotide-based sensor for mercury (II) in aqueous solutions", Angew. Chem. Int. Ed., vol. 43, pp. 4300-4302, (2004).

Ostatna, V. et al., "Self-assembled monolayers of thiol-end-labeled DNA at mercury electrodes", Langmuir, vol. 22, pp. 6481-6484, (2006).

Prodi, L. et al., "An effective fluorescent achemosensor for mercury ions", Journal of the American Chemical Society, vol. 122, No. 28, pp. 6769-6770, (2000).

Silverman, S.K., "Survey and Summary: In vitro selection, characterization, and application of deoxyribozymes that cleave RNA", Nucleic Acids Research, vol. 33, No. 19, pp. 6151-6163, (2005).

Song, K.C. et al., "Fluorogenic $Hg^{2+}$-selective chemodosimeter derived from 8-hydroxyquinoline", Organic Letters, vol. 8, No. 16, pp. 3413-3416, (2006).

Szurdoki, F. et al., "A combinatorial approach to discover new chelators for optical metal ion sensing", Analytical Chemistry, vol. 72, No. 21, pp. 5250-5257, (2000).

Tanaka, Y. et al., "$^{15}$N-$^{15}$N J-coupling across Hg$^{II}$: Direct observation of Hg$^{II}$-mediated T-T base pairs in a DNA duplex" Journal of the American Chemical Society, vol. 129, No. 2, pp. 244-245, (2007).
Jacoby, M. "Mercury Sensor—Analytical Chemistry: Colorimetric method is sensitive and selective", Chemical & Engineering News, pp. 15, May 7, 2007.
Vannela, R. et al., "In vitro selection of Hg (II) and as (V)-dependent RNA-cleaving DNAzymes", Environmental Engineering Science, vol. 24, No. 1, pp. 73-84, (2007).
Vaughan, A.A. et al., "Optical fibre reflectance sensors for the detection of heavy metal ions based on immobilized Br-PADAP", Snesors and Actuators B, vol. 51, pp. 368-376, (1998).
Villa, M. et al., "A luminescence-based mercury biosensor", Analytical Chemistry, vol. 67, No. 3, pp. 667-669, (1995).
Wang, J. et al., "Detecting Hg$^{2+}$ ions with an ICT fluorescent sensor molecule: Remarkable emission spectra shift and unique selectivity", Journal of Organic Chemistry, vol. 71, pp. 4308-4311, (2006).
Wang, J. et al., "A series of polyamide receptor based PET fluorescent sensor molecules: Positively cooperative Hg$^{2+}$ ion binding with high sensitivity", Organic Letters, vol. 8, No. 17, pp. 3721-3724, (2006).
Widmann, A. et al., "Mercury detection in seawater using a mercaptoacetic acid modified gold microwire electrode", Electroanalysis, vol. 17, No. 10, pp. 825-831, (2005).
Xiao, Y. et al., "Electrochemical detection of parts-per-billion lead via an electrode-bound DNAzyme assembly", Journal of the American Chemical Society, vol. 129, pp. 262-263, (2007).
Yang, W. et al., "Solid phase extraction and spectrophotometric determination of mercury in tobacco and tobacco additives with 5-(p-aminobenzylidene)-thiothiorhodanine", Journal of the Brazilian Chemical Society, vol. 17, No. 5, pp. 1039-1044, (2006).
Yang, Y-K. et al., "A rhodamine-based fluorescent and colorimetric chemodosimeter for the rapid detection of Hg2+ ions in aqueous media", Journal of the American Chemical Society, vol. 127, pp. 16760-16761, (2005).
Zhang, X-B. et al "An optical fiber chemical sensor for mercury ions based on a porphyrin dimmer", Analytical Chemistry, vol. 74, No. 4, pp. 821-825, (2002).
Zhao, Y. et al., "A "turn-on" fluorescent sensor for selective Hg(II) detection in aqueous media based on metal-induced dye formation", Inorganic Chemistry, vol. 45, No. 25, pp. 10013-10015, (2006).
Zhao, Y. et al., "Tuning the sensitivity of a foldamer-based mercury sensor by its folding energy", Journal of the American Chemical Society, vol. 128, No. 31, pp. 9988-9989, (2006).
Zhao, Y. et al., "Detection of Hg2∓ in aqueous solutions with a foldamer-based fluorescent sensor modulated by surgactant micelles", Organic Letters, vol. 8, No. 21, pp. 4715-4717, (2006).
Zuker, M., "Mfold web server for nucleic acid folding and hybridization prediction", Nucleic Acids Research, vol. 31, No. 13, pp. 3406-3415, (2003).
International Search Report dated May 10, 2007 for PCT application No. PCT/US2006/030617.
Liu, J. et al., "Adenosine-dependent assembly of aptazyme-functionalized gold nanoparticles and its application as a colorimetric biosensor", Analytical Chemistry, vol. 76, No. 6, pp. 1627-1632, (2004).
Liu, J. et al., "Smart nanomaterials responsive to multiple chemical stimuli with controllable cooperativity", Advanced Materials, vol. 18, No. 13, pp. 1667-1671, (2006).
Nutiu, R. et al., "Signaling aptamers for monitoring enzymatic activity and for inhibitor screening", Chembiochem—A European Journal of Chemical Biology, vol. 5, No. 8, pp. 1139-1144, (2004).
Nutiu, R. et al., "Structure-switching signaling aptamers: Transducing molecular recognition into fluorescence signaling", Chemistry—A European Journal, vol. 10, No. 8, pp. 1868-1876, (2004).
International Search Report dated Jul. 31, 2007 for PCT application No. PCT/US2007/064055.
Ahern, H., "Biochemical, reagent kits offer scientists good return on investment", The Scientist, vol. 9, No. 15, pp. 20-22, (1995).
Homann, M. et al., "Dissociation of long-chain duplex RNA can occur via strand displacement in vitro: biological implication", Nucleic Acids Research, vol. 24, No. 22, pp. 4395-4400, (1996).
Alivisatos, A.P. et al., "Quantum dots as cellular probes", Annual Review Biomed. Eng, vol. 7, pp. 55-76, (2005).

Dyadyusha, L. et al., "Quenching of CdSe quantum dot emission, a new approach for biosensing", Chemical Communication, pp. 3201-3203, (2005).
Ellington, A.D. et al., "In vitro selection of RNA molecules that bind specific ligands", Nature, vol. 346, pp. 818-822, (1990).
Gerion, D. et al., "Room-temperature single-nucleotide polymorphism and multiallele DNA detection using fluorescent nanocrystals and microarrays", Analytical Chemistry, vol. 75, No. 18, pp. 4766-4772, (2003).
Goldman, E.R. et al., "Multiplexed toxin analysis using four colors of quantum dot fluororeagents", Analytical Chemistry, vol. 76, No. 3, pp. 684-688, (2004).
Gueroui, Z. et al., "Single-molecule measurements of gold-quenched quantum dots", Physical Review Letters, vol. 93, No. 16, pp. 166108/1-166108/4, (2004).
Han, M. et al., "Quantum-dot-tagged microbeads for multiplexed optical coding of biomolecules", Nature Biotechnology, vol. 19, pp. 631-635, (2001).
Hansen, J.A. et al., "Quantum-dot/Aptamer-based ultrasensitive multi-analyte electrochemical biosensor", Journal of the American Chemical Society, vol. 128, No. 7, pp. 2228-2229, (2006).
Hartig, J.S. et al., "Protein-dependent ribozymes report molecular interactions in real time", Nature Biotechnology, vol. 20, pp. 717-722, (2002).
Herman, T. et al., "Adaptive recognition by nucleic acid aptamers", Science, vol. 287, pp. 820-825, (2000).
Kurreck, J., "Antisense technologies Improvement through novel chemical modifications", Eur. J. Biochem, vol. 270, pp. 1628-1644, (2003).
Lee, J.F. et al., "Aptamer database", Nucleic Acids Research, vol. 32, Database Issue, pp. D95-D100, (2004).
Levy, M. et al., "Quantum-dot aptamer beacons for the detection of proteins", ChemBioChem, vol. 6, pp. 2163-2166, (2005).
Liu, J. et al., "Smart nanomaterials responsive to multiple chemical stimuli with controllable cooperativity", Advanced Materials, vol. 18, pp. 1667-1671, (2006).
Liu, J. et al., "Preparation of aptamer-linked gold nanoparticle purple aggregates for colorimetric sensing of analytes", Nature Protocols, vol. 1, No. 1, pp. 246-252, (2006).
Medintz, I.L. et al., "Quantum dot bioconjugates for imaging, labeling and sensing", Nature Materials, vol. 4, pp. 435-446, (2005).
Miduturu, C.V. et al., "Modulation of DNA constraints that control macromolecular folding", Angew. Chem. Int. Ed., vol. 45, pp. 1918-1921, (2006).
Mitchell, G.P. et al., "Programmed assembly of DNA functionalized quantum dots", Journal of the American Chemical Society, vol. 121, No. 35, pp. 8122-8123, (1999).
Nutiu, R. et al., "Structure-switching signaling aptamers: Transducing molecular recognition into fluorescence signaling", Chem. Eur. J., vol. 10, pp. 1868-1876, (2004).
Oh, E. et al., "Inhibition assay of biomolecules based on fluorescence resonance energy transfer (FRET) between quantum dots and gold nanoparticles", Journal of the American Chemical Society, vol. 127, No. 10, pp. 3270-3271, (2005).
Rajendran, M. et al., "In vitro selection of molecular beacons", Nucleic Acids Research, vol. 31, No. 19, pp. 5700-5713, (2003).
Vet, J.A.M. et al., "Multiplex detection of four pathogenic retroviruses using molecular beacons", Proceedings of the National Academy of Science, USA., vol. 96, pp. 6394-6399, (1999).
Wargnier, R. et al., "Energy transfer in aqueous solutions of oppositely charged CdSe/ZnS core/shell quantum dot-nanogold assemblies", Nano Letters, vol. 4, No. 3, pp. 451-457, (2004).
Wilson, R. et al., "Encoded microcarriers for high-throughput multiplexed detection", Angewandte Chemie International Edition, vol. 45, pp. 6104-6117, (2006).
Winkler, W.C. et al., "Regulation of bacterial gene expression by riboswitches", The Annual Review of Microbiology, vol. 59, pp. 487-517, (2005).
Yang, C.J. et al., "Light-switching excimer probes for rapid protein monitoring in complex biological fluids", PNAS, vol. 102, No. 48, pp. 17278-17283, (2005).

Liu, J. et al., "Quantum dot encoding of aptamer-linked nanostructures for one-pot simultaneous detection of multiple analytes", Analytical Chemistry, vol. 79, No. 11, pp. 4120-4125, (2007).

Lu, Y. et al., "Smart nanomaterials inspired by biology: Dynamic assembly of error-free nanomaterials in response to multiple chemical and biological stimuli", Accounts of Chemical Research, vol. 40, No. 5, pp. 315-323, (2007).

Allen, M.J. et al., "Magnetic resonance contrast agents for medical and molecular imaging", Met. Ions Biol. Syst., vol. 42, pp. 1-38, (2004).

Artemov, D. et al., "MR molecular imaging of the Her-2/neu receptor in breast cancer cells using targeted iron oxide nanoparticles", Magnetic Resonance in Medicine, vol. 49, pp. 403-408, (2003).

Buerger, C. et al., "Sequence-specific peptide aptamers, interacting with the intracellular domain of the epidermal growth factor receptor, interfere with stat3 activation and inhibit the growth of tumor cells", The Journal of Biological Chemistry, vol. 278, No. 39, pp. 37610-37621, (2003).

Buerger, C. et al., "Bifunctional recombinant proteins in cancer therapy: cell penetrating peptide aptamers as inhibitors of growth factor signaling", J. Cancer Research Clin. Oncol., vol. 129, pp. 669-675, (2003).

Carr, D.H. et al., "Gadolinium-DTPA as a contrast agent in MRI: initial clinical experience in 20 patients", American Journal of Roentfenol., vol. 143, pp. 215-224, (1984).

Chen, Y. et al., "An autonomous DNA nanomotor powered by a DNA enzyme", Angew. Chem. Int. Ed., vol. 43, pp. 3554-3557, (2004).

Corot, C. et al., "Macrophage imaging in central nervous system and in carotid atherosclerotic plaque using ultrasmall superparamagnetic iron oxide in magnetic resonance imaging", Investigative Radiology, vol. 39, No. 10, pp. 619-625, (2004).

Dodd, C.H. et al., "Normal T-cell response and in vivo magnetic resonance imaging of T cells loaded with HIV transactivator-peptide-derived superparamagnetic nanoparticles", Journal of Immunological Methods, vol. 256, pp. 89-105, (2001).

Drolet, D.W. et at "An enzyme-linked oligonucleotide assay", Nature Biotechnology, vol. 14, pp. 1021-1025, (1996).

Enochs, W.S. et al., "Improved delineation of human brain tumors on MR images using a long-circulating, superparamagnetic iron oxide agent", Journal of Magnetic Resonance Imaging, vol. 9, pp. 228-232, (1999).

Famulok, M. et at "Nucleic acid aptamers-from selection in vitro to applications in vivo", Accounts of Chemical research, vol. 33, No. 9, pp. 591-599, (2000).

Fang, X. et al., "Molecular aptamer for real-time oncoprotein platelet-derived growth factor monitoring by fluorescence anisotropy", Analytical Chemistry, vol. 73, No. 23, pp. 5752-5757, (2001).

Frullano, L. et al., "Synthesis and characterization of a doxorubicin-Gd(III) contrast agent conjugate: A new approach toward prodrug-procontrast complexes", Inorganic Chemistry, vol. 45, No. 21, pp. 8489-8491, (2006).

Hamaguchi, N. et al., "Aptamer beacons for the direct detection of proteins", Analytical Biochemistry, vol. 294, pp. 126-131, (2001).

Harisinghani, M.G. et al., "Noninvasive detection of clinically occult lymph-node metastases in prostate cancer", The New England Journal of Medicine, vol. 348, No. 25, pp. 2491-2499, (2003).

Hermann, T. et al., "Adaptive recognition by nucleic acid aptamers", Science, vol. 287, pp. 820-825, (2000).

Hoppe-Seyler, F. et al., "Peptide aptamers: Specific inhibitors of protein function", Current Molecular Medicine, vol. 4, pp. 529-538, (2004).

Huang, C-C. et al., "Aptamer-modified gold nanoparticles for colorimetric determination of platelet-derived growth factors and their receptors", Analytical Chemistry, vol. 77, No. 17, pp. 5735-5741, (2005).

Josephson, L. et al., "High-efficiency intracellular magnetic labeling with novel superparamagnetic-tat peptide conjugates", Bioconjugate Chem., vol. 10, No. 2, pp. 186-191, (1999).

Josephson, L. et al., "The effects of iron oxides on proton relaxivity", Magnetic Resonance Imaging, vol. 6, pp. 647-653, (1988).

Josephson, L. et al., "Magnetic nanosensors for the detection of oligonucleotide sequences", Angew. Chem. Int. Ed., vol. 40, No. 17, pp. 3204-3206, (2001).

Kabalka, G. et al., "Gadolinium-labeled liposomes: Targeted MR contrast agents for the liver and spleen", Radiology, vol. 163, pp. 255-258, (1987).

Kooi, M.E. et al., "Accumulation of ultrasmall superparamagnetic particles of iron oxide in human atherosclerotic plaques can be detected by in vivo magnetic resonance imaging", Circulation, vol. 107, pp. 2453-2458, (2003).

Kresse, M. et al., "Targeting of ultrasmall superparamagnetic iron oxide (USPIO) particles to tumor cells in vivo by using transferring receptor pathways", Magn. Reson. Med., vol. 40, pp. 236-242, (1998).

Lee, J. et al., "A steroid-conjugated contrast agent for magnetic resonance imaging of cell signaling", Journal of American Chemical Society, vol. 127, No. 38, pp. 13164-13166, (2005).

Lewin, M. et al., "Tat peptide-derivatized magnetic nanoparticles allow in vivo tracking and recovery of progenitor cells", Nature Biotechnology, vol. 18, pp. 410-414, (2000).

Li, J.J. et al., "Molecular aptamer beacons for real-time protein recognition", Biochemical and Biophysical Research Communications, vol. 292, No. 1, pp. 31-40, (2002).

Li, W-H. et al., "A calcium-sensitive magnetic resonance imaging contrast agent", Journal of the American Chemical Society, vol. 121, No. 6, pp. 1413-1414, (1999).

Lin, C.H. et al., "Structural basis of DNA folding and recognition in an AMP-DNA aptamer complex: distinct architectures but common recognition motifs for DNA and RNA aptamers complexed to AMP", Chemistry and Biology, vol. 4, pp. 817-832, (1997).

Liss, M. et al., "An aptamer-based quartz crystal protein biosensor", Analytical Chemistry, vol. 74, No. 17, pp. 4488-4495, (2002).

Liu, Y. et al., "Aptamer-directed self-assembly of protein arrays on a DNA nanostructure", Angew. Chem. Int. Ed., vol. 44, pp. 4333-4338, (2005).

Macaya, R.F. et al., "Thrombin-binding DNA aptamer forms a unimolecular quadruplex structure in solution", Proceedings of the National Academy of Science USA, vol. 90, pp. 3745-3749, (1993).

Nagel-Wolfrum, K. et al., "The interaction of specific peptide aptamers with the DNA binding domain and the dimerization domain of the transcription factor stat3-inhibits transactivation and induces apoptosis in tumor cells", Molecular Cancer Research, vol. 2, pp. 170-182, (2004).

Nitin, N. et al., "Functionalization and pepride-based delivery of magnetic nanoparticles as an intracellular MRI contrast agent", J. Biol. Inorg. Chem., vol. 9, pp. 706-712, (2004).

Nutiu, R. et al., "Engineering DNA aptamers and DNA enzymes with fluorescence-signaling properties", Pure Appl. Chem., vol. 76, Nos. 7-8, pp. 1547-1561, (2004).

Padmanabhan, K. et al., "The structure of a-thrombin inhibited by a 15-mer single-stranded DNA aptamer", The Journal of Biological Chemistry, vol. 268, No. 24, pp. 17651-17654, (1993).

Pavlov, V. et al., "Aptamer-functionalized au nanoparticles for the amplified optical detection of thrombin", The Journal of the American Chemical Society, vol. 126, No. 38, pp. 11768-11769, (2004).

Pendergrast, P.S. et al., "Nucleic acid aptamers for target validation and therapeutic applications", Journal of Biomolecular Techniques, vol. 16, issue 3, pp. 224-234, (2005).

Perez, J.M. et al., "Use of magnetic nanoparticles as nanosensors to probe for molecular interactions", ChemBioChem, vol. 5, pp. 261-264, (2004).

Perez, J.M. et al., "Viral-induced self-assembly of magnetic nanoparticles allows the detection of viral particles in biological media", Journal of the American Chemical Society, vol. 125, No. 34, pp. 10192-10193, (2003).

Radi, A-E. et al., "Reagentless, reusable, ultrasensitive electrochemical molecular beacon aptasensor", Journal of the American Chemical Society, vol. 128, No. 1, pp. 117-124, (2006).

Saeed, M. et al., "Occlusive and reperfused myocardial infarcts: differentiation with Mn-DPDP-enhanced MR imaging", Radiology, vol. 172, pp. 59-64, (1989).

Shen, T. et al., "Monocrystalline iron oxide nanocompounds (MION): Physicochemical properties", Magn. Reson. Med., vol. 29, pp. 599-604, (1993).

Soriaga, M.P. et al., "Determination of the orientation of adsorbed molecules at solid-liquid interfaces by thin-layer electrochemistry: Aromatic compounds at platinum electrodes", Journal of the American Chemical Society, vol. 104, pp. 2735-2742, (1982).

Soriaga, M.P. et al., "Determination of the orientation of aromatic molecules adsorbed on platinum electrodes: The influence of iodide a surface-active anion", Journal of the American Chemical Society, vol. 104, pp. 2742-2747, (1982).

Soriaga, M.P. et al., "Determination of the orientation of aromatic molecules adsorbed on platinum electrodes: The effect of solute concentration", Journal of the American Chemical Society, vol. 104, pp. 3937-3945, (1982).

Sosnovik, D.E. et al., "Emerging concepts in molecular MRI", Current Opinion in Biotechnology, vol. 18, pp. 4-10, (2007).

Taboada, E. et al., "Relaxometric and magnetic characterization of ultrasmall iron oxide nanoparticles with high magnetization. Evaluation as potential $T_1$ magnetic resonance imaging contrast agents for molecular imaging", Langmuir, vol. 23, No. 8, pp. 4583-4588, (2007).

Tasset, D.M. et al., "Oligonucleotide inhibitors of human thrombin that bind distinct epitopes", J. Mol. Biol., vol. 272, pp. 688-698, (1997).

Tian, Y. et al., "DNAzyme amplification of molecular beacon signal", Talanta, vol. 67, pp. 532-537, (2005).

Tompkins, H.G. et al., "The study of the gas-solid interaction of acetic acid with a cuprous oxide surface using reflection-absorption spectroscopy", Journal of colloid and interface science, vol. 49, No. 3, pp. 410-421, (1974).

Tsourkas, A. et al., "Magnetic relaxation switch immunosensors detect enantiomeric impurities", Angew. Chem. Int. Ed., vol. 43, pp. 2395-2399, (2004).

Wang, S. et al., "Core/shell quantum dots with high relaxivity and photoluminescence for multimodality imaging", Journal of the American Chemical Society, vol. 129, No. 13, pp. 3848-3856, (2007).

Weissleder, R. et al., "MR imaging of splenic metastases: Ferrite-enhanced detection in rats", American Journal Roentgenol., vol. 149, pp. 723-726, (1987).

Xiao, Y. et al., "Label-free electronic detection of thrombin in blood serum by using an aptamer-based sensor", Angew. Chem. Int. Ed., vol. 44, pp. 5456-5459, (2005).

Xiao, Y. et al., "A reagentless signal-on architecture for electronic, aptamer-based sensors via target-induced strand displacement", Journal of the American Chemical Society, vol. 127, No. 51, pp. 17990-17991, (2005).

Xu, D. et al., "Label-free electrochemical detection for aptamer-based array electrodes", Analytical Chemistry, vol. 77, No. 16, pp. 6218-6224, (2005).

Yamamoto, R. et al., "Molecular beacon aptamer fluoresces in the presence of Tat protein of HIV-1", Genes to Cells, vol. 5, pp. 389-396, (2000).

Zhao, M. et al., "Magnetic sensors for protease assays", Angew. Chem. Int. Ed., vol. 42, No. 12, pp. 1375-1378, (2003).

Zhao, M. et al., "Differential conjugation of tat peptide to superparamagnetic nanoparticles and its effect on cellular uptake", Bioconjugate Chem., vol. 13, pp. 840-844, (2002).

Liu, J. et al., "Colorimetric $Cu^{2+}$ with a ligation DNAzyme and nanoparticles", Chemical Communications, Advance Articles, DOI: 10.1039/b712421j, 6 pages, Oct. 24, 2007.

Liu, J. et al., "Non-Base pairing DNA provides a new dimension for controlling aptamer-linked nanoparticles and sensors", Journal of the American Chemical Society, vol. 129, No. 27, pp. 8634-8643, (2007).

Liu, J. et al., Supporting Information for "Colorimetric $Cu^{2+}$ detection with a ligation DNAzyme and nanoparticles", Chemical Communications, Advance Articles, 4 pages, Oct. 24, 2007.

Stratagene Catolog, "Gene Characterization Kits", 2 pages, (1988).

Fahlman, R.P. et al., "DNA conformational switches as sensitive electronic sensors of analytes", Journal of the American Chemical Society, vol. 124, 4610-4616, (2002).

Mayer, G. et al., "High-throughput-compatible assay for glmS riboswitch metabolite dependence", ChemBioChem, vol. 7 pp. 602-604, (2006).

Elowe, N., et al., "Small-molecule screening made simple for a difficult target with a signaling nucleic acid aptamer that reports on deaminase activity", Angew. Chem. Int. Ed., vol. 45, pp. 5648-5652, (2006).

Yigit, M. et al., "Smart "turn-on" magnetic resonance contrast agents based on aptamer-functionalized superparamagnetic iron oxide nanoparticles", ChemBioChem, vol. 8, pp. 1675-1678, (2007).

Xu, D. et al., "Label-free electrochemical detection for aptamer-based array electrodes", Analytical Chemistry, vol. 77, No. 16, pp. 5107-5113, (2005).

Yigit, M et al., "MRI detection of thrombin with aptamer functionalized superparamagnetic iron oxide nanoparticles", Bioconjugate Chem., vol. 19, pp. 412-417, (2008).

International Search Report dated Mar. 4, 2009 for PCT application No. PCT/US2008/070177.

International Search Report dated Apr. 17, 2009 for PCT application No. PCT/US2008/051185.

International Search Report dated Aug. 13, 2009 for PCT application No. PCT/US2008/072327.

Liu, J. et al., "Rational design of turn-on allosteric DNAzyme catalytic beacons for aqueous mercury ions with ultrahigh sensitivity and selectivity", Angewandte Chemmie. International Edition, vol. 46, No. 40, pp. 7587-7590, (2007).

Stadler, B. et al., "Micropatterning of DNA-tagged vesicles", Langmuir, vol. 20, No. 26, pp. 11348-11354, (2004).

Pfeiffer, I. et al., "Bivalent cholesterol-Based coupling of oligonucleotides to lipid membrane assemblies", Journal of the American Chemical Society, vol. 126, No. 33, pp. 10224-10225, (2004).

Shin, J. et al., "Acid-triggered release via dePEGylation of DOPE liposomes containing acid-labile vinyl ether PEG-lipids", Journal of Controlled Release, vol. 91, issues 1-2, pp. 187-200, (2003).

Cram, D.J. et al., "Organic Chemistry", Mcgraw-Hill, pp. 560-569, (1959).

Rusconi, C.P. et al., "Antidote-mediated control of an anticoagulant aptamer in vivo", Nature Biotechnology Letters, vol. 22, No. 11, pp. 1423-1428, (2004).

Willis M.C. et al., "Liposome-anchored vascular endothelial growth factor aptamers", Bioconjugate Chem., vol. 9, No. 5, pp. 573-582, (1998).

Healy, J.M. et al., "Pharmacokinetics and biodistribution of novel aptamer compositions", Pharm. Research, vol. 21, No. 12, pp. 2234-2246, (2004).

Farokhzad, O.C. et al., "Targeted nanoparticle-aptamer bioconjugates for cancer chemotherapy in vivo", Proceedings of the National Academy of Science, vol. 103, No. 16, pp. 6315-6320, (2006).

Farokhzad, O.C. et al., "Nanopartide-aptamer bioconjugates: A new approach for targeting prostate cancer cells", Cancer Research, vol. 64, pp. 7668-7672, (2004).

American Cancer Society Statistics for 2006. http://www.cancer.org/docroot/stt/stt_0.asp 2006.

Eifel, P. et al., "National Institutes of Health Consensus Development Panel, National Institutes of Health Consensus Development Conference statement: Adjuvant therapy for breast cancer, Nov. 1-3, 2000", Journal of the National Cancer Institute, vol. 93, No. 13, pp. 979-989, (2001).

Park, J.W. et al., "Tumor targeting using anti-her2 immunoliposomes", Journal of Controlled Release, vol. 74, pp. 95-113, (2001).

Kallab, V. et al., "HER2/EGFR internalization: a novel biomarker for ErbB-targeted therapeutics", Breast Cancer Research Treat., vol. 88, pp. S126-S127, (2004).

Wilson, K.S. et al., "Differential gene expression patterns in HER2/neu-positive and -negative breast cancer cell lines and tissues", American Journal of Pathology, vol. 161, No. 4, pp. 1171-1185, (2002).

Weigelt, B. et al., "Breast cancer metastasis: Markers and models", Nature Reviews, Cancer, vol. 5, pp. 591-602, (2005).

Pegram, M.D. et al., "Rational combinations of trastuzumab with chemotherapeutic drugs used in the treatment of breast cancer", Journal of the National Cancer Institute, vol. 96, No. 10, pp. 739-749, (2004).

Kirpotin, D.B. et al., "Antibody targeting of long-circulating lipidic nanoparticles does not increase tumor localization but does increase internalization in animal models", Cancer Research, vol. 66, No. 13, pp. 6732-6740, (2006).

Cheng, C. et al., "Formulation of Functionalized PLGA-PEG Nanoparticles for In Vivo Targeted Drug Delivery", Biomaterials, vol. 28, issue 5, pp. 869-876, (2007).

Bass, B.L. et al., "Specific interaction between the self-splicing RNA of Tetrahymena and its guanosine substrate: implications for biological catalysis by RNA", Nature, vol. 308, pp. 820-826, (1984).

Ellington, A.D. et al., "Combinatorial methods: aptamers and aptazymes", Part of the SPIE Conference on Advanced Materials and Opitical Systems for Chemical and Biological Detection, SPIE, vol. 3858, pp. 126-134, (1999).

Robertson, M.P. et al., "Aptazymes as generalized signal transducers", Nucleic Acids Symp. Ser., vol. 41, pp. 1-3, (1999).

Pagratis, N.C. et al., "Potent 2'-amino-, and 2'-fluoro-2'-deoxyribonucleotide RNA inhibitors of keratinocyte growth factor", Nature Biotechnology, vol. 15, pp. 68-73, (1997).

Lupold, S.E. et al., "Identification and characterization of nuclease-stabilized RNA molecules that bind human prostate cancer cells via the prostate-specific membrane antigen", Cancer research, vol. 62, pp. 4029-4033, (2002).

Jenison, R.D. et al., "Oligonucleotide inhibitors of P-selectin-dependent neutrophil-platelet adhesion", Antisense Nucleic Acid Drug Dev., vol. 8, pp. 265-279, (1998).

Hicke, B.J. et al., "DNA aptamers block L-selectin function in vivo. Inhibition of human lymphocyte trafficking in SCID mice", J. Clinical Invest., vol. 98, No. 12, pp. 2688-2692, (1996).

O'Connell, D. et al., "Calcium-dependent oligonucleotide antagonists specific for L-selectin", Proceedings of the National Academy of Science, U.S.A., vol. 93, pp. 5883-5887, (1996).

Soukup, G.A. et al., "Design of allosteric hammerhead ribozymes activated by ligand-induced structure stabilization", Structure, vol. 7, pp. 783-791, (1999).

Straubinger, R.M. et al., "Preparation and characterization of taxane-containing liposomes", Methods in Enzymology, vol. 391, pp. 97-117, (2005).

Rivera, E. "Liposomal anthracyclines in metastatic breast cancer: Clinical update", The Oncologist, vol. 8, supplement 2, pp. 3-9, (2003).

Kornblith, P. et al., "Breast cancer—Response rates to chemotherapeutic agents studied in vitro", Anticancer Research, vol. 23, pp. 3405-3411, (2003).

Pei, J. et al., "Combination with liposome-entrapped, ends-modified raf antisense oligonucleotide (LErafAON) improves the anti-tumor efficacies of cisplatin, epirubicin, mitoxantrone, docetaxel and gemcitabine", Anti-Cancer Drugs, vol. 15, pp. 243-253, (2004).

Allen, T.M. et al., "Therapeutic opportunities for targeted liposomal drug delivery", Advanced Drug Delivery Reviews, vol. 21, pp. 117-133, (1996).

Hofheinz, R.D. et al., "Liposomal encapsulated anti-cancer drugs", Anti-Cancer Drugs, vol. 16, pp. 691-707, (2005).

Schluep, T. et al., "Preclinical efficacy of the camptothecin-polymer conjugate IT-101 in multiple cancer models", Clinical Cancer Research, vol. 12, No. 5, pp. 1606-1614, (2006).

Schluep, T. et al., "Pharmacokinetics and biodistribution of the camptothecin-polymer conjugate IT-101 in rats and tumor-bearing mice", Cancer Chemoth. Pharm., vol. 57, pp. 654-662, (2006).

Cheng, J. et al., "Antitumor Activity of beta-Cyclodextrin Polymer-Camptothecin Conjugates", Molecular Pharmaceutics, vol. 1, No. 3, pp. 183-193, (2004).

Cheng, J. et al., "Synthesis of linear, beta-cyclodextrin-based polymers and their camptothecin conjugates", Bioconjugate Chem., vol. 14, pp. 1007-1017, (2003).

Guo, X. et al., "Steric stabilization of fusogenic liposomes by a low-pH sensitive PEG-diortho ester-lipid conjugate", Bioconjugate Chem., vol. 12, pp. 291-300, (2001).

Gerasimov, O.V. et al., "Cytosolic drug delivery using pH- and light-sensitive liposomes", Advanced Drug Delivery Reviews., vol. 38, pp. 317-338, (1999).

Rovira-Bru, M. et al., "Size and structure of spontaneously forming liposomes in lipid/PEG-lipid mixtures", Biophysical Journal, vol. 83, pp. 2419-2439, (2002).

Liu, J. et al., "Proofreading and error removal in a nanomaterial assembly", Angewandte Chemie, International Edition, vol. 44, pp. 7290-7293, (2005).

Liu, J. et al., "Design of asymmetric DNAzymes for dynamic control of nanoparticle aggregation states in response to chemical stimuli", Organic & Biomolecular Chemistry, vol. 4, pp. 3435-3441, (2006).

Cho, H.S. et al., "Structure of the extracellular region of HER2 alone and in complex with the Herceptin Fab", Nature, vol. 421, pp. 756-760, (2003).

Leahy, D.J. et al., "A Mammalian Expression Vector for Expression and Purification of Secreted Proteins for Structural Studies", Protein Expression and Purification, vol. 20, pp. 500-506, (2000).

Bartel, D.P. et al., "Isolation of new ribozymes from a large pool of random sequences", Science, vol. 261, pp. 1411-1418, (1993).

Jellinek, D. et al., "Inhibition of receptor binding by high-affinity RNA ligands to vascular endothelial growth factor", Biochemistry, vol. 33, pp. 10450-10456, (1994).

Jellinek, D. et al., "Potent 2'-Amino-2'-deoxypyrimidine RNA Inhibitors of Basic Fibroblast Growth Factor", Biochemistry, vol. 34, pp. 11363-11372, (1995).

Green, L.S. et al., "Inhibitory DNA Ligands to Platelet-Derived Growth Factor B-Chain", Biochemistry, vol. 35, pp. 14413-14424, (1996).

Lee, T.C. et al., "Overexpression of RRE-derived sequences inhibits HIV-1 replication in CEM cells", New Biologist, vol. 4, p. 66, (1992).

Andresen, T.L. et al., "Advanced strategies in liposomal cancer therapy: Problems and prospects of active and tumor specific drug release", Progress in Lipid Research, vol. 44, pp. 68-97, (2005).

Woodle, M.C. et al., "Sterically Stabilized Liposomes—Reduction in electrophoretic mobility but not electrostatic surface potential", Biophysical Journal, vol. 61, pp. 902-910, (1992).

Zalipsky, S. et al., "Long Circulating, Cationic Liposomes Containing Amino-Peg-Phosphatidylethanolamine", FEBS Letters, vol. 353, pp. 71-74, (1994).

Morrison, W., "A fast, simple and reliable method for the microdetermination of phosphorus in biological materials", Analytical Biochemistry, vol. 7, issue 2, pp. 218-224, (1964).

Kirpotin, D. et al., "Sterically Stabilized Anti-HER2 Immunoliposomes: Design and Targeting to Human Breast Cancer Cells in Vitro", Biochemistry, vol. 36, pp. 66-75, (1997).

Klibanov, A.L. et al., "Activity of Amphipathic Poly(Ethylene Glycol)-5000 to Prolong the Circulation Time of Liposomes Depends on the Liposome Size and Is Unfavorable for Immunoliposome Binding to Target", Biochim. Biophys. Acta, vol. 1062, pp. 142-148, (1991).

Park, J.W. et al., "Development of Anti-P185$^{HER2}$ Immunoliposomes for Cancer-Therapy", Proceedings of the National Academy of Science U.S.A., vol. 92, pp. 1327-1331, (1995).

Zalipsky, S. "Synthesis of an End-Group Functionalized Polyethylene Glycol-Lipid Conjugate for Preparation of Polymer-Grafted Liposomes", Bioconjugate Chem., vol. 4, pp. 296-299, (1993).

Allen, T.M. et al., "A New Strategy for Attachment of Antibodies to Sterically Stabilized Liposomes Resulting in Efficient Targeting to Cancer-Cells", Biochimica et Biophysica Acta, vol. 1237, pp. 99-108, (1995).

Gillies, E.R. et al., "A new approach towards acid sensitive copolymer micelles for drug delivery", Chemical Communications, Issue 14, pp. 1640-1641, (2003).

Joensuu, O.I., "Fossil Fuels as a Source of Mercury Pollution", Science, vol. 172, No. 3987, pp. 1027-1028, (1971).

Maim, O., "Gold mining as a source of mercury exposure in the Brazilian Amazon", Environmental Research, vol. 77, No. 2, pp. 73-78, (1998).

Tchounwou, P.B. et al., "Environmental exposure to mercury and its toxicopathologic implications for public health", Environmental Toxicology, vol. 18, No. 3, pp. 149-175, (2003).

Yoon, S. et al., "A bright and specific fluorescent sensor for mercury in water, cells, and tissue", Angewandte Chemie International Edition, vol. 46, No. 35, pp. 6658-6661, (2007).

Liu, X.F. et al., "Optical detection of mercury(II) in aqueous solutions by using conjugated polymers and label-free oligonucleotides", Advanced Materials, vol. 19, No. 11, p. 1471, (2007).

Chiang, C.K. et al., "Oligonucleotide-based fluorescence probe for sensitive and selective detection of mercury(II) in aqueous solution", Analytical Chemistry, vol. 80, No. 10, pp. 3716-3721, (2008).

Yamini, Y. et al., "Solid phase extraction and determination of ultra trace amounts of mercury(II) using octadecyl silica membrane disks modified by hexathia-18-crown-6-tetraone and cold vapour atomic absorption spectrometry", Analytica Chimica Acta, vol. 355, issue 1, pp. 69-74, (1997).

Darbha, G.K. et al., "Gold nanoparticle-based miniaturized nanomaterial surface energy transfer probe for rapid and ultrasensitive detection of mercury in soil, water, and fish", Acs Nano, vol. 1, No. 3, pp. 208-214, (2007).

Li, D. et al., "Optical analysis of Hg2+ ions by oligonucleotide-gold-nanoparticle hybrids and DNA-based machines", Angewandte Chemie International Edition, vol. 47, No. 21, pp. 3927-3931, (2008).

Liu, C.W. et al., "Detection of mercury(II) based on Hg2+-DNA complexes inducing the aggregation of gold nanoparticles", Chemical Communications, vol. 19, pp. 2242-2244, (2008).

Xue, X. et al., "One-step, room temperature, colorimetric detection of mercury (Hg2+) using DNA/nanoparticle conjugates", Journal of the American Chemical Society, vol. 130, No. 11, pp. 3244-3245, (2008).

Wang, L. et al., "Gold nanoparticle-based optical probes for target-responsive DNA structures", Gold Bulletin, vol. 41, No. 1, pp. 37-41, (2008).

Clarkson, T.W. et al., "Mercury—Major Issues in Environmental-Health", Environmental Health Perspectives, vol. 100, pp. 31-38, (1993).

Wren, C.D. "A Review of Metal Accumulation and Toxicity in Wild Mammals, 1 Mercury", Environmental Research, vol. 40, No. 1, pp. 210-244, (1986).

Koos, B.J. et al., "Mercury Toxicity in Pregnant Woman, Fetus, and Newborn-Infant—Review", American Journal of Obstetrics and Gynecology, vol. 126, No. 3, pp. 390-409, (1976).

Yu, Y. et al., "p-dimethylaminobenzaldehyde thiosemicarbazone: A simple novel selective and sensitive fluorescent sensor for mercury(II) in aqueous solution", Talanta, vol. 69, No. 1, pp. 103-106, (2006).

Braman, R.S., "Membrane Probe—Spectral Emission Type Detection System for Mercury in Water", Analytical Chemistry, vol. 43, No. 11, pp. 1462-1467, (1971).

Wernette, D.P. et al., "Surface immobilization of catalytic beacons based on ratiometric fluorescent DNAzyme sensors: a systematic study", Langmuir, vol. 23, No. 18, pp. 9513-9521, (2007).

Wang, Z. et al., "Highly sensitive "turn-on" fluorescent sensor for Hg2+ in aqueous solution based on structure-switching DNA", Chemical Communications, pp. 6005-6007, (2008).

Lu, Y. "New catalytic DNA fluorescent and colorimetric sensors for on-sit and real-time monitoring of industrial and drinking water", ISTC Reports, Illinois Sustainable Technology Center Institute of Natural Resource Sustainability, University of Illinois at Urbana-Champaign, http://www.istc.illinois.edu/info/library_docs/RR/RR-114.pdf, pp. i-ix, and 1-30, (2009).

Turner, A. P. F., "Biochemistry: Biosensors—Sense and Sensitivity", Science, vol. 290, No. 5495, pp. 1315-1317, (2000).

Abbasi, S. A., "Atomic absorption spectrometric and spectrophotometric trace analysis of uranium in environmental samples with n-p-methoxyphenyl-2-4-(2-pyridylazo) resorcinol", Int. J. Environ. Anal. Chem., vol. 36, pp. 163-172, (1989).

Arnez, J. G. et al., "Crystal structure of unmodified tRNA$^{Gln}$ complexed with glutaminyl-tRNA synthetase and ATP suggests a possible role for pseudo-uridines in stabilization of RNA structure", Biochemistry, vol. 33, pp. 7560-7567, (1994).

Blake, R. C., II, et al., "Novel monoclonal antibodies with specificity for chelated uranium (VI): isolation and binding properties", Bioconjug. Chem., vol. 15, pp. 1125-1136, (2004).

Boomer, D. W., et al, "Determination of uranium in environmental samples using inductively coupled plasma mass spectrometry", Anal. Chem., vol. 59, pp. 2810-2813, (1987).

Breaker, R. R., "Natural and engineered nucleic acids as tools to explore biology", Nature, vol. 432, pp. 838-845, (2004).

Brina, R. et al., "Direct detection of trace levels of uranium by laser-induced kinetic phosphorimetry", Anal. Chem., vol. 64, pp. 1413-1418, (1992).

Chung N. et al., "Selective extraction of gold(III) in the presences of Pd(II) and Pt(IV) by saltin-out of the mixture of 2-propanol and water", Talanta, vol. 58, pp. 927-933, (2002).

Craft, E. et al., "Depleted and natural uranium: chemistry and toxicological effects", J. Toxicol. Environ. Health, Part B, vol. 7, pp. 297-317, (2004).

Demers, L. M. et al., "Thermal desorption behavior and binding properties of DNA bases and nucleosides on gold", J. Am. Chem. Soc. vol. 124, pp. 11248-11249, (2002).

Frankforter G. et al., "Equilibria in the systems of the higher alcohols, water and salts", J. Am. Chem. Soc., vol. 37, pp. 2697-2716 (1915).

Frankforter G., et al., "Equilibria in the systems, water, acetone and inorganic salts", J. Am. Chem. Soc., vol. 36, pp. 1103-1134, (1914).

Frankforter G., et al., "Equilibria in systems containing alcohols, salts and water, including a new method of alcohol analysis", J. Phys. Chem., vol. 17, pp. 402-473, (1913).

Ginnings, P. et al., "Ternary systems: water, tertiary butanol and salts at 30° C.", J. Am. Chem. Soc., vol. 52, pp. 2282-2286, (1930).

Gongalsky, K., "Impact of pollution caused by uranium production on soil macrofauna", Environ. Monit. Assess., vol. 89, pp. 197-219, (2003).

Homola, J. et al., "Surface Plasmon Resonance (SPR) Sensors", Springer Series on Chemical Sensors and Biosensors, vol. 4, pp. 45-67, (2006).

US EPA, "Drinking water contaminants", found at http://www.epa.gov/safewater/contaminants/index.html, pp. 1-17, printed on Nov. 23, 2009.

Jones, L. A., et al., "Extraction of phenol and its metabolites from aqueous solution", J. Agric. Food Chem., vol. 41, pp. 735-741, (1993).

Katz, E. et al., "Integrated nanoparticle-biomolecule hybrid systems: sythesis, properties, and applications", Angew. Chem. Int. Ed., vol. 43, pp. 6042-6108, (2004).

Kobe, K. A. et al., "The ternary systems ethylene glycol-potassium carbonate-water and dioxane-potassium carbonate-water", J. Phys. Chem., vol. 446, pp. 629-633, (1940).

Laromaine, A. et al., "Protease-triggered dispersion of nanoparticle assemblies", J. Am. Chem. Soc., vol. 129, pp. 4156-4157, (2007).

Lazarova, Z. et al., "Solvent extraction of lactic acid from aqueous solution", Journal of Biotechnology, vol. 32, pp. 75-82, (1994).

Lee, J. H. et al., "Site-specific control of distances between gold nanoparticles using phosphorothioate anchors on DNA and a short bifunctional molecular fastener", Angew. Chem. Int. Ed., vol. 46, pp. 9006-9010, (2007).

Leggett, D. C. et al., "Salting-out solvent extraction for preconcentration of neutral polar organic solutes from water", Anal. Chem., vol. 62, pp. 1355-1356, (1990).

Leinonen, H., "Stress corrosion cracking and life prediction evaluation of austenitic stainless steels in calcium chloride solution", Corrosion Science, vol. 52, No. 5, pp. 337-346, (1996).

Li, D. et al., "Amplified electrochemical detection of DNA through the aggregation of Au nanoparticles on elctrodes and the incorporation of methylene blue into the DNA-crosslinked structure", Chem. Comm., pp. 3544-3546, (2007).

Li, H. et al., "Detection of specific sequences in rna using differential adsorption of single-stranded oligonucleotides on gold nanoparticles", Anal. Chem., vol. 77 No. 19, pp. 6229-6233, (2005).

Li, H. et al., "Colorimetric detection of dna sequences based on electrostatic interactions with unmodified gold nanoparticles", Proc. Natl. Acad. Sci. U.S.A., vol. 101, pp. 14036-14039, (2004).

Li, H. et al., "Label-free colorimetric detection of specific sequences in genomic dna amplified by the polymerase chain reaction", J. Am. Chem. Soc., vol. 126, pp. 10958-10961, (2004).

Likidis, Z. et al., "Recovery of penicillin G from fermentation broth with reactive extraction in a mixer-settler", Biotechnology Letters, vol. 9, No. 4, pp. 229-232, (1987).

Lim, I. et al., "Homocysteine-mediated reactivity and assembly of gold nanoparticles", Langmuir, vol. 23, pp. 826-833, (2007).

Lu, Y. et al., "Functional DNA nanotechnology:emerging applications of DNAzymes and aptamers", Curr. Opion. Biotech., vol. 17, pp. 580-588, (2006).

Long, F. A., et al., "Activity coefficients of nonelectrolyte solutes in aqueous salt solutions", Chem. Rev., vol. 51, pp. 119-169, (1952).

Lu, X. et al., "Salting-out separation and liquid-liquid equilibrium of tertiary butanol aqueous solution", Chemical Engineering Journal, vol. 78, pp. 165-171, (2000).

Lu, Y. et al., "Smart nanomaterials inspired by biology: dynamic assembly of error-free nanomaterials in response to multiple chemical and biological stimuli", Accounts of Chemical Research, vol. 40, pp. 315-323, (2007).

Mlakar, M. et al., "Stripping voltammetric determination of trace levels of uranium by synergic adsorptions", Analytica Chimica Acta, vol. 221, pp. 279-287, (1989).

Nishihama, S., "Review of advanced liquid-liquid extraction systems for the separation of metal ions by a combination of conversion of the metal species with chemical reaction", Ind. Eng. Chem. Res., vol. 40, pp. 3085-3091, (2001).

Pierotti, R. A., "A scaled particle theory of aqueous and nonaqueous solutions", Chemical Reviews, vol. 76, No. 6, pp. 717-726, (1976).

Centers for Disease Control, "Preventing lead poisoning in young children", U.S. Department of Health and Human Services, Public Health Service, Centers for Disease Control: Atlanta, GA, (1991).

Public Law 102-550; Residential Lead-Based Paint Hazard Reduction Act of the housing and Community Development Act of 1992; 28 pages, (1992).

Qiang, Z. et al., "Potentiometric determination of acid dissociation constants ($pK_a$) for human and veterinary antibotics", Water Research, vol. 38, pp. 2874-2890, (2004).

Rohwer, H. et al., "Interactions of uranium and thorium with arsenazo III in an aqueous medium", Analytica Chimica Acta, vol. 341, pp. 263-268, (1997).

Safavi, A. et al., "A novel optical sensor for uranium determination", Analytica Chimica Acta vol. 530, pp. 55-60, (2005).

Sato, K. et al., "Rapid aggregation of gold nanoparticles induced by non-cross-linking DNA hybridization", J. Am. Chem. Soc., vol. 125, pp. 8102-8103, (2003).

Schenk, F. J. et. al., "Comparison of magnesium sulfate and sodium sulfate for removal of water from pesticide extracts of foods", J. AOAC International, vol. 85, No. 5, pp. 1177-1180, (2002).

Sessler, J. L. et al., "Hexaphyrin (1.0.1.0.0.0). a new colorimetric actinide sensor", Tetrahedron, vol. 60, pp. 11089-11097, (2004).

Shafer-Peltier, K. E. et al., "Toward a glucose biosensor based on surface-enhanced raman scattering", J. Am. Chem. Soc., vol. 125, pp. 588-593, (2003).

Sharma, J. et al., "DNA-templated self-assembly of two-dimensional and periodical gold nanoparticle arrays", Angew. Chem. Int. Ed., vol. 45, pp. 730-735, (2006).

Si, S. Et al., "pH-controlled reversible assembly of peptide-functionalized gold nanoparticles", Langmuir, vol. 23, pp. 190-195, (2007).

Simard, J. et al., "Formation and pH-controlled assembly of amphiphilic gold nanoparticles", Chemical Commun., pp. 1943-1944, (2000).

Singleton, V. L., "An extraction technique for recovery of flavors, pigments, and other constituents from wines and other aqueous solutions", Am. J. Enol. Vitic., vol. 12, pp. 1-8, (1961).

Rao, C.V.S.R. et al., "Extraction of acetonitrile from aqueous solutions. 1. Ternary liquid equilibria", Journal of Chemical and Engineering Data, vol. 23, No. 1, pp. 23-25, (1978).

Rao, D.S. et al., "Extraction of acetonitrile from aqueous solutions. 2. ternary liquid equilibria", Journal of Chemical and Engineering Data, vol. 24, No. 3, pp. 241-244, (1979).

Tabata, M. et al., "Ion-pair extraction of metalloporphyrins into acetonitrile for determination of copper(II)", Analytical Chemistry, vol. 68, No. 5, pp. 758-762, (1996).

Tabata, M. et al., "Chemical properties of water-miscible solvents separated by salting-out and their application to solvent extraction", Analytical sciences, vol. 10, pp. 383-388, (1994).

Van der Wal, Sj., "Low viscosity organic modifiers in reversed-phase HPLC", Chromatographia, vol. 20, No. 5, pp. 274-278, (1985).

Wang, J. et al., "A gold nanoparticle-based aptamer target binding readout for ATP assay", Adv. Mater., vol. 19, pp. 3943-3946, (2007).

Wang, L. et al., "Unmodified gold nanoparticles as a colorimetric probe for potassium DNA aptamers", Chem. Comm., vol. 36, 3780-3782, (2006).

Wang, Z. et al., "Label-free colorimetric detection of lead ions with a nanomolar detection limit and tunable dynamic range by using gold nanoparticles and DNAzyme", Advanced Materials, vol. 20, pp. 3263-3267. (2008).

Warren, K. W., Reduction of corrosion through improvements in desalting, Benelux Refinery Symposium, Lanaken, Belgium, 11 pages, (1995).

Wei, H. et al., "Simple and sensitive aptamer-based colorimetric sensing of protein using unmodified gold nanoparticle probes", Chem. Comm., vol. 36, pp. 3735-3737, (2007).

Wernette, D. P. et al., "Surface immobilization of catalytic beacons based on ratiometric fluorescent DNAzyme sensors: A systematic study", Langmuir, vol. 23, pp. 9513-9521, (2007).

Willner, I. et al., "Electronic aptamer-based sensors", Angew. Chem., Int. Ed., vol. 46, pp. 6408-6418, (2007).

Wu, Y. G., et al., "An extended water-miscible organic Johnson-Furter equation to salting-out phase separation of aqueous solution of solvents", Fluid Phase Equilibria, vol. 192, pp. 1-12, (2001).

Yan, H., "Nucleic acid nanotechnology", Science, vol. 306, pp. 2048-2049, (2004).

Yang, W. H. et al., "Discrete dipole approximation for calculating extinction and raman intensities for small particles with arbitrary shapes", J. Chem. Phys., vol. 103, pp. 869-875, (1995).

Deng, Z. et al., "DNA-Encoded self-assembly of gold nanoparticles into one-dimensional arrays", Angew. Chem. Int. Ed., vol. 44, pp. 3582-3585, (2005).

Zhao, W. et al., "Simple and rapid colorimetric biosensors based on DNA aptamer and noncrosslinking gold naoparticle aggregation", ChemBioChem, vol. 8, pp. 727-731, (2007).

Zhao, W. et al., "Highly stabilized nucleotide-capped small gold nanoparticles with tunable size", Advanced Materials, vol. 19, pp. 1766-1771, (2007).

Zhao, W. et al., "DNA polymerization on gold nanoparticles through rolling circle amplification: towards novel scaffolds for three-dimensional periodic nanoassemblies", Angew. Chem. Int. Ed., vol. 45, pp. 2409-2413, (2006).

Zhao, W. et al., "DNA aptamer folding on gold nanoparticles: from colloid chemistry to biosensors", J. Am. Chem. Soc., vol. 130, (11), pp. 3610-3618, (2008).

Zhou, P. et al., "Extraction of oxidized and reduced forms of uranium from contaminated soils: effects of carbonate concentration pH", Environmental Science Technology, vol. 39, No. 12, pp. 4435-4440, (2005).

Jacoby, M., "Sensitive, selective mercury sensor nanoparticle-based colorimetric method detects part-per-billion levels of mercury", Chemical & Engineering News, pp. 1-3, May 2, 2007.

Cruz, R.P.G. et al., supplemental to "Dinucleotide junction cleavage versatility of 8-17 deoxyribozyme", Chemistry & Biology, vol. 11, pp. 57-67, (pp. 1-8) (2004).

Saleh, O. A. et al., "Direct detection of antibody-antigen binding using an on-chip artificial pore", Proceedings of the National Academy of Science, vol. 100, No. 3, pp. 820-824, (2003).

Han, C. et al., "Highly selective and sensitive colorimetric probes for $Yb^{3+}$ ions based on supramolecular aggregates assembled from B-cyclodextrin-4,4'-dipyridine inclusion complex modified silver nanoparticles", Chem. Commun., pp. 3545-3547, (2009).

Aldaye, F.A., et al., "Sequential Self-Assembly of a DNA Hexagon as a Template for the Organization of Gold Nanoparticles", Angew. Chem. Int. Ed., 45, pp. 2204-2209, (2006).

Loweth, C.J. et al., "DNA-Based Assembly of Gold Nanocrystals", Angew. Chem. Int. Ed., 38, No. 12, pp. 1808-1812, (1999).

Carbone, A., et al., "Circuits and programmable self-assembling DNA structures", Proceedings of the National Academy of Sciences of the United States of America, vol. 99, No. 20, pp. 12577-12582, (2002).

Chelyapov, N., et al., "DNA Triangles and Self-Assembled Hexagonal Tilings", J. Am. Chem. Soc., 126, pp. 13924-13925, (2004).

Conway, N.E., et al., "The Covalent Attachment of Multiple Fluorophores to DNA Containing Phosphorothioate Diesters Results in Highly Sensitive Detection of Single-Stranded DNA", Bioconjugate Chem, 2, pp. 452-457, (1991).

Ding, B., et al., "Pseudohexagonal 2D DNA Crystals from Double Crossover Cohesion", J. Am. Chem. Soc., 126, pp. 10230-10231, (2004).

Endo, M., et al., "DNA Tube Structures Controlled by a Four-Way-Branched DNA Connector", Angew. Chem. Int. Ed., 44, pp. 6074-6077, (2005).

Fidanza, J.A, et al. "Site-Specific Labeling of DNA Sequences Containing Phosphorothioate Diesters", J. Am. Chem. Soc., 114, pp. 5509-5517, (1992).

Goodman, R.P., et al., "Rapid Chiral Assembly of Rigid DNA Building Blocks for Molecular Nanofabrication", Science, 310, pp. 1661-1665, (2005).

Hagleitner, C., et al., "Smart single-chip gas sensor microsystem", Nature, vol. 414, pp. 293-296, (2001).

He, Y., et al., "Sequence Symmetry as a Tool for Designing DNA Nanostructures", Angew. Chem. Int. Ed., 44, pp. 6694-6696, (2005).

Heath, J.R., et al., "A Defect-Tolerant Computer Architecture: Opportunities for Nanotechnology", Science, vol. 280, pp. 1716-1719, (1998).

Holloway, G., et al., "An Organometallic Route to Oligonucleotides Containing Phosphoroselenoate", ChemBioChem, 3, pp. 1061-1065, (2002).

Li, H., et al., "DNA-Templated Self-Assembly of Protein and Nanoparticle Linear Arrays", J. Am. Chem. Soc., 126, pp. 418-419, (2004).

Cunningham, L., et al., "Spectroscopic Evidence for Inner-Sphere Coordination of Metal Ions to the Active Site of a Hammerhead Ribozyme", J. Am. Chem. Soc., 120, pp. 4518-4519, (1998).

Luduena, R.F., et al., N,N-Bis($\alpha$-iodoacetyl)-2,2'-dithiobis(ethylamine), a Reversible Crosslinking Reagent for Protein Sulfhydryl Groups, Analytical Biochemistry, 117. pp. 76-80, (1981).

Lund, K., et al., "Self-Assembling a Molecular Pegboard", J. Am. Chem. Soc., 127, pp. 17606-17607, (2005).

Mathieu, F., et al. "Six-Helix Bundles Designed from DNA", Nano Letters, vol. 5, No. 4, pp. 661-665, (2005).

Liu, H., et al, "Approaching the Limit: Can One DNA Oligonucleotide Assemble into Large Nanostructures?", Angew. Chem., 118, pp. 1976-1979, (2006).

Fidanza, J. et al, "Introduction of Reporter Groups at Specific Sites in DNA Containing Phosphorothioate Diesters", J. Am. Chem. Soc., 111, pp. 9117-9119, (1989).

Nakao, H., et al, "Highly Ordered Assemblies of Au Nanoparticles Organized on DNA", Nano Letters, vol. 3, No. 10, pp. 1391-1394, (2003).

Patolsky, F., et al., "Au-Nanoparticle Nanowires Based on DNA and Polylysine Templates", Angew. Chem. Int. Ed., 41, No. 13, pp. 2323-2327, (2002).

Pinto, Y., et al., "Sequence-Encoded Self-Assembly of Multiple-Nanocomponent Arrays by 2D DNA Scaffolding", Nano Letters, vol. 5, No. 12, pp. 2399-2402, (2005).

Rothemund, P., "Folding DNA to create nanoscale shapes and patterns", Nature, vol. 440, pp. 297-302, (2006).

Yang, X., et al, "Ligation of DNA Triangles Containing Double Crossover Molecules", J. Am. Chem. Soc., 120, pp. 9779-9786, (1998).

Seeman, N.C., "Nucleic Acid Nanostructures and Topology", Angew. Chem. Int. Ed., 37, pp. 3220-3238, (1998).

Seeman, N. C., "At the Crossroads of Chemistry, Biology, and Materials: Structural DNA Nanotechnology", Chemistry & Biology, vol. 10, pp. 1151-1159, (2003).

Le, J.D., et al., "DNA-Templated Self-Assembly of Metallic Nanocomponent Arrays on a Surface", Nano Letters, vol. 4, No. 12, pp. 2343-2347, (2004).

Seeman, N.C., et al. "Nucleic acid nanostructures: bottom-up control of geometry on the nanoscale", Reports on Progress in Physics, 68, pp. 237-270, (2005).

Warner, M.G., et al., "Linear assemblies of nanoparticles electrostatically organized on DNA scaffolds", Nature Materials, vol. 2, pp. 272-277, (2003).

Winfree, E., et al., "Design and self-assembly of two-dimensional DNA crystals", Nature, vol. 394, pp. 539-544, (1998).

Woehrle, G.H., et al., "Molecular-Level Control of Feature Separation in One-Dimensional Nanostructure Assemblies Formed by Biomolecular Nanolithography", Langmuir, 20, pp. 5982-5988, (2004).

Zhang, J., et al, "Periodic Square-Like Gold Nanoparticle Arrays Templated by Self-Assembled 2D DNA Nanogrids on a Surface", Nano Letters, vol. 6, No. 2, pp. 248-251, (2006).

Yang, T. et al. "Tunneling Phase Logic Cellular Nonlinear Networks", International Journal of Bifurcation and Chaos, vol. 11, No. 12, pp. 2895-2911, (2001).

Liu, Z., et al., "Imaging DNA Molecules on Mica Surface by Atomic Force Microscopy in Air and in Liquid", Microscopy Research and Technique, 66, pp. 179-185, (2005).

Niemeyer, C.M., et al., "Covalent DNA-Streptavidin Conjugates as Building Blocks for Novel Biometallic Nanostructures", Angew. Chem. Int. Ed., 37, No. 16, pp. 2265-2268, (1998).

"What wavelength goes with a color" from eosweb. larc. Nasa.gov. Printed on Jan. 7, 2011.

Cadmium sulfide from Wikipedia, the free encyclopedia. Printed on Jan. 7, 2011.

Yeh, et al., Quantum dot-mediated biosensing assays for specific nucleic acid detection. Nanomedicine, 1, 115-121, 2005.

Li, J., et al., "A highly sensitive and selective catalytic DNA biosensor for lead ions"., J. Am. Chem. Soc., vol. 122, No. 42, pp. 10466-10467, (2000).

Liu, J., et al., "A colorimetric lead biosensor using dnazyme-directed assembly of gold nanoparticles", Journal of the American Chemical Society, vol. 125, No. 22, pp. 6642-6643, (2003).

Lu, Y., "New transition-metal-dependent DNAzymes as efficient endonucleases and as selective metal biosensors"., Chem. Eur. J., vol. 8, No. 20, pp. 4588-4596, (2002).

Nutiu, R., et al., "Structure-switching signaling aptamers: transducing molecular recognition into fluorescence signaling", Chem. Euro. J., vol. 10, No. 8, pp. 1868-1876, (2004).

* cited by examiner

AMPHIPHILIC SUBSTANCES AND FUNCTIONALIZED LIPID VESICLES INCLUDING THE SAME

REFERENCE TO RELATED APPLICATION

This application claims the benefit of U.S. Provisional Application No. 60/885,744 entitled "AMPHIPHILIC SUBSTANCES AND FUNCTIONALIZED LIPID VESICLES INCLUDING THE SAME" filed Jan. 19, 2007, the entire contents of which are hereby incorporated by reference.

FEDERALLY SPONSORED RESEARCH OR DEVELOPMENT

The subject matter of this application may have been funded in part under a research grant from the National Science Foundation, under Grant Numbers DMR-0117792 and DMR-0409369. The U.S. Government may have rights in this invention.

BACKGROUND

Lipid vesicles have unilamellar or multilamellar exterior walls that enclose an internal space. The walls of lipid vesicles are bimolecular layers (bilayers) of one or more polar lipid components having polar heads and non-polar tails. In an aqueous liquid, or other polar liquid, the polar heads of one layer may orient outwardly to extend into the surrounding medium, the non-polar tail portions of the lipids thus associating with each other. This orientation provides a layer having a polar surface on either side of the layer, and having a non-polar core between the surfaces. In a lipid vesicle, the bilayer forms a closed structure, where both the exterior and the interior of the structure have a polar surface. Unilamellar vesicles have one such bilayer, whereas multilamellar vesicles typically have multiple, concentric bilayers.

One application of lipid vesicles is in the delivery of bioactive agents within an organism. Examples of bioactive agents include drug agents and imaging agents. Lipid vesicles may be used to isolate a bioactive agent, so as to direct the agent away from certain tissues and to deliver the agent to other tissues. Lipid vesicles also can be used to release drugs over a prolonged period of time, allowing for less frequent administration. In addition, lipid vesicles can allow for delivery of hydrophobic or amphiphilic drugs that would otherwise be difficult to administer by injection.

In one example of bioactive agent delivery, lipid vesicles have been researched for use with chemotherapeutic agents. Tumor-specific drug delivery has become an important area of research in cancer therapy. Application of chemotherapeutics for cancer treatment is often limited by severe side effects and poor systemic efficacy. Lipid vesicle delivery systems have decreased these pharmacokinetic drawbacks, resulting in a number of delivery systems for cancer treatment that have been approved by the U.S. Food & Drug Administration (FDA). These approved liposome delivery systems, however, release the encapsulated agent through passive diffusion from the vesicle or through slow, non-specific degradation of the vesicle. These mechanisms can lead to systemic toxicity and also lack the ability to actively release the encapsulated agent at a specific disease site and/or at a specific time.

At present, most lipid vesicle mediated bioactive agent delivery is either untargeted or passively targeted. Passive targeting involves stabilizing the lipid vesicle against degradation in the circulatory system, providing for an increase in blood circulation times. A typical approach to this stabilization is to coat the lipid vesicle with a hydrophilic polymer, such as poly(ethylene glycol) (PEG). A common drawback to the untargeted or passively targeted strategies is the lack of accuracy in delivering the bioactive agent to a specific tissue type or a specific area of the organism.

It would be desirable to provide a lipid vesicle system in which the contents of the vesicle are released when the vesicle is in contact with a specific environment, such as a specific type of tissue within an organism. Preferably, such a system would protect the vesicle contents until contacted with an agent that is present specifically at the targeted environment, at which point the contents would be released. For biological applications, it would be desirable for the vesicle contents to be released when the vesicle is in contact with a biomarker specific for the targeted tissue.

SUMMARY

In one aspect, the invention provides an amphiphilic substance including a hydrophobic group, and a polynucleotide group attached to the hydrophobic group. The polynucleotide group includes a first polynucleotide segment and a second polynucleotide segment. The first and second polynucleotide segments are at least partially complementary and are bound together by interactions including base pairing. At least one of the first and second segments includes at least one of an aptamer and a nucleic acid-based enzyme.

In another aspect, the invention provides a lipid vesicle including an amphiphilic substance as described above, a first polar lipid that is an unstable vesicle former, and a polar liquid.

In yet another aspect, the invention provides a method of forming a lipid vesicle including combining ingredients including an amphiphilic substance as described above, a first polar lipid that is an unstable vesicle former, and a polar liquid. The first polar lipid and the amphiphilic substance form a vesicle wall.

In yet another aspect, the invention provides a controlled delivery system including a lipid vesicle as described above, and a bioactive agent in the lipid vesicle.

In yet another aspect, the invention provides a method of delivering a bioactive agent including administering a controlled delivery system, as described above, to an organism.

The following definitions are included to provide a clear and consistent understanding of the specification and claims.

The term "amphiphilic substance" means a substance that includes both a hydrophilic group and a hydrophobic group.

The term "group" means a linked collection of atoms within a molecular entity.

The term "hydrophobic group" means a group that, if separate from any other group, is insoluble in water but is soluble in nonpolar organic solvents.

The term "polynucleotide group" means a group that, if separate from any other group, would be a polynucleotide radical.

The term "polynucleotide" means a sequence of at least two mononucleotides. Nucleic acids that may be incorporated into a polynucleotide as mononucleotides include natural nucleic acids, unnatural nucleic acids, modified nucleic acids, and peptide nucleic acids (PNAs).

The term "complementary sequences" means two mononucleotide sequences that can form base pairing. The complementary sequences may be present in a single polynucleotide, or they may be present in separate polynucleotides.

The term "base pairing" means the ability of two nucleobases to form one or more hydrogen bonds. For example, in Watson-Crick base pairing, base pairing between adenosine and uridine or thymidine involves two hydrogen bonds, whereas base pairing between guanosine and cytosine involves three hydrogen bonds.

The terms "complementary base pairing" and "complementarity" refer to the ability of a polynucleotide to form a secondary structure containing at least one nucleotide base-pair. For example, complementarity between sequences of two polynucleotides refers to the ability of the two sequences to form intermolecular base pairing (for example, Watson-Crick base pairing), resulting in a hybridized structure between the two polynucleotides. Complementarity may be complete, meaning that no unpaired or mismatched nucleobases exist within the hybrid structure formed. Complementarity may be partial, meaning that mismatches or internal bulges or loops may arise within the hybrid structure.

The term "aptamer" means a polynucleotide that has been selected from a random pool of polynucleotides based on its ability to bind another substance, referred to as a target. Aptamers have been selected that bind ions, polynucleotides, proteins, organic compounds, or entire organisms. The mononucleotides of an aptamer may adopt a particular conformation upon binding to its target.

The term "effector" means a molecule that, when bound to an aptamer induces a specific structure or function in the aptamer. Examples of effectors include metal ions, polynucleotides, proteins, and organic compounds.

An "effector binding site" is at least a portion of an aptamer that can bind the effector for that aptamer. An effector binding site may be specific, binding only one effector in the presence of other possible effectors. For example, an aptamer may have a binding site that specifically binds adenosine, even in the presence of many other molecules such as guanosine, thymidine, cytidine. An effector binding site may be partially specific, binding only a class of substances, or it may be non-specific.

The term "nucleic acid-based enzyme" means an enzyme that principally contains mononucleotides. Examples of nucleic acid-based enzymes include ribozymes (RNAzymes), deoxyribozymes (DNAzymes), and aptazymes. Nucleic acids that may be incorporated into a nucleic acid-based enzyme as mononucleotides include natural nucleic acids, unnatural nucleic acids, modified nucleic acids, and peptide nucleic acids (PNAs). A nucleic acid-based enzyme may require a co-factor for efficient substrate cleavage and/or specific effector binding. Examples of co-factors include metals such as Mg(II) and Pb(II).

The term "aptazyme", also referred to as "allosteric DNA/RNAzyme" or "allosteric (deoxy)ribozyme," is a DNA/RNAzyme in which the enzymatic activity is regulated by an effector. An aptazyme typically contains an aptamer domain, which recognizes an effector, and a catalytic domain. See, for example, Hesselberth, J., et al., *Reviews in Molecular Biotechnology*, vol. 74, pp. 15-25, (2000); Soukup, G. A., et al., *Current Opinion in Structural Biology*, vol. 10, pp. 318-325, (2000); and Tang, J., et al., *Chemistry & Biology*, vol. 4, no. 6, pp. 453-459, (1997).

BRIEF DESCRIPTION OF THE DRAWINGS

The invention can be better understood with reference to the following drawings and description. The components in the figures are not necessarily to scale, emphasis instead being placed upon illustrating the principles of the invention.

DETAILED DESCRIPTION

The present invention makes use of the discovery that the formation, stabilization and/or rupture of lipid vesicles can be controlled by the incorporation of an amphiphilic substance containing an aptamer and/or a nucleic acid-based enzyme in the vesicle wall. In the absence of a rupture agent, the amphiphilic substance can facilitate the formation and stabilization of a vesicle. In the presence of a rupture agent, the vesicle can be destabilized, causing the vesicle to rupture and release its contents. These vesicles may be used in a variety of applications, including controlled delivery of bioactive agents in an organism.

The amphiphilic substance for incorporation in a vesicle wall may include a hydrophobic group and a polynucleotide group, attached to the hydrophobic group, where the polynucleotide group includes an aptamer and/or a nucleic acid-based enzyme. The rupture agent may be, for example, an effector for an aptamer of the polynucleotide group, or a co-factor for a nucleic acid-based enzyme of the polynucleotide group. In one example, the aptamer can bind the rupture agent, causing the aptamer to undergo a conformational change and/or to release a segment of the polynucleotide group that was bound together with the aptamer by interactions including base pairing. In another example, the nucleic acid-based enzyme can be activated in the presence of the rupture agent, causing the enzyme to cleave the polynucleotide group, releasing a portion of the group. The amphiphilic substance also may include a stabilizing group connected to the polynucleotide group. The interaction of the aptamer and/or nucleic acid-based enzyme with the rupture agent may then allow the stabilizing group to dissociate from the amphiphilic substance and the vesicle wall, causing the vesicle to rupture.

Figure 1:
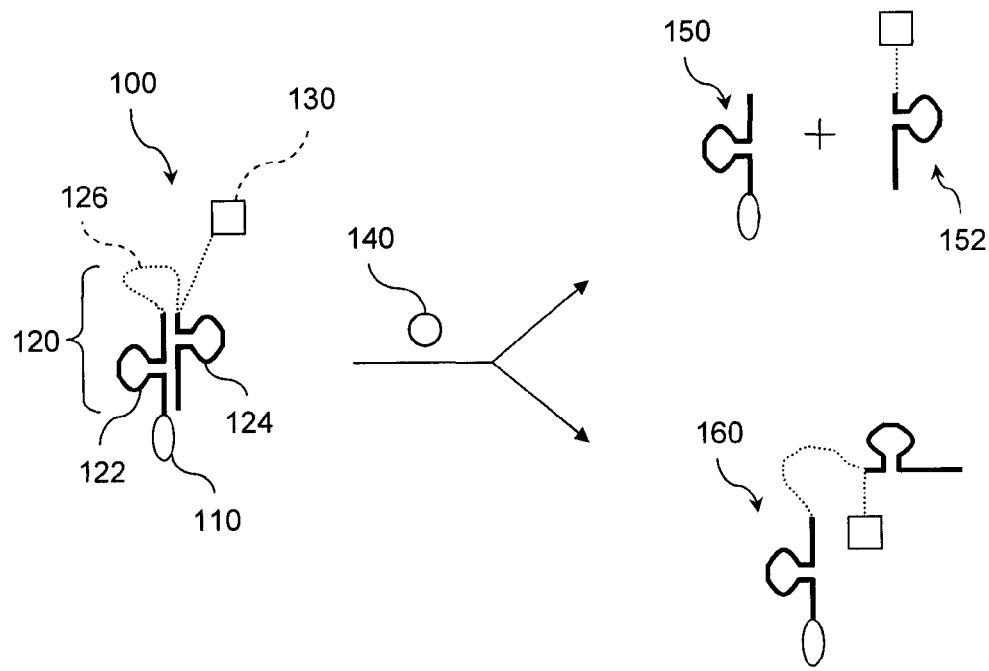
FIG. 1 is a scheme representing the interaction of a rupture agent with an amphiphilic substance that includes an aptamer and/or a nucleic acid-based enzyme.

FIG. 1 is a scheme representing the interaction of a rupture agent with an amphiphilic substance that includes an aptamer and/or a nucleic acid-based enzyme. Amphiphilic substance 100 includes a hydrophobic group 110, a polynucleotide group 120, and optionally a stabilizing group 130. The polynucleotide group 120 includes a first polynucleotide segment 122 and a second polynucleotide segment 124, where the first and second segments are at least partially complementary and are bound together by interactions including base pairing. At least one of the first and second segments includes an aptamer and/or a nucleic acid-based enzyme. The polynucleotide group 120 optionally may include a linking group 126 between the first and second segments.

Exposure of the amphiphilic substance 100 to a rupture agent 140 disrupts the base pairing between the first and second polynucleotide segments, resulting in a dissociation of the first and second polynucleotide segments. The polynucleotide group 120 thus undergoes a change in its size and/or conformation. If the optional linking group 126 is absent, the dissociation may produce a first product 150 that includes the hydrophobic group and at least a portion of the first polynucleotide segment, and a second product 152 that includes at least a portion of the second polynucleotide segment and optionally includes the stabilizing group. If the optional linking group 126 is present, the dissociation may produce a product 160 that has a polynucleotide group conformation different from that of amphiphilic substance 100.

The hydrophobic group 110 may be any group that, if separate from the amphiphilic substance, would be insoluble in water but soluble in nonpolar organic solvents. Preferably, the hydrophobic group can be incorporated into a lipid vesicle wall, for example by association with the non-polar core of the lipid bilayer. Examples of hydrophobic molecules that can be linked to a polynucleotide to form an amphiphilic substance include waxes, fatty acids and salts, triglycerides, phosphoglycerides, sphingolipids, prostaglandins, terpenes, and steroids.

Examples of sphingolipids that may be linked to a polynucleotide to form an amphiphilic substance include sphingosines, such as D-erythro-sphingosine, sphingomyelin, ceramides, cerebrosides, brain sulfatides and glucosylceramide; gangliosides, such as ovine brain gangliosides and porcine brain gangliosides; and phytosphingosines, such as phytosphingosine, D-ribo-phytosphingosine-1-phosphate, and N-acyl phytosphingosines (i.e. C2, C8 or C18). Examples of phosphoglycerides that may be linked to a polynucleotide to form an amphiphilic substance include phosphatidylcholines, phosphocolines (such as platelet-activation factor (PAF), phosphatidylethanolamines, phosphatidylglycerols, phosphatidylinositols, phosphatidylserines (including sodium salts), cardiolipins (including sodium salts), phosphatidic acids, lysophosphatides, and diglycerides. These phosphoglycerides may include one or more saturated or unsaturated hydrocarbon groups, such as lauroyl, myristoyl, palmitoyl, stearoyl, arachidoyl, oleyl, linoleoyl, and erucoyl. Mixtures of these hydrophobic molecules, such as mixtures present in tissue extractions, may also be used. These and other hydrophobic molecules, which may be linked to a polynucleotide to form an amphiphilic substance, may be purchased from a commercial supplier, such as Avanti Polar Lipids (Alabaster, Ala.).

Preferably, the hydrophobic group 110 is a group formed from a steroid, such as a sterol, a bile acid, or a hormone. More preferably the hydrophobic group is formed from a sterol, such as cholesterol, cholestanol, coprostanol, stigmasterol, sitosterol, ergosterol or calciferol. More preferably the hydrophobic group is formed from chlolesterol. See, for example, Cram, D. J. and Hammond, G. S. "Organic Chemistry" McGraw-Hill, 1959, pp. 560-569.

The polynucleotide group 120 includes a first polynucleotide segment 122 and a second polynucleotide segment 124. The first and second polynucleotide segments are at least partially complementary, and can bind together by interactions including base pairing. This base pairing may be disrupted when the polynucleotide group is contacted with a rupture agent 140, resulting in a dissociation of the first and second polynucleotide segments from each other. Other interactions besides base pairing may exist between the first and second polynucleotide segments, such as covalent bonding. Optional linking group 126 may extend between the first and second polynucleotide segments.

The polynucleotide group 120 may include an aptamer. One or both of the first and second polynucleotide segments 122 and 124 independently may include an aptamer. For a polynucleotide having an aptamer in each segment, these aptamers may be the same or different. Preferably only one of the first and second polynucleotide segments includes an aptamer. In one example of a polynucleotide group that includes an aptamer, the rupture agent 140 is an effector for the aptamer. In the absence of the effector, the two polynucleotide segments are bound together by interactions including base pairing of the complementary sequences. In the presence of the effector, the corresponding aptamer preferentially binds the effector, disrupting the base pairing between the two polynucleotide segments. An aptamer in a polynucleotide segment may include at least part of the complementary sequence of the segment. In this example, the aptamer may be selected for its ability to bind the other polynucleotide segment in the absence of an effector, but to preferentially bind the effector when the effector is present. An aptamer in a polynucleotide segment may include none of the complementary sequence of the segment. In this example, the aptamer may be selected for its ability to induce a conformational change in the complementary sequence when the effector is present.

Figure 2:
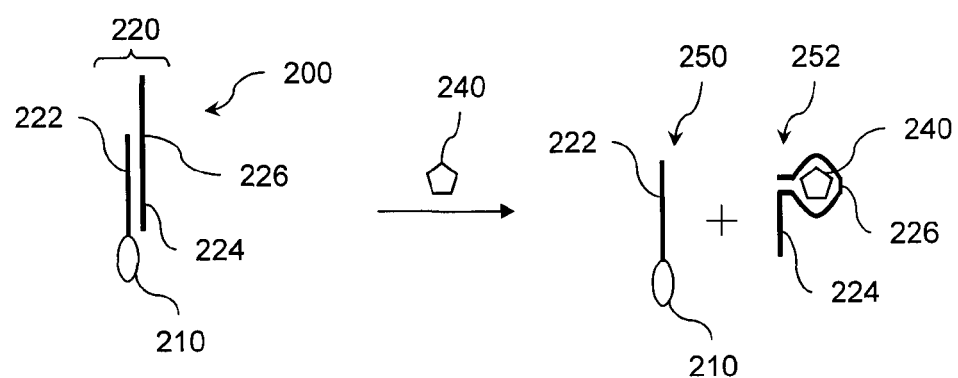
FIG. 2 is a scheme representing an example of an interaction of a rupture agent with an amphiphilic substance that includes an aptamer.

FIG. 2 is a scheme representing an example of an interaction of a rupture agent with an amphiphilic substance that includes an aptamer. Amphiphilic substance 200 includes a hydrophobic group 210 and a polynucleotide group 220. The polynucleotide group 220 includes a first polynucleotide segment 222 and includes a second polynucleotide segment 224, including an aptamer 226. The first and second segments are at least partially complementary, and are bound together by interactions including base pairing. Exposure of the amphiphilic substance 200 to an effector 240 for the aptamer 226 results in a dissociation of the first and second polynucleotide segments. This dissociation yields a first product 250 and a second product 252. The first product 250 includes the hydrophobic group 210 and the first polynucleotide segment 222. The second product 252 includes the second polynucleotide segment 224, including aptamer 226 bound to effector 240. If the polynucleotide group included an optional linking group (not shown), the dissociation of the first and second polynucleotide segments may yield a polynucleotide group having a conformation different from that present in amphiphilic substance 200.

An aptamer that binds a particular effector may be isolated by in vitro selection from a library of polynucleotides having random sequences. The selection process may be performed using standard procedures, such as the technique of systematic evolution of ligands by exponential enrichment (SELEX) (Tuerk and Gold 1990) or other approaches (Cadwell and Joyce 1992, Chapman and Szostak 1994, Joyce 1994, Cadwell and Joyce 1994, Tsang and Joyce 1996). A list of aptamers and their corresponding effectors is disclosed in U.S. Provisional Patent Application No. 60/821,043, to Yi Lu et al., filed Aug. 1, 2006, which is incorporated herein by reference.

A library for selection of an aptamer that binds a particular effector may include polynucleotides that have two regions. One of the regions has random sequences, and the other region has conserved sequences suitable for hybridizing to a second polynucleotide. The library may be pre-selected for hybrid formation with the second polynucleotide by incubating representatives from the library with the second polynucleotide under conditions favorable for duplex formation and in the absence of the effector. Polynucleotides that represent "non-binders" are removed from the pool at the outset, as these already adopt structures that preclude hybridization to the second polynucleotide, independent of the effector. The initial collection of bound polynucleotides represents the candidate polynucleotides of the library that may adopt a hybridized complex with the second polynucleotide.

These candidate polynucleotides may then be isolated, amplified under suitable conditions, and incubated in the presence of the effector molecule and the second polynucleotide. In this phase of selection, the "non-binders" are isolated, as these represent candidate sequences that have bound the effector rather than hybridizing with the second polynucleotide. The polynucleotides in the unbound fraction may be re-amplified, and the selection process may be repeated. The next selection may be carried out under more stringent conditions that are favorable to hybrid selection, or it may be carried out under conditions of lower effector concentrations. Another type of selection process involves gradient elution profiles, in which varying concentrations of the effector are present. This selection may isolate discrete populations of polynucleotides having different response profiles for the same effector, such as different concentration dependencies. One or more rounds of selection may be performed in the absence of the effector to ensure the enriched aptamer species retain the ability to hybridize to the second polynucleotide.

Hybrid selection may be performed using second polynucleotides immobilized on solid supports, or any other method that enables separation of bound and unbound candidate polynucleotides from second polynucleotides, such as gradient centrifugation, chromatography, or mobility-shift assay. Where gradient elution procedures are employed, the use of automated chromatography procedures, such as RPLC or HPLC, is preferred.

An aptamer may be constructed using rational design principles. An aptamer for a particular effector may be chosen from one of the several hundred examples known in the art. See, for example, Jennifer F. Lee, Jay R. Hesselberth, Lauren Ancel Meyers, and Andrew D. Ellington, "Aptamer Database," *Nucleic Acids Res.* 2004 Jan. 1; 32(Database issue): D95-D100. The folding of many aptamers is well characterized, and the nucleotide sequence of the second polynucleotide may be designed based on the aptamer sequence. For example, a region within an aptamer may be designed to adopt a particular single-stranded conformation upon binding the effector. The second polynucleotide may then be designed to have a sequence complementary to this region. Binding between the first and second polynucleotides may be favored in the absence of the effector, but may be disfavored in the presence of the effector.

Rational design principles can be confirmed in the laboratory through simple and rapid experimental tests. For example, candidate polynucleotides and second polynucleotides may be prepared that contain one or more probes, such as a radioisotope, a fluorophore, or a particle. The stabilities of the polynucleotide complexes in the presence or absence of the effector can be studied, for example by mobility-shift assay, gradient centrifugation, or hybrid selection. Polynucleotide complexes may also be studied spectrophotometrically, where the polynucleotides are labeled with substances having a spectral signature, such as gold particles. In this technique, complex formation is monitored by the formation of particle aggregates, which display a distinct color change relative to dispersed particles. Examples of this technique are described in U.S. Patent Application Publication No. US 2006/0166222 A1 to Lu et al., published Jul. 27, 2006, which is hereby incorporated by reference.

An aptamer may be provided in vitro from a random sequence library by first selecting with the desired effector. Candidate polynucleotides displaying high affinity for the effector are characterized with regard to their folded secondary structure. Species having high affinity for the effector may share nucleotide sequences, known as consensus sequences, which may conserved for functional reasons. These species also may adopt common secondary structures, giving rise to additional consensus structural elements. The predicted conformations may be generated using a folding program, such as RNAstructure, as implemented in the Vienna RNA Package. The predicted foldings may be confirmed experimentally by doping one or more selected sequences with random nucleotides in the regions containing putative primary and secondary structure consensus motifs, and then reselecting for efficient effector binding. Where a particular structural feature of the aptamer is required for efficient effector binding, aptamers containing the preserved features may be recovered during the reselection process. Once the desired aptamer species have been isolated and characterized, second polynucleotides that bind to the aptamer(s) may be designed based on structural considerations, such as classical Watson-Crick base pairing rules.

The polynucleotide group 120 may include a nucleic acid-based enzyme. One or both of the first and second polynucleotide segments 122 and 124 independently may include a nucleic acid-based enzyme. For a polynucleotide having a nucleic acid-based enzyme in each segment, these enzymes may be the same or different. Preferably only one of the first and second polynucleotide segments includes a nucleic acid-based enzyme, and the other of the first and second polynucleotide segments includes a substrate for the enzyme. In one example of a polynucleotide group that includes a nucleic acid-based enzyme, the rupture agent 140 is a co-factor for the enzyme. In the absence of the co-factor, the two polynucleotide segments are bound together by interactions including base pairing of the complementary sequences. In the presence of the co-factor, the nucleic acid-based enzyme of the one polynucleotide segment cleaves the substrate included in the other polynucleotide segment, disrupting the base pairing between the two polynucleotide segments. Preferably the two polynucleotide segments are bound together in an orientation that provides for the substrate of the nucleic acid-based enzyme to be close to the active site of the enzyme. A nucleic acid-based enzyme of a polynucleotide segment may include at least part of the complementary sequence of the segment, or the enzyme may be distinct from the complementary sequence.

Figure 3:
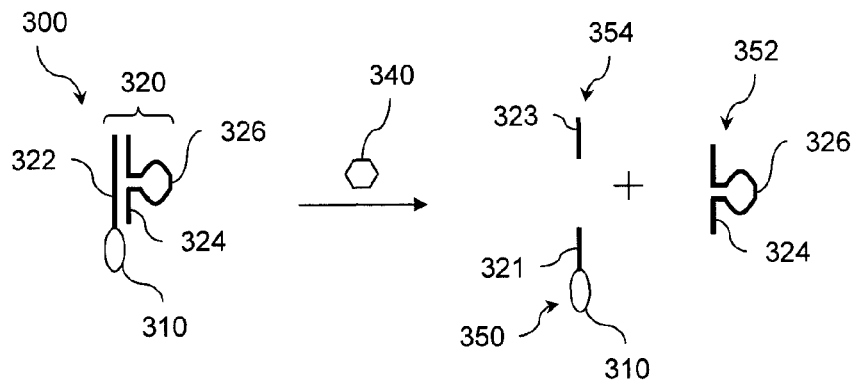
FIG. 3 is a scheme representing the interaction of a rupture agent with an amphiphilic substance that includes a nucleic acid-based enzyme.

FIG. 3 is a scheme representing the interaction of a rupture agent with an amphiphilic substance that includes a nucleic acid-based enzyme. Amphiphilic substance 300 includes a hydrophobic group 310 and a polynucleotide group 320. Polynucleotide group 320 includes a second polynucleotide segment 324 including a nucleic acid-based enzyme 326, and includes a first polynucleotide segment 322 including a substrate for the nucleic acid-based enzyme. The first and second segments are at least partially complementary, and are bound together by interactions including base pairing. Exposure of the amphiphilic substance 300 to a co-factor 340 for the nucleic acid-based enzyme 326 results in cleavage of the substrate of the enzyme and a dissociation of the first and second polynucleotide segments. This dissociation yields a first product 350, a second product 352 and a third product 354. The first product 350 includes the hydrophobic group 310 and a first portion 321 of the first polynucleotide segment. The second product 352 includes the second polynucleotide segment 324. The third product 354 includes a second portion 323 of the first polynucleotide segment.

In another example of a polynucleotide group 120 that includes a nucleic acid-based enzyme, the enzyme is present with an aptamer, and the two species together form an aptazyme. In this example, the rupture agent 140 may be an effector for the aptamer, where the interaction between the aptamer and the effector activates the enzyme. In the absence of the effector for the aptamer portion of the aptazyme, the two polynucleotide segments are bound together by interactions including base pairing of the complementary sequences. In the presence of the effector, the enzyme portion of the aptazyme included in the one polynucleotide segment cleaves the substrate included in the other polynucleotide segment, disrupting the base pairing between the two polynucleotide segments. Preferably the two polynucleotide segments are bound together in an orientation that provides for the substrate of the enzyme to be close to the active site of the enzyme. An aptazyme of a polynucleotide segment may include at least part of the complementary sequence of the segment, or the aptazyme may be distinct from the complementary sequence.

Figure 4:
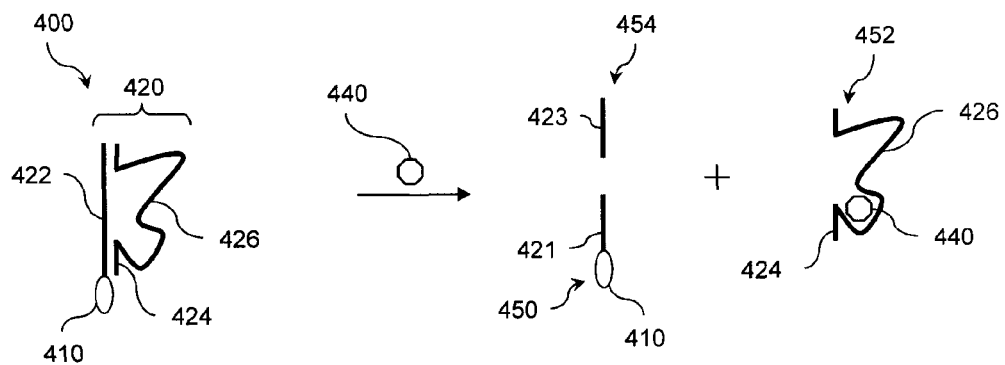
FIG. 4 is a scheme representing the interaction of a rupture agent with an amphiphilic substance that includes an aptazyme.

FIG. 4 is a scheme representing the interaction of a rupture agent with an amphiphilic substance that includes an aptazyme. Amphiphilic substance 400 includes a hydrophobic group 410 and a polynucleotide group 420. Polynucleotide group 420 includes a second polynucleotide segment 424 including an aptazyme 426, and includes a first polynucleotide segment 422 including a substrate for the aptazyme. The first and second segments are at least partially complementary, and are bound together by interactions including base pairing. Exposure of the amphiphilic substance 400 to an effector 440 for the aptazyme 426 results in cleavage of the substrate of the enzyme and a dissociation of the first and second polynucleotide segments. This dissociation yields a first product 450, a second product 452 and a third product 454. The first product 450 includes the hydrophobic group 410 and a first portion 421 of the first polynucleotide segment. The second product 452 includes the second polynucleotide segment 424. The third product 454 includes a second portion 423 of the first polynucleotide segment.

Aptazymes may be obtained using in vitro selection techniques or by rational design. See, for example Tang et al. 1997; Hesselberth et al. 2000; Soukup, G. A., et al., *Proc. Natl. Acad. Sci. USA*, vol. 96, pp. 3584-3589, (1999); Robertson, M. P., et al., *Nucleic Acids Research*, vol. 28, no. 8, pp. 1751-1759, (2000); Seetharaman, S., et al., *Nature Biotechnology*, vol. 19, pp. 336-341, (2001); Wang, D. Y., et al., *J. Mol. Biol.*, vol. 318, pp. 33-43, (2002). Aptazymes made using in vitro selection techniques include a nucleic acid-based enzyme specific for a particular substrate whose activity depends upon an effector. Numerous examples of nucleic acid-based enzymes have been identified, either by engineering naturally occurring ribozymes or by in vitro selection of ribozymes and deoxyribozymes.

A library population of candidate polynucleotides containing nucleic acid-based enzymes may be prepared in which the activity is compromised due to the insertion of a randomized sequence cassette. Catalytically active members of the library are then selected based upon having restored catalytic activity in the presence of a selected effector. Where appropriate, the requisite co-factors and ions are included in the selection protocols at the outset, so that the aptazymes become responsive to the selected effector in the form of the aptamer target, rather than to co-factors. Negative selections may be performed to improve specificity of aptazymes with regard to different effectors.

Aptazymes may also be obtained by a rational design approach. Candidate polynucleotides may be selected from a group of nucleic acid-based enzymes belonging to different classifications (for example, hairpin ribozyme, hammerhead ribozyme, group I intron, among others). Preferred nucleic acid-based enzymes include those in which an insertion of additional nucleotides or sequences disrupts catalytic activity. An aptamer for a particular effector may be selected from one of many aptamer sequences known in the art or made using in vitro selection techniques. The chosen aptamer may be introduced in the vicinity of the catalytic core for a nucleic acid-based enzyme, whereby the activity of the catalytic core becomes responsive upon binding the target effector. Examples of rationally designed aptazymes have been generated using this general approach.

Optional linking group 126 may include any group that can form a stable connection between the first and second polynucleotide segments. For example, an optional linking group may include a third polynucleotide segment that is not complementary to either of the first or second polynucleotide segments. In another example, the polynucleotide group may be a single stranded polynucleotide. In another example, an optional linking group may include a polypeptide containing two or more amino acid residues.

Optional stabilizing group 130 may include a polymer. Examples of polymeric stabilizing groups include hydrophilic polymers, including polyethers, such as poly(ethylene oxide), polyethylene glycol (PEG), and ethers, esters and amides of PEG; ionic polymers, such as poly(acrylic acids), poly(methacrylic acids), sulfonated polystyrene, and sulfonated polystyrene; polyacrylamides; poly(vinyl alcohol); poly(vinyl imidazoles), and poly(ethylene imine). Examples of polymeric stabilizing groups include biodegradable polymers, including poly(hydroxyalkanoates), such as poly(hydroxybutyrate) and poly(hydroxyvalerate); polyesters, such as poly(lactic acid), poly(glycolic acid) and poly(caprolactone); and poly(amidoamine) dendrons and dendrimers (PAMAM). Examples of polymeric stabilizing groups include polysaccharides, such as cellulose, cellulose esters, dextrans, starches, and glycogens. Examples of polymeric stabilizing groups include polypeptides, such as avidin, streptavidin and neutravidin. Examples of polymeric stabilizing groups include polynucleotides, such as DNA, RNA, nucleic acid-based enzymes, aptamers, and peptide nucleic acids. A polymeric stabilizing group may include two or more different polymeric groups, and may include a copolymer having units of two or more different polymers. Preferably the polymeric stabilizing group is PEG, avidin or streptavidin. Although the stabilizing group may by hydrophobic or may include a polynucleotide, the stabilizing group 130 is different from the hydrophobic group 110 and the polynucleotide group 120.

An amphiphilic substance 100 may be prepared by combining a hydrophobic group and a polynucleotide group. In one example, a first polynucleotide segment of a polynucleotide group is linked to a hydrophobic group, and this combined product is contacted with the second polynucleotide segment. The second polynucleotide segment may be linked to an optional stabilizing group, and this may occur before or after the second segment is combined with the first segment. In another example, a first and a second polynucleotide segment are combined to form a polynucleotide group, and this polynucleotide group is then linked at one end with a hydrophobic group. The second polynucleotide segment may be linked to an optional stabilizing group, and this may occur before or after the second segment is combined with the first segment.

Figure 5:
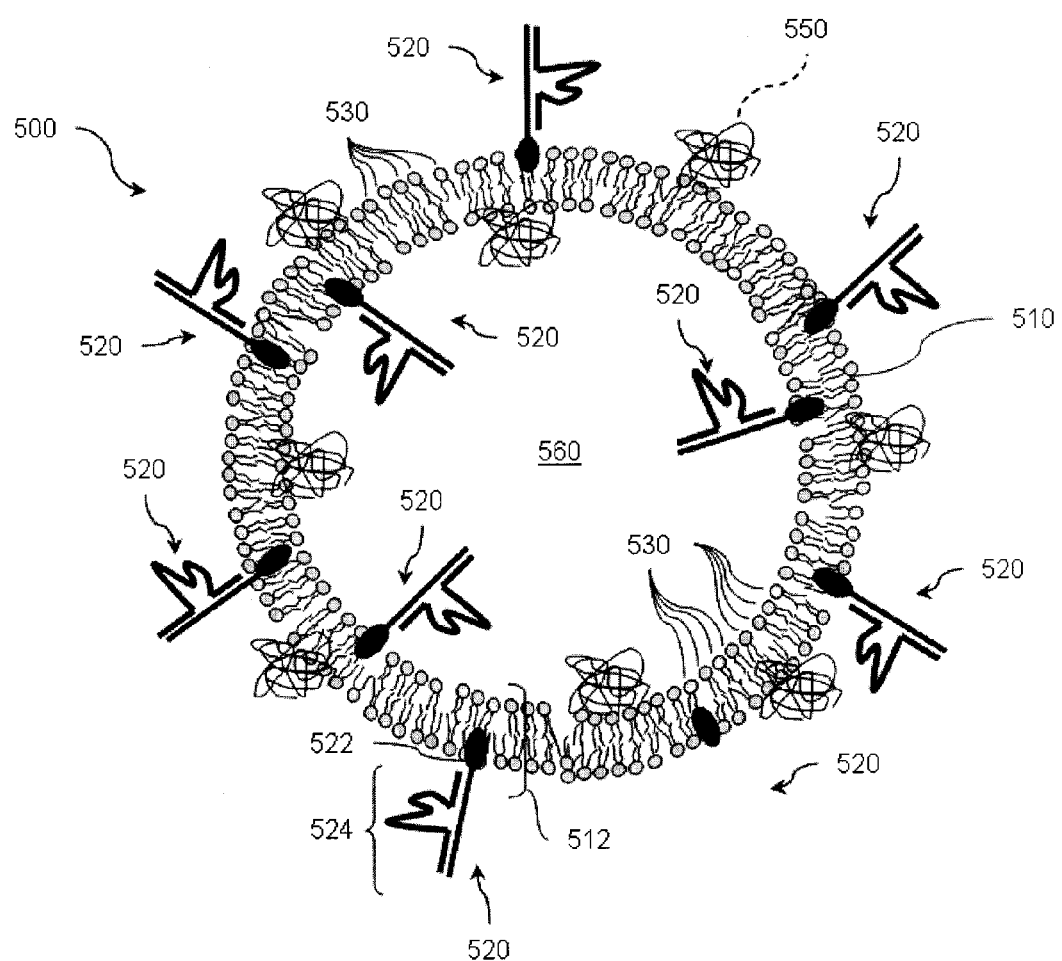
FIG. 5 is a scheme representation of a lipid vesicle that includes a vesicle wall, an amphiphilic substance and optionally a stabilizing group.

FIG. 5 is a representation of a lipid vesicle 500 that includes a vesicle wall 510, an amphiphilic substance 520 and optionally a stabilizing group 550. The vesicle wall 510 includes a lipid bilayer 512, including polar lipid 530. The amphiphilic substance 520 includes a hydrophobic group 522 and a polynucleotide group 524, and the hydrophobic group 522 is at least partially in the lipid bilayer 512. The polynucleotide group 524 includes an aptamer and/or a nucleic acid-based enzyme. The vesicle wall encloses an internal space 560.

The polar lipid 530 includes a polar lipid that is an "unstable vesicle former." Unstable vesicle formers are polar lipids that will not form vesicles, at least 50% of which persist for at least one hour, when prepared by the following method. The polar lipid is dissolved in chloroform and placed in a glass test tube. The chloroform is then removed by evaporation under a steady stream of nitrogen, followed by vacuum for twelve hours. The dried lipid material is re-hydrated in 10 millimolar (mM) $Na_2HPO_4$ to give a 25 mg/mL concentration. The resultant aqueous mixture is maintained for 60 minutes at a temperature above the phase transition temperature of the lipid. The lipid vesicles are then reduced in size by any convenient means, such as by high pressure homogenization or by sonication with a micro-tip 450 watt sonicator used at a 40% duty cycle.

The polar lipid 530 may include a polar phospholipid that is an unstable vesicle former. Examples of polar phospholipids that may be used as an unstable vesicle former include Lyso-Phosphatidylcholine (Lyso-PC), 1,2-dioleoyl-sn-glycero-3-ethylphosphocholine (DOPC-e), 1-palmitoyl-2-oleyl-3-glycerophosphorcholine (POPA), 1,2-dioleoyl-3-trimethylammoniumpropane (DOTAP), 1-steroyl-2-docosaheaxenoyl-3-phosphocholine (18:0, 22:6, PC), mixed chain phosphatidyl choline (MPC), phosphatidyl ethanol (PE), 1,2-dioleoyl-sn-glycero-3-phosphoethanolamine (DOPE), 1-palmitoyl-2-hydroxy-sn-glycero-3-phosphocholine (16:0-Lyso PC), and combinations thereof. Preferably the unstable vesicle former includes DOPE.

The polar lipid 530 also may include a polar lipid that is a "stable vesicle former." Stable vesicle formers are polar lipids that will form vesicles, at least 50% of which will persist for at least one hour, when prepared as described for unstable vesicle formers. The polar lipid may include a polar phospholipid that is a stable vesicle former. Examples of polar phospholipids that may be used as a stable vesicle former include Soy Phosphatidylcholine (SOYPC) (Structure (XIV), dioleoylphosphatidylcholine (DOPC) (Structure (XV)), 1-palmitoyl-2-docosahexaenoyl-sn-glycero-3-phosphocholine (16:0, 22:6 PC) (Structure (XVI)), 1-palmitoyl-2-oleoyl-phosphocholine (16:0, 18:1 PC), 1-palmitoyl-2-linolinoyl-3-phosphocholine (16:0, 18:3 PC), 1-palmitoyl-2-arachidonoyl-3-phosphocholine (16:0, 20:4, PC), and combinations thereof.

The internal space 560 may contain a polar liquid, such as water, an aqueous mixture and/or a polar organic liquid. The internal space may further contain one or more other substances. In one example, the internal space includes a bioactive agent, such as an organic molecule, an inorganic molecule, a pharmaceutical, a polypeptide, a polynucleotide, or an antibody that interacts with an intracellular antigen. The internal space 560 may contain a bioactive agent without a polar liquid.

A method of forming a lipid vesicle includes combining ingredients including a polar lipid, a polar liquid, and an amphiphilic substance that includes a hydrophobic group and a polynucleotide group. The polynucleotide group includes an aptamer and/or a nucleic acid-based enzyme. The polar lipid includes a polar lipid that is an unstable vesicle former. The ingredients may further include a second polar lipid that is a stable vesicle former. The ingredients may further include a bioactive agent.

The polar lipid and the amphiphilic substance may be as described above. More than one type of polar lipid and/or more than one type of amphiphilic substance may be present. The polar liquid may include a polar liquid, such as water, an aqueous mixture and/or a polar organic liquid. The polar liquid may further include one or more other substances, such as a bioactive agent.

The ingredients for forming the lipid vesicle optionally may further include a stabilizing substance. Examples of stabilizing substances include hydrophilic polymers, ionic polymers, biodegradable polymers, polysaccharides, polypeptides, and polynucleotides. A stabilizing substance may include two or more different polymers, and may include a copolymer having units of two or more different polymers. Preferred stabilizing substances include PEG, avidin and streptavidin. In one example, the stabilizing substance may be present as a stabilizing group connected to a second hydrophobic group. In this example, the vesicle wall may further include at least a portion of the second hydrophobic group. The second hydrophobic group may be as described for the hydrophobic group of the amphiphilic substance. Although the stabilizing substance may by hydrophobic or may include a polynucleotide, the stabilizing substance is different from the hydrophobic group and the polynucleotide group of the amphiphilic substance.

Figure 6:
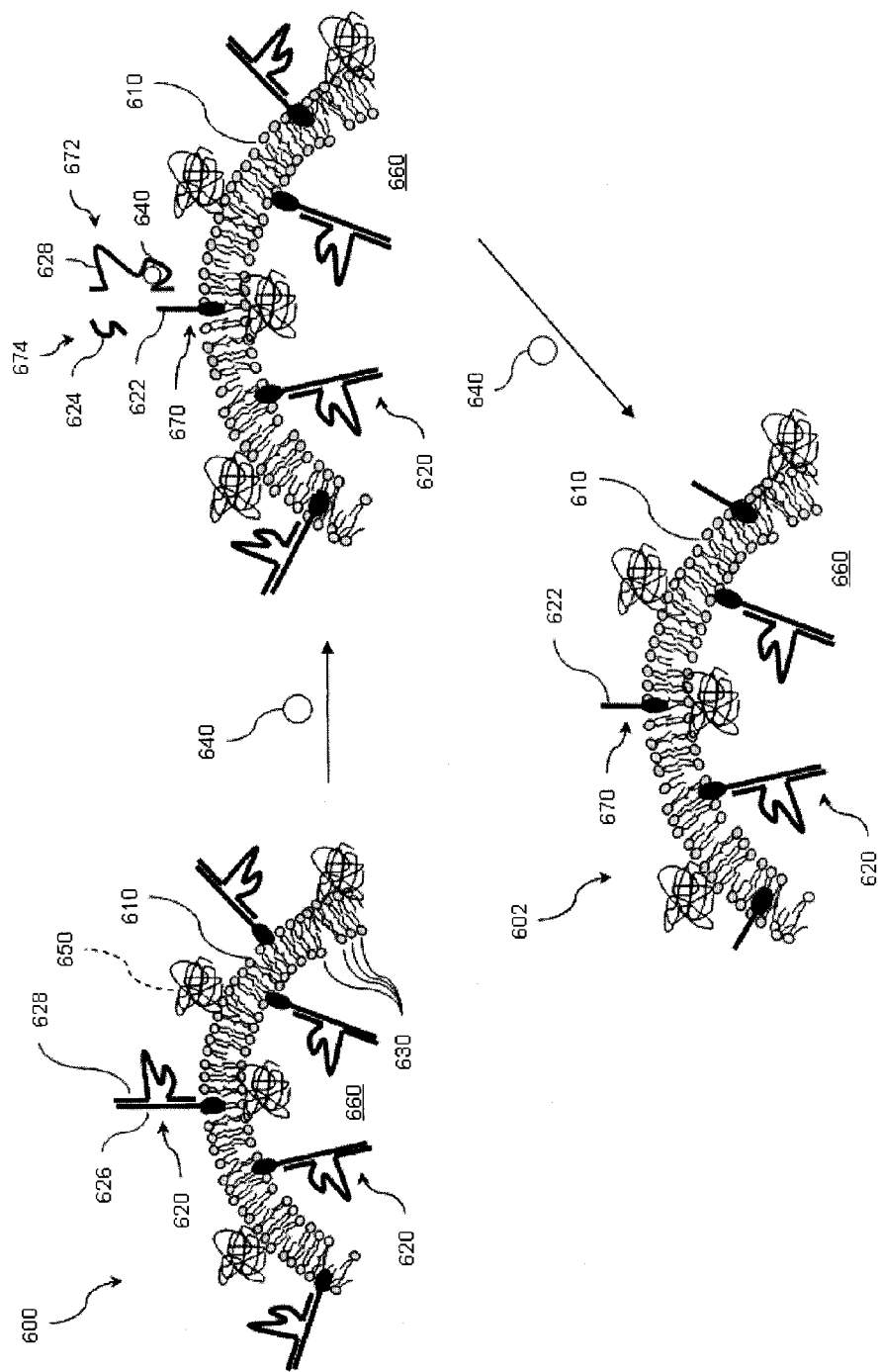
FIG. 6 is a scheme representing the interaction of a rupture agent with a vesicle that contains an amphiphilic substance including an aptamer and/or a nucleic acid-based enzyme.

FIG. 6 is a scheme representing the interaction of a rupture agent with a vesicle that contains an amphiphilic substance including an aptamer and/or a nucleic acid-based enzyme. Vesicle 600 includes a vesicle wall 610 enclosing an internal space 660, and an amphiphilic substance 620. The vesicle wall includes a polar lipid 630 and an optional stabilizing substance 650. The amphiphilic substance 620 includes a polynucleotide group having a first polynucleotide segment 626 and a second polynucleotide segment 628. The vesicle is stable until the amphiphilic substance 620 is exposed to sufficient amounts of a rupture agent 640. Exposure of the amphiphilic substance 620 to sufficient amounts of the rupture agent 640 results in a disruption of the base pairing between the first and second polynucleotide segments. This disruption leads to the dissociation of the first and second polynucleotide segments at the exterior of the vesicle wall, yielding at least one product 670, which includes a modified polynucleotide group 672 that differs from the polynucleotide group of the amphiphilic substance 620 in its size and/or conformation. De-stabilized vesicle 602 may include product 670 at the exterior of the vesicle wall, and amphiphilic substance 620 at the interior of the vesicle wall. De-stabilized vesicle 602 cannot maintain its shape, and the vesicle ruptures.

In the example of FIG. 6, the polynucleotide group 620 includes an aptazyme in the second polynucleotide group 628, and includes a substrate for the aptazyme in the first polynucleotide group 626. The dissociation of the first and second polynucleotide groups yields a first product 670, a second product 672 and a third product 674. The first product 670 includes the hydrophobic group and a first portion 622 of the first polynucleotide segment. The second product 672 includes the second polynucleotide segment 628. The third product 674 includes a second portion 624 of the first polynucleotide segment. The contribution of first product 670 to the stability of the vesicle is less than the contribution of the amphiphilic substance 620, and the original shape of vesicle 600 cannot be maintained by de-stabilized vesicle 602. The polynucleotide group 620 may include an aptazyme, as represented in FIG. 6, or it may include either an aptamer or a nucleic acid-based enzyme. Thus, the at least one product of the dissociation of the first and second polynucleotide segments may be as illustrated in FIGS. 1-4.

One possible explanation for the effect of the change in the amphiphilic substance on the stability of the lipid vesicle is that the steric bulk of the amphiphilic substance influences the geometry of the vesicle wall. Molecular shapes of polar lipids can strongly affect their phase behavior. For example, many amphiphilic molecules with high positive or negative curvatures are unstable vesicle formers, since non-zero curvatures do not allow for the self-assembly necessary for vesicle formation. Polar lipids having a high molecular curvature can be manipulated into forming lipid vesicles by imposing a steric force on the bilayer containing the lipids. This steric force can result from the incorporation in the bilayer of an amphiphilic substance that includes a polynucleotide group. Such lipid vesicles may be stabilized by the difference in the amount of steric bulk at the inner and outer surfaces of the lipid bilayer. When the steric bulk of the polynucleotide group at the outer surface is reduced, for example due to a change in the size and/or conformation of the polynucleotide group, the balance of forces between the inner and outer surfaces is disrupted, leading to loss of integrity of the vesicle wall.

The destabilization effect may be enhanced when the amphiphilic substance includes a stabilizing group. For example, a stabilizing group may be attached to the polynucleotide group in such a way that the dissociation of the first and second polynucleotide segments allows the stabilizing group to separate from the vesicle. The presence of the stabilizing group can affect the asymmetry between the inner and outer layers of the lipid bilayer, and consequently can function as a control parameter for the release of the contents from the vesicle. For example, the addition of a large molecular weight PEG can increase the sensitivity of functionalized vesicles, allowing them to rupture at lower analyte concentrations.

A vesicle that includes an amphiphilic substance, where the amphiphilic substance includes an aptamer and/or a nucleic acid-based enzyme, may be tailored to rupture at different rates. In one example, the diameter of the vesicle can be controlled to affect the rate of rupture when the vesicle is exposed to a rupture agent. For example, a smaller vesicle diameter may allow the vesicle to rupture more rapidly. The average diameter of the vesicles may be, for example, from 20 nanometers (nm) to 10 micrometers (μm). Preferably the average diameter of the vesicles is from 150 nm to 7 μm, more preferably from 200 nm to 5 μm.

Lipid vesicles that include an amphiphilic substance including an aptamer and/or a nucleic acid-based enzyme may be used as part of a controlled delivery system. For example, a controlled delivery system may include the lipid vesicle and a bioactive agent in the vesicle. The contents of the vesicle may be isolated from the surrounding environment until a rupture agent is encountered. The aptamer and/or nucleic acid-based enzyme may interact with the rupture agent, causing the vesicle to rupture and release its contents.

The controlled delivery system can be applied to any environment in which it is desired to release an agent when a particular substance is present. Aptamers and nucleic acid-based enzymes can be produced to have molecular recognition capabilities for a wide range of substances. Thus, if a particular substance is correlated with an environment in which it is desirable to release an agent, an aptamer and/or nucleic acid-based enzyme may be produced that will bind to or be activated by the substance. A lipid vesicle may then be formed from a polar lipid, a polar liquid, the agent to delivered, and an amphiphilic substance that includes the aptamer and/or nucleic acid-based enzyme. Moreover, the lipid vesicle may be programmed to rupture based on a threshold concentration of the substance. This selectivity may be provided, for example, by the properties of the aptamer and/or nucleic acid-based enzyme, by the presence or absence of a stabilizing group attached to the polynucleotide group, and/or by the composition of the lipid vesicle wall.

A controlled delivery system that includes a bioactive agent in a lipid vesicle, where the lipid vesicle includes an amphiphilic substance including an aptamer and/or a nucleic acid-based enzyme, may be used to deliver a bioactive agent. For example, a method of delivering a bioactive agent includes administering the controlled delivery system to an organism.

The controlled delivery system may be used to deliver drug agents to a particular type of tissue in an organism. In one example, an amphiphilic substance may be prepared that includes an aptamer for prostate-specific-membrane-antigen (PSMA). The amphiphilic substance may include a hydrophobic group and a polynucleotide group having two segments, where one segment includes the aptamer, and the other segment includes a sequence complementary to a sequence in that segment. A chemotherapeutic agent for prostate cancer can be encapsulated in a lipid vesicle that includes the amphiphilic substance. When the lipid vesicle comes into contact with prostate cancer tissue, the aptamer can bind the PSMA, causing a change in the polynucleotide group, inducing instability in the bilayer surface, and rupturing the vesicle. Thus, the chemotherapeutic agent is delivered specifically to the cancerous tissue.

The following examples are provided to illustrate one or more preferred embodiments of the invention. Numerous variations may be made to the following examples that lie within the scope of the invention.

EXAMPLES

Materials

All oligonucleotides were obtained from Integrated DNA Technologies Inc. (IDT) and Eurogentec Oligos. The following oligonucleotides were obtained from IDT:

```
(7)-17E-(-1):
                                      (SEQ ID NO: 1)
5' AA AGA GAG ATC TCT TCT (CCGAGCCGGTCGAA) ATA GTG
AG 3'

Biotin-(7)-17E-(-1) (biotin-TEG modification):
                                      (SEQ ID NO: 2)
Biotin -5' AA AGA GAG ATC TCT TCT (CCGAGCCGGTCGAA)
ATA GTG AG 3'

SH-(7)-17E-(-1)) (thiol modification):
                                      (SEQ ID NO: 3)
Thiol-C6-5' AA AGA GAG ATC TCT TCT (CCGAGCCGGTCGA
A) ATA GTG AG 3'
```

An oligonucleotide with cholesterol and RNA base modification, which was a 17E substrate, was obtained from Eurogentec Oligos:

(5)-17DS-(1)-ChoI (SEQ ID NO: 4)
3' TCT CTG TAG AGA AGG (Ra) TAT CAC TC AA 5'-ChoI

Streptavidin was obtained from SouthernBiotech and used without any purification or dilution. Dioleoylphosphatidyl ethanolamine (DOPE) in powder form was obtained from Avanti Polar Lipids. Biotin was obtained from Sigma-Aldrich, dissolved in 50 mM pH 7.3 Hepes buffer, and diluted to 2.2 mM. A FluoroMax® fluorometer was used for measuring the changes in fluorescence intensity in bulk solution of liposomes.

Example 1

Synthesis of Amphiphilic Substance Including Polynucleotide Group Containing DNAzyme The oligonucleotides (5)-17DS-(1)-Chol and (7)-17E-(−1) were combined to form an amphiphilic substance. The first polynucleotide segment of the amphiphilic substance included a cholesterol group as a hydrophobic group, and included a substrate for a nucleic acid-based enzyme based on DNA (DNAzyme). The second polynucleotide segment of the amphiphilic substance included the DNAzyme, and included a sequence complementary to a sequence in the first segment.

The amphiphilic substance was prepared using the following protocol. The oligonucleotides (7)-17E-(−1) (4 microliters (μL) of a 1 mM solution) and (5)-17DS-(1)-Chol (4 μL of a 1 mM solution) were added to 24 μL, of deionized water in a 500 μL PCR tube. To this mixture was added 8 μL of 1 M NaCl and 4 μL of 500 mM pH 7.3 Hepes buffer. The resulting mixture was brought to 80° C. by placing the tube in a beaker with hot water. The mixture then slowly cooled down to room temperature and was stored at 4° C. for half an hour in order to fully hybridize the DNA strands. The sequence of the resulting amphiphilic substance was:

(SEQ ID NO: 5)
5'-Cholesterol-TEG-AACTCACTAT R(a) GGAAGAGATGTCTC
T-3'

(SEQ ID NO: 1)
5'-AAAGAGAGATCTCT TCTCCGAGCCGGTCGAAATAGTGAG-3'

Example 2

Formation of Stable Vesicle Including Amphiphilic Substance Containing Polynucleotide Group The amphiphilic substance of Example 1 was combined with DOPE and a 2% PEG-lipid to form stable vesicles. The PEG had a molecular weight of 2,000 daltons. The stable vesicles had an average diameter of 1 micrometer.

Vesicles were prepared using the following protocol. The DOPE polar lipid (8 micromoles (μmol)) was dissolved in chloroform, dried in a glass vial under nitrogen, and desiccated under vacuum overnight. The amphiphilic substance of Example 1 and a 2% PEG-lipid (Avanti Polar Lipids) was added into the vial, and the mixture was incubated overnight at 35° C. The mixture was then hydrated by adding 1 ml of 50 mM fluorescein in 100 mM NaCl and 50 mM pH 7.3 Hepes buffer. The hydrated mixture was incubated at 35° C. for one day. The resultant solution was extruded 11 times in a mini-extruder through a 1 μm polycarbonate membrane. The resulting vesicles were isolated from the dye mixture using a PD-10 desalting column (Amersham Biosciences). The column was primarily washed with 50 mM pH 7.3 Hepes buffer and 100 mM NaCl. The vesicle solution (200 μL) was run through the column, and two clear reddish lanes were observed. The first fraction containing vesicles was collected in a 1.5 ml tube, and the remainder was washed out with buffer.

Example 3

Controlled Rupture of Vesicles

The stabilized vesicles of Example 2 were reconstituted in water containing 100 mM NaCl and 50 mM pH 7.4 Hepes buffer. The release of fluorescein was measured by fluorescence spectroscopy. The 50 mM fluorescein mixture in the vesicles was self-quenching. As the fluorescein is released into the environment, the total concentration of fluorescein in the solution after vesicle disruption is much less than the concentration of fluorescein within the vesicles before disruption, causing a cessation of the self-quenching effect of the high concentration of fluorescein in the vesicles. This was observed as an increase in fluorescence intensity.

Figure 7:
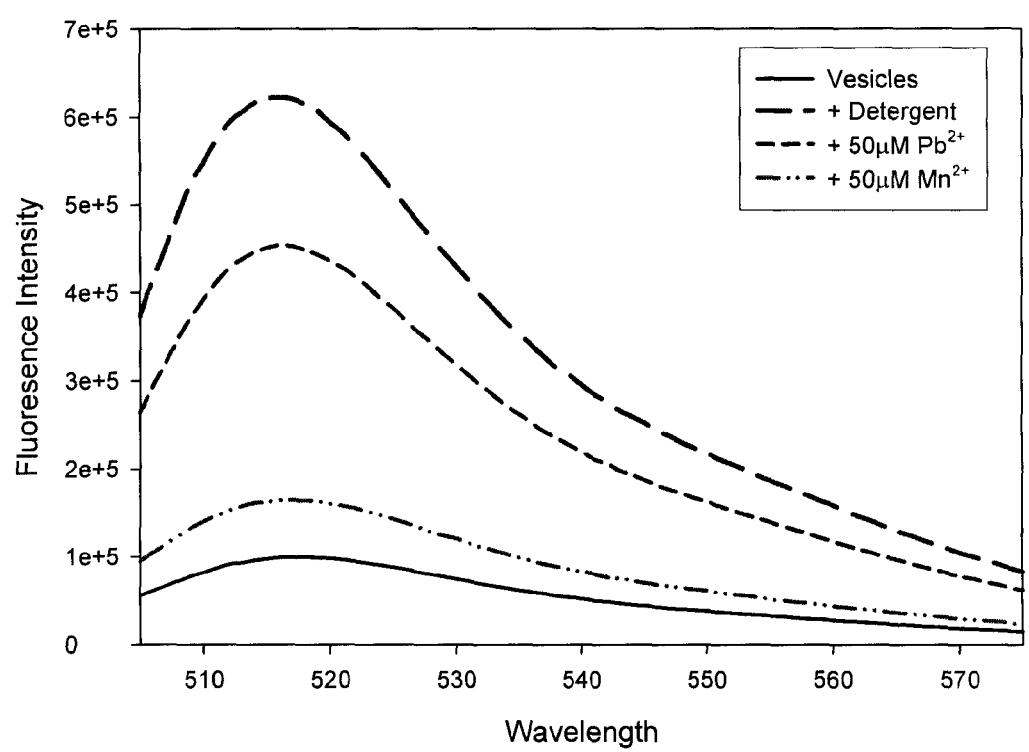
FIG. 7 is a collection of fluorescence spectra for vesicles exposed to 50 micromolar ($\mu$M) $Pb^{2+}$ ion, to 50 $\mu$M $Mn^{2+}$ ion, to Triton-X detergent, and to no added ions or detergent.

The effect of three separate reagents on the vesicles was measured. FIG. 7 is a collection of fluorescence spectra for vesicles exposed to 50 micromolar (μM) $Pb^{2+}$ ion, to 50 μM $Mn^{2+}$ ion, to Triton-X detergent, and to no added ions or detergent (labeled "vesicles"), where the spectra were recorded 5 minutes after addition of the reagent. Upon addition of $Pb^{2+}$, the fluorescence intensity increased, indicating release of the contents of the vesicles. In contrast, addition of $Mn^{2+}$ resulted in minimal increase in fluorescence intensity relative to the control sample. Addition of the detergent Triton-X, which is known to destabilize vesicles, resulted in an increase in fluorescence intensity greater than that observed with $Pb^{2+}$.

Figure 8:
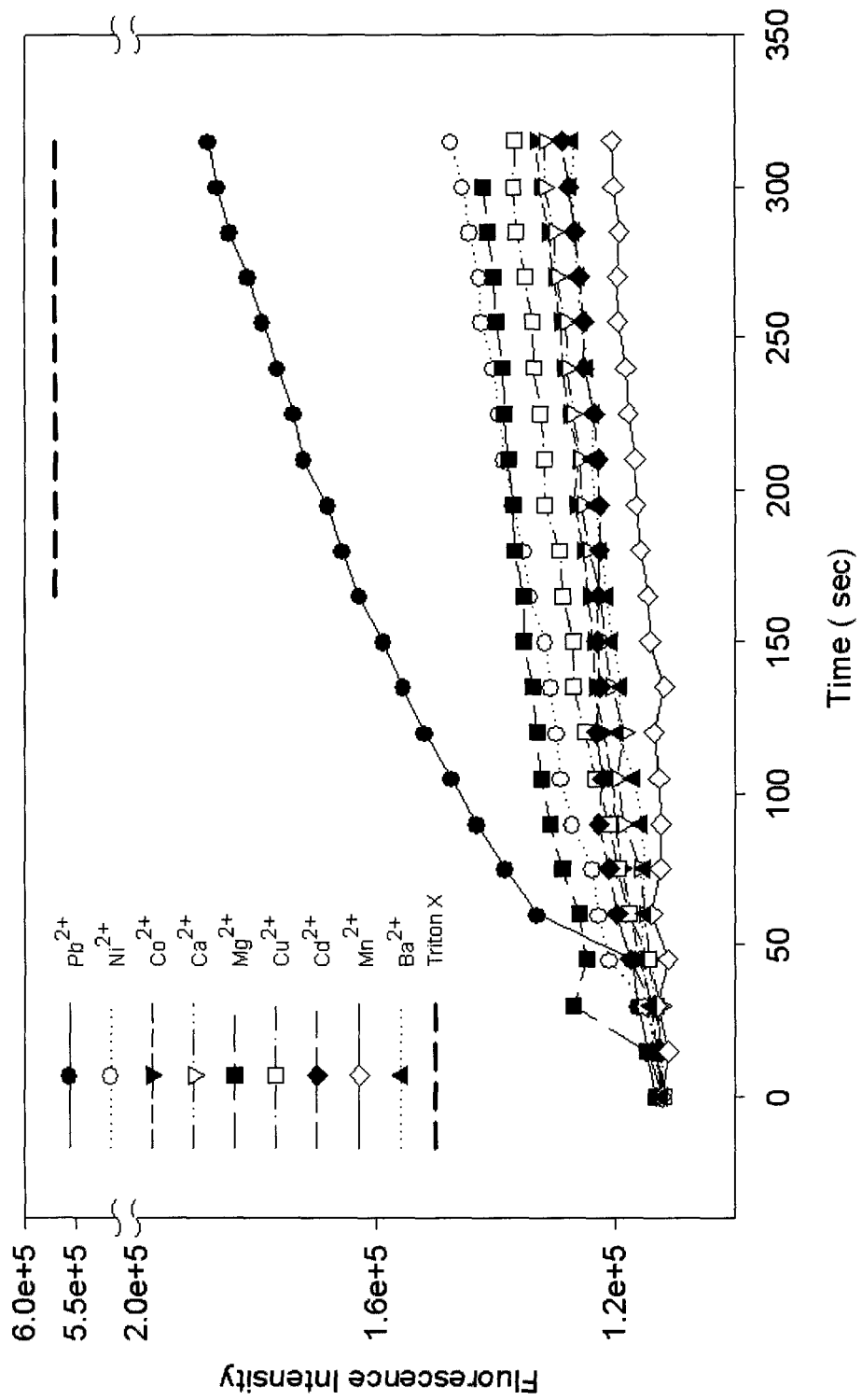
FIG. 8 is a graph of normalized fluorescence intensity over time after exposure of the vesicles to 40 $\mu$M of different divalent metal ions, or to a detergent.

The kinetic effect of different metal ions on the vesicles also was measured. FIG. 8 is a graph of normalized fluorescence intensity over time after exposure of the vesicles to 40 μM either of $Mn^{2+}$, $Pb^{2+}$ or other metal ions. The result demonstrated that $Pb^{2+}$ ruptured the vesicles. Other metal ions had minor effects on dye release, which probably was due not to the affinity of metal ions, but rather to time dependent release of dye through natural leakage.

Figure 9:
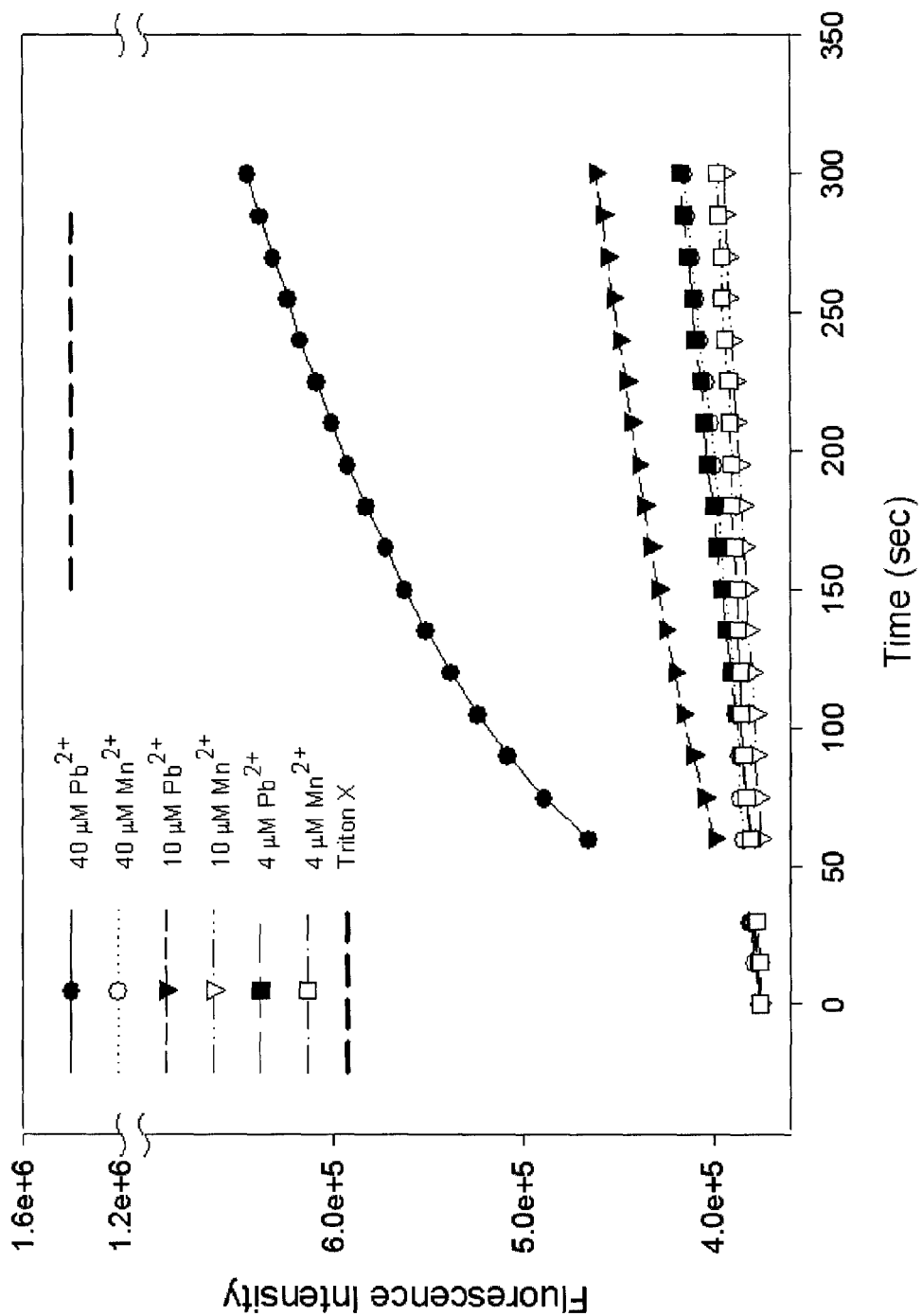
FIG. 9 is a graph of normalized fluorescence intensity over time after exposure of the vesicles to 40 $\mu$M, 10 $\mu$M or 4 $\mu$M of either $Mn^{2+}$ or $Pb^{2+}$ ions, or to a detergent.

The kinetic effect of different metal ion concentrations on the vesicles also was measured. FIG. 9 is a graph of normalized fluorescence intensity over time after exposure of the vesicles to either $Mn^{2+}$ or $Pb^{2+}$ at different concentrations. The result demonstrated that $Pb^{2+}$ ruptured the vesicles. $Mn^{2+}$ had minor effects on dye release, which probably was due not to the affinity of metal ions, but rather to time dependent release of dye through natural leakage.

These results were compared with the release observed from two types of control vesicles. In one type of control vesicle, the amphiphilic substance included in the vesicle included a DNAzyme that did not require $Pb^{2+}$ ion as a co-factor. This amphiphilic substance was prepared as described in Example 1, but using an inactive DNAzyme, resulting in a substance having the following sequence:

(SEQ ID NO: 5)
5'-Cholesterol-TEG-AACTCACTAT R(a) GGAAGAGATGTCTC
T-3'

(SEQ ID NO: 1)
5'-AAAGAGAGATCTCT TCCCCGAGCCGGTCGAAATAGTGAG-3'

The release of fluorescein from these vesicles was higher with Pb$^{2+}$ exposure than with exposure to the other metal ions. This may have been due to minor activity of the inactive DNAzyme with lead ion. When compared to active DNAzyme vesicles, however, the amount of release was insignificant.

Example 4

Synthesis of Amphiphilic Substance Including Polynucleotide Group Containing DNAzyme and Stabilizing Group The oligonucleotides (5)-17DS-(1)-Choi and Biotin-(7)-17E-(-1) were combined to form an amphiphilic substance. The first polynucleotide segment of the amphiphilic substance included a cholesterol group as a hydrophobic group, and included a substrate for a nucleic acid-based enzyme based on DNA (DNAzyme). The second polynucleotide segment of the amphiphilic substance included the DNAzyme, and included a sequence complementary to a sequence in the first segment. The biotin was linked to streptavidin to form an amphiphilic substance that included a streptavidin group as a stabilizing group.

An initial amphiphilic substance was prepared using the protocol of Example 1. This initial amphiphilic substance was mixed with 6 µL of 2.2 mM biotin solution. Streptavidin (10.5 µL) was added to the mixture and mixed by gentle vortexing. The streptavidin addition was repeated three more times, for a total of four additions. The sequence of the resulting amphiphilic substance was:

(SEQ ID NO: 5)
5'-Cholesterol-TEG-AACTCACTAT R(a) GGAAGAGATGTCTC T-3'

(SEQ ID NO: 6)
Streptavidin-Biotin-TEG-5'-AAAGAGAGATCTCTTCTCCGAGC CGGTCGAAATA-GTGAG 3'

Example 5

Formation of Stable Vesicle Including Amphiphilic Substance Containing Polynucleotide Group and Stabilizing Group DOPE was combined with the amphiphilic substance of Example 4 in water containing 100 mM NaCl and 50 mM pH 7.4 Hepes buffer containing 50 mM fluorescein. The mixture formed stable vesicles having an average diameter of 1 micrometer. In contrast, DOPE in buffer containing 50 mM fluorescein without the amphiphilic substance produced only an agglomeration of the lipid. Exposure of the stable vesicles to Pb$^{2+}$ ruptured the vesicles and released the fluorescein. The results of this study were observed by optical microscopy.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. An amphiphilic substance, comprising:
a polynucleotide group comprising a first polynucleotide segment and a second polynucleotide segment that is at least partially complementary to the first polynucleotide segment, wherein the first polynucleotide segment comprises an aptamer, and wherein base pairing between the first polynucleotide segment and the second polynucleotide segment occurs in an absence of binding of an effector specific for the aptamer and base pairing between the first polynucleotide segment and the second polynucleotide segment is disrupted in the presence of the effector;
a hydrophobic group attached to only one of the first polynucleotide segment and the second polynucleotide segment; and
a stabilizing group, attached to the first or second polynucleotide segment that is not attached to the hydrophobic group, where the stabilizing group is different from the hydrophobic group and the first and second polynucleotide segments.

2. The amphiphilic substance of claim 1, where the hydrophobic group comprises a member selected from the group consisting of a wax group, a fatty acyl, a triglyceride, a phosphoglyceride, a sphingolipid group, a prostaglandin group, a terpene group and a steroid group.

3. The amphiphilic substance of claim 1, further comprising a linking group between the first polynucleotide segment and the second polynucleotide segment.

4. A lipid vesicle, comprising:
a vesicle wall surrounding an internal space, the vesicle wall including a lipid bilayer comprising a first polar lipid that is an unstable vesicle former;
the amphiphilic substance of claim 1, wherein the hydrophobic group is at least partially within the lipid bilayer;
at least one bioactive agent within the internal space; and
a polar liquid.

5. The lipid vesicle of claim 4, where the lipid bilayer further comprises a second polar lipid that is a stable vesicle former.

6. The lipid vesicle of claim 4, where the first polar lipid comprises a phospholipid.

7. The lipid vesicle of claim 4, where the first polar lipid comprises DOPE.

8. The amphiphilic substance of claim 1, where the effector is a metal ion, polynucleotide, protein, or organic compound.

9. The amphiphilic substance of claim 1, where the effector is adenosine.

10. The lipid vesicle of claim 4, wherein the disruption of the base pairing between the first polynucleotide segment and the second polynucleotide segment allows the stabilizing group to separate from the vesicle.

11. The lipid vesicle of claim 4, where the disruption of the base pairing between the between the first polynucleotide segment and the second polynucleotide segment causes the vesicle to rupture.

12. The amphiphilic substance of claim 1 where the stabilizing group is polyethylene glycol, avidin, streptavidin, neutravidin, poly(acrylic acid), poly(methacrylic acid), sulfonated polystyrene, polyacrylamide, poly(vinyl alcohol), poly(vinyl imidazole), poly(ethylene imine), poly(hydroxybutyrate) poly(hydroxyvalerate), a polyester, poly(amidoamine) dendrons and dendrimers (PAMAM), or a combination thereof.

13. The amphiphilic substance of claim 1, where at least one of the first polynucleotide aptamer segment or the second polynucleotide segment further comprises a nucleic acid-based enzyme.

* * * * *

```
SEQUENCE LISTING

<160> NUMBER OF SEQ ID NOS: 6

<210> SEQ ID NO 1
<211> LENGTH: 39
<212> TYPE: DNA
<213> ORGANISM: Artificial Sequence
<220> FEATURE:
<223> OTHER INFORMATION: oligonucleotide (7)-17E-(-1)

<400> SEQUENCE: 1
aaagagagat ctcttctccg agccggtcga aatagtgag                    39

<210> SEQ ID NO 2
<211> LENGTH: 39
<212> TYPE: DNA
<213> ORGANISM: Artificial Sequence
<220> FEATURE:
<223> OTHER INFORMATION: Oligonucleotide Biotin-(7)-17E-(-1)
<220> FEATURE:
<221> NAME/KEY: misc_feature
<222> LOCATION: (1)..(1)
<223> OTHER INFORMATION: Biotin on 5'-end of oligonucleotide

<400> SEQUENCE: 2
aaagagagat ctcttctccg agccggtcga aatagtgag                    39

<210> SEQ ID NO 3
<211> LENGTH: 39
<212> TYPE: DNA
<213> ORGANISM: Artificial Sequence
<220> FEATURE:
<223> OTHER INFORMATION: oligonucleotide SH-(7)-17E-(-1))
<220> FEATURE:
<221> NAME/KEY: misc_feature
```

-continued

```
<222> LOCATION: (1)..(1)
<223> OTHER INFORMATION: Thiol on 5'-end of oligonucleotide.

<400> SEQUENCE: 3
aaagagagat ctcttctccg agccggtcga aatagtgag                    39

<210> SEQ ID NO 4
<211> LENGTH: 26
<212> TYPE: DNA
<213> ORGANISM: Artificial Sequence
<220> FEATURE:
<223> OTHER INFORMATION: Oligonucleotide (5)-17DS-(1)-Chol
<220> FEATURE:
<221> NAME/KEY: misc_feature
<222> LOCATION: (1)..(1)
<223> OTHER INFORMATION: Cholesterol on 5'-end
<220> FEATURE:
<221> NAME/KEY: misc_feature
<222> LOCATION: (11)..(11)
<223> OTHER INFORMATION: A at position 11 is a ribonucleotide

<400> SEQUENCE: 4
aactcactat aggaagagat gtctct                                  26

<210> SEQ ID NO 5
<211> LENGTH: 26
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (1)..(1)
<223> OTHER INFORMATION: Cholesterol-TEG on 5'-end
<220> FEATURE:
<221> NAME/KEY: misc_feature
<222> LOCATION: (11)..(11)
<223> OTHER INFORMATION: A at position 11 is a ribonucleotide

<400> SEQUENCE: 5
aactcactat aggaagagat gtctct                                  26

<210> SEQ ID NO 6
<211> LENGTH: 39
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (1)..(1)
<223> OTHER INFORMATION: Streptavidin-Biotin-TEG on 5'-end

<400> SEQUENCE: 6
aaagagagat ctcttctccg agccggtcga aatagtgag                    39
```